(12) United States Patent
von Badinski et al.

(10) Patent No.: US 12,393,227 B2
(45) Date of Patent: *Aug. 19, 2025

(54) WEARABLE COMPUTING DEVICE

(71) Applicant: Ouraring Inc., San Francisco, CA (US)

(72) Inventors: Curt C. von Badinski, Valencia, CA (US); Michael J. Strasser, San Francisco, CA (US); Peter Twiss, Lakewood, CA (US)

(73) Assignee: Ouraring, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/982,887

(22) Filed: Dec. 16, 2024

(65) Prior Publication Data

US 2025/0155927 A1 May 15, 2025

Related U.S. Application Data

(60) Continuation of application No. 18/323,387, filed on May 24, 2023, now Pat. No. 12,210,381, which is a
(Continued)

(51) Int. Cl.
*A61B 5/332* (2021.01)
*A61B 5/00* (2006.01)
(Continued)

(52) U.S. Cl.
CPC ............... *G06F 1/163* (2013.01); *A61B 5/01* (2013.01); *A61B 5/0205* (2013.01); *A61B 5/021* (2013.01); *A61B 5/02416* (2013.01); *A61B 5/1118* (2013.01); *A61B 5/14532* (2013.01); *A61B 5/1455* (2013.01); *A61B 5/332* (2021.01); *A61B 5/349* (2021.01); *A61B 5/681* (2013.01);
(Continued)

(58) Field of Classification Search
CPC ..... A61B 5/01; A61B 5/0205; A61B 5/02416; A61B 5/1455; A61B 5/332; A61B 5/6826
See application file for complete search history.

(56) References Cited

U.S. PATENT DOCUMENTS 1,589,547 A 6/1926 Novack
2,048,878 A 7/1936 Moldenhauer
(Continued)

FOREIGN PATENT DOCUMENTS

AU 2008290211 A1 2/2009
AU 2012207287 B2 7/2012
(Continued)

OTHER PUBLICATIONS

Volker Konig et al., Reflectance Pulse Oximetry—Principles and Obstetric Application in the Zurich System, 14 Journal of Clinical Monitoring (Aug. 1998) ("Konig").
(Continued)

*Primary Examiner* — Manuel A Rivera Vargas
(74) *Attorney, Agent, or Firm* — Holland & Hart LLP

(57) ABSTRACT

A finger-worn wearable ring device may include a ring-shaped housing, a printed circuit board, and a sensor module that includes one or more light-emitting components and one or more light-receiving components. The wearable ring device may further include a communication module configured to wirelessly communicate with an application executable on a user device.

16 Claims, 64 Drawing Sheets

Related U.S. Application Data continuation of application No. 18/179,272, filed on Mar. 6, 2023, now Pat. No. 11,874,701, which is a continuation of application No. 17/519,201, filed on Nov. 4, 2021, now Pat. No. 11,599,147, which is a continuation of application No. 17/013,348, filed on Sep. 4, 2020, now Pat. No. 11,188,124, which is a continuation of application No. 16/224,686, filed on Dec. 18, 2018, now Pat. No. 10,768,666, which is a division of application No. 15/444,217, filed on Feb. 27, 2017, now Pat. No. 10,156,867, which is a division of application No. 14/556,062, filed on Nov. 28, 2014, now Pat. No. 9,582,034.

(60) Provisional application No. 62/006,835, filed on Jun. 2, 2014, provisional application No. 61/910,201, filed on Nov. 29, 2013.

(51) Int. Cl.

| | | |
|---|---|---|
| *A61B 5/01* | (2006.01) | |
| *A61B 5/0205* | (2006.01) | |
| *A61B 5/021* | (2006.01) | |
| *A61B 5/024* | (2006.01) | |
| *A61B 5/11* | (2006.01) | |
| *A61B 5/145* | (2006.01) | |
| *A61B 5/1455* | (2006.01) | |
| *A61B 5/349* | (2021.01) | |
| *G01P 15/00* | (2006.01) | |
| *G02B 19/00* | (2006.01) | |
| *G04G 21/02* | (2010.01) | |
| *G06F 1/16* | (2006.01) | |
| *G06F 3/01* | (2006.01) | |
| *G06F 3/14* | (2006.01) | |
| *G06F 21/32* | (2013.01) | |
| *G06V 10/75* | (2022.01) | |
| *G06V 40/10* | (2022.01) | |
| *G06V 40/70* | (2022.01) | |
| *G08B 5/36* | (2006.01) | |
| *G08B 21/02* | (2006.01) | |
| *G08C 17/02* | (2006.01) | |
| *H02J 7/00* | (2006.01) | |
| *H02J 7/35* | (2006.01) | |
| *H02S 40/22* | (2014.01) | |
| *H02S 99/00* | (2014.01) | |

(52) U.S. Cl.
CPC ............ *A61B 5/6826* (2013.01); *G01P 15/00* (2013.01); *G02B 19/0052* (2013.01); *G02B 19/0061* (2013.01); *G04G 21/02* (2013.01); *G04G 21/025* (2013.01); *G06F 1/1635* (2013.01); *G06F 3/014* (2013.01); *G06F 3/017* (2013.01); *G06F 3/14* (2013.01); *G06F 21/32* (2013.01); *G06V 10/751* (2022.01); *G06V 40/10* (2022.01); *G06V 40/70* (2022.01); *G08B 5/36* (2013.01); *G08B 21/02* (2013.01); *G08C 17/02* (2013.01); *H02J 7/0044* (2013.01); *H02J 7/35* (2013.01); *H02S 40/22* (2014.12); *H02S 99/00* (2013.01); *A61B 2560/0214* (2013.01); *A61B 2560/0412* (2013.01); *A61B 2562/146* (2013.01); *A61B 2562/164* (2013.01); *A61B 2562/166* (2013.01); *G02B 19/0042* (2013.01); *G06V 40/15* (2022.01); *G08C 2201/30* (2013.01); *Y02E 10/52* (2013.01)

(56) References Cited

U.S. PATENT DOCUMENTS

| | | |
|---|---|---|
| 3,022,648 A | 2/1962 | Thaler |
| 3,653,051 A | 3/1972 | Wu |
| 3,684,125 A | 8/1972 | Laurizio |
| 4,012,629 A | 3/1977 | Simms |
| 4,407,295 A | 8/1983 | Steuer et al. |
| 4,427,303 A | 1/1984 | Matthias |
| 4,431,905 A | 2/1984 | Slocum |
| 4,541,207 A | 9/1985 | Antonson |
| 4,830,014 A | 5/1989 | Goodman et al. |
| 4,880,304 A | 11/1989 | Jaeb et al. |
| 5,191,891 A | 3/1993 | Righter |
| 5,333,616 A | 8/1994 | Mills et al. |
| 5,382,778 A | 1/1995 | Takahira et al. |
| 5,490,523 A | 2/1996 | Isaacson et al. |
| 5,832,296 A | 11/1998 | Wang et al. |
| 5,889,737 A | 3/1999 | Alameh et al. |
| 5,964,701 A | 10/1999 | Asada et al. |
| 6,101,843 A | 8/2000 | Nagano |
| 6,108,197 A | 8/2000 | Janik |
| 6,201,698 B1 | 3/2001 | Hunter |
| 6,236,037 B1 | 5/2001 | Asada et al. |
| 6,255,800 B1 | 7/2001 | Bork |
| 6,297,808 B1 | 10/2001 | Yang |
| 6,402,690 B1 | 6/2002 | Rhee et al. |
| 6,495,283 B1 | 12/2002 | Yoon et al. |
| 6,502,906 B1 | 1/2003 | Chen |
| 6,546,749 B1 | 4/2003 | Canty |
| 6,608,562 B1 | 8/2003 | Kimura et al. |
| 6,619,835 B2 | 9/2003 | Kita |
| 6,672,513 B2 | 1/2004 | Bard et al. |
| 6,699,199 B2 | 3/2004 | Asada et al. |
| 6,745,061 B1 | 6/2004 | Hicks et al. |
| 6,922,592 B2 | 7/2005 | Thompson et al. |
| 7,161,484 B2 | 1/2007 | Tsoukalis |
| 7,190,986 B1 | 3/2007 | Hannula et al. |
| 7,238,159 B2 | 7/2007 | Banet et al. |
| 7,374,540 B2 | 5/2008 | Schnall |
| 7,375,494 B2 | 5/2008 | Daniel et al. |
| 7,427,979 B2 | 9/2008 | Park et al. |
| 7,444,001 B2 | 10/2008 | Roberts et al. |
| 7,468,036 B1 | 12/2008 | Rulkov et al. |
| 7,517,222 B2 | 4/2009 | Rohrbach et al. |
| 7,526,927 B2 | 5/2009 | Pinto |
| 7,548,040 B2 | 6/2009 | Lee et al. |
| 7,555,327 B2 | 6/2009 | Matlock |
| 7,637,746 B2 | 12/2009 | Lindberg et al. |
| 7,641,614 B2 | 1/2010 | Asada et al. |
| 7,674,231 B2 | 3/2010 | McCombie et al. |
| 7,733,224 B2 | 6/2010 | Tran |
| 8,031,172 B2 | 10/2011 | Kruse |
| 8,157,161 B2 | 4/2012 | Yach |
| 8,157,731 B2 | 4/2012 | Teller et al. |
| 8,179,604 B1 | 5/2012 | Prada Gomez et al. |
| 8,251,903 B2 | 8/2012 | LeBoeuf et al. |
| 8,270,914 B2 | 9/2012 | Pascolini et al. |
| 8,346,327 B2 | 1/2013 | Campbell et al. |
| 8,373,656 B2 | 2/2013 | Hou et al. |
| 8,378,967 B2 | 2/2013 | Noda et al. |
| 8,398,546 B2 | 3/2013 | Pacione et al. |
| 8,421,748 B2 | 4/2013 | Tanaka |
| 8,457,654 B1 | 6/2013 | Roskind |
| 8,512,238 B2 | 8/2013 | Nissilä et al. |
| 8,515,506 B2 | 8/2013 | Ridder et al. |
| 8,554,297 B2 | 10/2013 | Moon et al. |
| 8,568,330 B2 | 10/2013 | Mollicone et al. |
| 8,570,372 B2 | 10/2013 | Russell |
| 8,583,167 B2 | 11/2013 | Chun |
| 8,588,032 B2 | 11/2013 | Geyer et al. |
| 8,599,572 B2 | 12/2013 | Neudecker et al. |
| 8,602,988 B2 | 12/2013 | Hunt et al. |
| 8,626,249 B2 | 1/2014 | Ungari et al. |
| 8,638,190 B1 | 1/2014 | Want et al. |
| 8,682,421 B2 | 3/2014 | Riftine |
| 8,700,111 B2 | 4/2014 | LeBoeuf et al. |
| 8,715,204 B2 | 5/2014 | Webster et al. |

(56) References Cited

U.S. PATENT DOCUMENTS

| | | |
|---|---|---|
| 8,717,165 B2 | 5/2014 | Gernandt et al. |
| 8,764,651 B2 | 7/2014 | Tran |
| 8,795,184 B2 | 8/2014 | Niwa et al. |
| 8,888,720 B2 | 11/2014 | Hudson |
| 8,936,552 B2 | 1/2015 | Kateraas et al. |
| 8,954,135 B2 | 2/2015 | Yuen et al. |
| 8,957,988 B2 | 2/2015 | Wexler et al. |
| 8,961,414 B2 | 2/2015 | Teller et al. |
| 8,974,349 B2 | 3/2015 | Weast et al. |
| 8,988,349 B2 | 3/2015 | Alberth et al. |
| 9,076,589 B2 | 7/2015 | Wright et al. |
| 9,095,291 B2 | 8/2015 | Soller et al. |
| 9,110,505 B2 | 8/2015 | Mastandrea, Jr. |
| 9,113,793 B2 | 8/2015 | Terumoto et al. |
| 9,130,651 B2 | 9/2015 | Tabe |
| 9,148,717 B2 | 9/2015 | Shaffer |
| 9,165,117 B2 | 10/2015 | Teller et al. |
| 9,197,270 B2 | 11/2015 | Ying et al. |
| 9,202,111 B2 | 12/2015 | Arnold et al. |
| 9,203,463 B2 | 12/2015 | Asrani et al. |
| 9,218,058 B2 | 12/2015 | Bress et al. |
| 9,259,182 B2 | 2/2016 | Okuda et al. |
| 9,277,880 B2 | 3/2016 | Poeze et al. |
| 9,285,830 B2 | 3/2016 | Alcazar |
| 9,289,135 B2 | 3/2016 | LeBoeuf et al. |
| 9,311,825 B2 | 4/2016 | Lusted et al. |
| 9,313,609 B2 | 4/2016 | Prencipe |
| 9,335,790 B2 | 5/2016 | Stotler |
| 9,345,404 B2 | 5/2016 | Proud |
| 9,385,396 B2 | 7/2016 | Goh et al. |
| 9,398,870 B2 | 7/2016 | Bechtel et al. |
| 9,414,125 B2 | 8/2016 | Ferren et al. |
| 9,423,418 B2 | 8/2016 | Alameh et al. |
| 9,439,567 B2 | 9/2016 | Carter et al. |
| 9,519,755 B2 | 12/2016 | Saalasti et al. |
| 9,538,564 B2 | 1/2017 | Belogolovy |
| 9,563,234 B2 | 2/2017 | Popalis et al. |
| 9,568,492 B2 | 2/2017 | Yuen |
| 9,582,034 B2 | 2/2017 | von Badinski |
| 9,594,404 B2 | 3/2017 | Yoon et al. |
| 9,615,791 B2 | 4/2017 | Zhang et al. |
| 9,626,478 B2 | 4/2017 | Armstrong |
| 9,639,119 B2 | 5/2017 | Seok et al. |
| 9,639,120 B2 | 5/2017 | Wu |
| 9,642,567 B2 | 5/2017 | Tateda et al. |
| 9,651,533 B2 | 5/2017 | Islam |
| 9,662,053 B2 | 5/2017 | Richards et al. |
| 9,704,154 B2 | 7/2017 | Xing et al. |
| 9,711,060 B1 | 7/2017 | Lusted et al. |
| 9,720,443 B2 | 8/2017 | Malhotra |
| 9,734,304 B2 | 8/2017 | Blackadar et al. |
| 9,734,477 B2 | 8/2017 | Weast et al. |
| 9,743,357 B2 | 8/2017 | Tabe |
| 9,757,040 B2 | 9/2017 | Islam |
| 9,788,789 B2 | 10/2017 | Bailey |
| 9,795,323 B2 | 10/2017 | Yuen et al. |
| 9,801,553 B2 | 10/2017 | Chadderdon et al. |
| 9,801,993 B2 | 10/2017 | Barrett et al. |
| 9,807,319 B2 | 10/2017 | Teich et al. |
| 9,808,204 B2 | 11/2017 | LeBoeuf et al. |
| 9,833,159 B2 | 12/2017 | Chu et al. |
| 9,861,286 B1 | 1/2018 | Islam |
| 9,885,698 B2 | 2/2018 | Islam |
| 9,955,919 B2 | 5/2018 | LeBoeuf et al. |
| 10,042,422 B2 | 8/2018 | Morun et al. |
| 10,061,350 B2 | 8/2018 | Magi |
| 10,073,953 B2 | 9/2018 | Xing |
| 10,076,282 B2 | 9/2018 | LeBoeuf et al. |
| 10,085,689 B1 | 10/2018 | Giuffrida et al. |
| 10,088,894 B2 | 10/2018 | Grossman et al. |
| 10,098,546 B2 | 10/2018 | Islam |
| 10,111,594 B2 | 10/2018 | Hielscher et al. |
| 10,111,615 B2 | 10/2018 | Russell et al. |
| 10,139,859 B2 | 11/2018 | von Badinski et al. |
| 10,152,082 B2 | 12/2018 | Bailey |
| 10,156,867 B2 | 12/2018 | von Badinski et al. |
| 10,165,954 B2 | 1/2019 | Lee |
| 10,178,973 B2 | 1/2019 | Venkatraman et al. |
| 10,213,113 B2 | 2/2019 | Islam |
| 10,219,709 B2 | 3/2019 | Basu |
| 10,226,213 B2 | 3/2019 | Xing et al. |
| 10,244,190 B2 | 3/2019 | Boulanger et al. |
| 10,258,265 B1 | 4/2019 | Poeze et al. |
| 10,258,280 B2 | 4/2019 | Justice et al. |
| 10,264,982 B2 | 4/2019 | Ahmed et al. |
| 10,281,953 B2 | 5/2019 | von Badinski et al. |
| 10,299,736 B2 | 5/2019 | Najafi et al. |
| 10,303,867 B2 | 5/2019 | Schröder |
| 10,321,829 B2 | 6/2019 | Colley et al. |
| 10,321,862 B2 | 6/2019 | Dalene et al. |
| 10,327,651 B2 | 6/2019 | Bonomi et al. |
| 10,331,168 B2 | 6/2019 | von Badinski et al. |
| 10,376,190 B1 | 8/2019 | Poeze et al. |
| 10,448,840 B2 | 10/2019 | LeBoeuf et al. |
| 10,456,066 B2 | 10/2019 | Bechtel et al. |
| 10,456,089 B2 | 10/2019 | Gourmelon et al. |
| 10,463,283 B2 | 11/2019 | Ferber et al. |
| 10,496,131 B2 | 12/2019 | von Badinski et al. |
| 10,506,980 B2 | 12/2019 | Oleson |
| 10,582,886 B2 | 3/2020 | Poeze et al. |
| 10,586,620 B2 | 3/2020 | Iizuka |
| 10,588,553 B2 | 3/2020 | Poeze et al. |
| 10,588,554 B2 | 3/2020 | Poeze et al. |
| 10,607,732 B2 | 3/2020 | Xing et al. |
| 10,610,138 B2 | 4/2020 | Poeze et al. |
| 10,617,338 B2 | 4/2020 | Poeze et al. |
| 10,624,563 B2 | 4/2020 | Poeze et al. |
| 10,627,861 B2 | 4/2020 | Connor |
| 10,631,765 B1 | 4/2020 | Poeze et al. |
| 10,709,366 B1 | 7/2020 | Poeze et al. |
| 10,729,388 B2 | 8/2020 | Reihman et al. |
| 10,736,507 B2 | 8/2020 | Muhsin et al. |
| 10,758,166 B2 | 9/2020 | Poeze et al. |
| 10,768,666 B2 | 9/2020 | von Badinski et al. |
| 10,827,979 B2 | 11/2020 | LeBoeuf et al. |
| 10,842,389 B2 | 11/2020 | LeBoeuf et al. |
| 10,884,455 B2 | 1/2021 | von Badinski et al. |
| 10,898,083 B2 | 1/2021 | LeBoeuf et al. |
| 10,901,460 B2 | 1/2021 | von Badinski et al. |
| 10,912,500 B2 | 2/2021 | Poeze et al. |
| 10,912,501 B2 | 2/2021 | Poeze et al. |
| 10,912,502 B2 | 2/2021 | Poeze et al. |
| 10,932,701 B2 | 3/2021 | Acharya et al. |
| 10,945,648 B2 | 3/2021 | Poeze et al. |
| 10,973,421 B2 | 4/2021 | Wisløff et al. |
| 11,029,199 B2 | 6/2021 | Turgeon et al. |
| 11,039,090 B2 | 6/2021 | Liu |
| 11,160,455 B2 | 11/2021 | Islam |
| 11,185,241 B2 | 11/2021 | Ahmed et al. |
| 11,188,124 B2 | 11/2021 | von Badinski et al. |
| 11,224,381 B2 | 1/2022 | McHale et al. |
| 11,330,993 B2 | 5/2022 | Basu |
| 11,410,765 B2 | 8/2022 | Ahmed et al. |
| 11,426,123 B2 | 8/2022 | Bailey et al. |
| 11,484,229 B2 | 11/2022 | Poeze et al. |
| 11,564,577 B2 | 1/2023 | Islam |
| 11,574,722 B2 | 2/2023 | Ahmed et al. |
| 11,589,812 B2 | 2/2023 | LeBoeuf et al. |
| 11,599,147 B2 | 3/2023 | von Badinski et al. |
| 11,638,532 B2 | 5/2023 | Poeze et al. |
| 11,642,036 B2 | 5/2023 | Poeze et al. |
| 11,642,037 B2 | 5/2023 | Poeze et al. |
| 11,647,914 B2 | 5/2023 | Poeze et al. |
| 11,660,006 B2 | 5/2023 | LeBoeuf et al. |
| 11,678,805 B2 | 6/2023 | Islam et al. |
| 11,771,348 B2 | 10/2023 | Bechtel et al. |
| 11,857,337 B1 | 1/2024 | Miller et al. |
| 11,868,178 B2 | 1/2024 | von Badinski et al. |
| 11,868,179 B2 | 1/2024 | von Badinski et al. |
| 11,874,701 B2 | 1/2024 | von Badinski et al. |
| 11,874,702 B2 | 1/2024 | von Badinski et al. |
| 11,877,821 B2 | 1/2024 | Tran |
| 2002/0156352 A1 | 10/2002 | Eggers |
| 2002/0198443 A1 | 12/2002 | Ting |

(56) References Cited

U.S. PATENT DOCUMENTS

| | | |
|---|---|---|
| 2003/0139654 A1 | 7/2003 | Kim et al. |
| 2003/0142065 A1 | 7/2003 | Pahlavan |
| 2003/0181835 A1 | 9/2003 | Klein |
| 2004/0032333 A1 | 2/2004 | Hatt |
| 2004/0039254 A1 | 2/2004 | Stivoric et al. |
| 2004/0087845 A1 | 5/2004 | Katarow et al. |
| 2004/0190383 A1 | 9/2004 | Marcucelli et al. |
| 2005/0038348 A1 | 2/2005 | Avicola et al. |
| 2005/0080344 A1 | 4/2005 | Nishii et al. |
| 2005/0099799 A1 | 5/2005 | Cugini et al. |
| 2005/0156980 A1 | 7/2005 | Walker |
| 2005/0189906 A1 | 9/2005 | Sun |
| 2006/0046709 A1 | 3/2006 | Krumm et al. |
| 2006/0142968 A1 | 6/2006 | Han et al. |
| 2006/0202618 A1 | 9/2006 | Ishii et al. |
| 2006/0211924 A1 | 9/2006 | Dalke et al. |
| 2007/0059595 A1 | 3/2007 | Endo et al. |
| 2007/0060807 A1 | 3/2007 | Oishi |
| 2007/0064542 A1 | 3/2007 | Fukushima |
| 2007/0100218 A1 | 5/2007 | Sweitzer et al. |
| 2007/0100666 A1 | 5/2007 | Stivoric et al. |
| 2007/0123756 A1 | 5/2007 | Kitajima et al. |
| 2007/0182545 A1 | 8/2007 | Baum et al. |
| 2008/0004510 A1 | 1/2008 | Tanzawa et al. |
| 2008/0024961 A1 | 1/2008 | Anderson et al. |
| 2008/0030346 A1 | 2/2008 | Despotis |
| 2008/0045806 A1 | 2/2008 | Keppler |
| 2008/0048036 A1 | 2/2008 | Matsumoto et al. |
| 2008/0171915 A1 | 7/2008 | Kawajiri et al. |
| 2008/0208009 A1 | 8/2008 | Shklarski |
| 2008/0266118 A1 | 10/2008 | Pierson et al. |
| 2008/0285812 A1 | 11/2008 | Rensen et al. |
| 2009/0054751 A1 | 2/2009 | Babashan et al. |
| 2009/0096746 A1 | 4/2009 | Kruse et al. |
| 2009/0221937 A1 | 9/2009 | Smith et al. |
| 2009/0306485 A1 | 12/2009 | Bell |
| 2010/0016681 A1 | 1/2010 | Charles et al. |
| 2010/0056886 A1 | 3/2010 | Hurtubise et al. |
| 2010/0100004 A1 | 4/2010 | Van Someren |
| 2010/0145236 A1 | 6/2010 | Greenberg et al. |
| 2010/0156624 A1 | 6/2010 | Hounsell |
| 2010/0168531 A1 | 7/2010 | Shaltis et al. |
| 2010/0198034 A1 | 8/2010 | Thomas et al. |
| 2010/0217102 A1 | 8/2010 | LeBoeuf et al. |
| 2010/0219989 A1 | 9/2010 | Asami et al. |
| 2010/0298677 A1 | 11/2010 | Lu et al. |
| 2010/0324389 A1 | 12/2010 | Moon et al. |
| 2011/0028814 A1 | 2/2011 | Petersen et al. |
| 2011/0038511 A1 | 2/2011 | Takiguchi |
| 2011/0057901 A1 | 3/2011 | Raty et al. |
| 2011/0068926 A1 | 3/2011 | Jong et al. |
| 2011/0070480 A1 | 3/2011 | Hahn et al. |
| 2011/0080339 A1 | 4/2011 | Sun et al. |
| 2011/0090148 A1 | 4/2011 | Li et al. |
| 2011/0201902 A1 | 8/2011 | Shiga et al. |
| 2011/0245633 A1 | 10/2011 | Goldberg et al. |
| 2011/0263954 A1 | 10/2011 | Lin |
| 2011/0312311 A1 | 12/2011 | Abifaker et al. |
| 2012/0016245 A1 | 1/2012 | Niwa et al. |
| 2012/0016793 A1 | 1/2012 | Peters et al. |
| 2012/0051193 A1 | 3/2012 | Yu |
| 2012/0075173 A1 | 3/2012 | Ashbrook et al. |
| 2012/0083710 A1 | 4/2012 | Yarden |
| 2012/0122519 A1 | 5/2012 | Jochheim |
| 2012/0130203 A1 | 5/2012 | Stergiou et al. |
| 2012/0136227 A1 | 5/2012 | McKenna |
| 2012/0197093 A1 | 8/2012 | LeBoeuf et al. |
| 2012/0203076 A1 | 8/2012 | Fatta et al. |
| 2012/0218184 A1 | 8/2012 | Wissmar |
| 2012/0220835 A1 | 8/2012 | Chung |
| 2012/0232431 A1 | 9/2012 | Hudson |
| 2012/0254809 A1 | 10/2012 | Yang et al. |
| 2012/0293107 A1 | 11/2012 | Ajagbe |
| 2012/0316406 A1 | 12/2012 | Rahman et al. |
| 2012/0316455 A1 | 12/2012 | Rahman et al. |
| 2012/0317024 A1 | 12/2012 | Rahman et al. |
| 2012/0326046 A1 | 12/2012 | Aslam et al. |
| 2013/0027341 A1 | 1/2013 | Masandrea |
| 2013/0044215 A1 | 2/2013 | Rothkopf et al. |
| 2013/0069583 A1 | 3/2013 | Lemelman et al. |
| 2013/0079602 A1 | 3/2013 | Picard et al. |
| 2013/0088186 A1 | 4/2013 | Hsieth |
| 2013/0096405 A1 | 4/2013 | Garfio |
| 2013/0106603 A1 | 5/2013 | Weast et al. |
| 2013/0108907 A1 | 5/2013 | Bhardwaj et al. |
| 2013/0120106 A1 | 5/2013 | Cauwels et al. |
| 2013/0131519 A1 | 5/2013 | LeBoeuf et al. |
| 2013/0144176 A1 | 6/2013 | Lec |
| 2013/0167221 A1 | 6/2013 | Vukoszaviyev et al. |
| 2013/0217326 A1 | 6/2013 | Symons |
| 2013/0183646 A1 | 7/2013 | Lusted et al. |
| 2013/0187789 A1 | 7/2013 | Lowe |
| 2013/0191789 A1 | 7/2013 | Calman et al. |
| 2013/0197680 A1 | 8/2013 | Cobbett et al. |
| 2013/0211291 A1 | 8/2013 | Tran |
| 2013/0226486 A1 | 8/2013 | Henderson et al. |
| 2013/0229338 A1 | 9/2013 | Sohn et al. |
| 2013/0261771 A1 | 10/2013 | Ten Kate |
| 2013/0271069 A1 | 10/2013 | Partovi |
| 2013/0332286 A1 | 12/2013 | Medelius et al. |
| 2014/0065956 A1 | 3/2014 | Yang et al. |
| 2014/0073486 A1 | 3/2014 | Ahmed et al. |
| 2014/0078694 A1 | 3/2014 | Wissmar |
| 2014/0102136 A1 | 4/2014 | Warren |
| 2014/0107498 A1 | 4/2014 | Bower et al. |
| 2014/0107932 A1 | 4/2014 | Luna |
| 2014/0135592 A1 | 5/2014 | Ohnemus et al. |
| 2014/0139486 A1 | 5/2014 | Mistry et al. |
| 2014/0180019 A1 | 6/2014 | Martinez et al. |
| 2014/0187160 A1 | 7/2014 | Prencipe |
| 2014/0194782 A1 | 7/2014 | Rahman et al. |
| 2014/0198035 A1 | 7/2014 | Bailey et al. |
| 2014/0218852 A1 | 8/2014 | Alcazar |
| 2014/0221789 A1 | 8/2014 | Pacione et al. |
| 2014/0221790 A1 | 8/2014 | Pacione et al. |
| 2014/0221791 A1 | 8/2014 | Pacione et al. |
| 2014/0228664 A1 | 8/2014 | Alcazar |
| 2014/0244009 A1 | 8/2014 | Mestas |
| 2014/0245784 A1 | 9/2014 | Proud et al. |
| 2014/0266731 A1 | 9/2014 | Malhotra |
| 2014/0275852 A1 | 9/2014 | Hong et al. |
| 2014/0279341 A1 | 9/2014 | Bhardwaj et al. |
| 2014/0279528 A1 | 9/2014 | Slaby et al. |
| 2014/0285416 A1 | 9/2014 | Priyantha et al. |
| 2014/0323827 A1 | 10/2014 | Ahmed et al. |
| 2014/0343371 A1 | 11/2014 | Sowers et al. |
| 2014/0343372 A1 | 11/2014 | Ahmed et al. |
| 2014/0350356 A1 | 11/2014 | Ahmed et al. |
| 2014/0361934 A1 | 12/2014 | Ely et al. |
| 2014/0361945 A1 | 12/2014 | Misra et al. |
| 2014/0364702 A1 | 12/2014 | Nasedkin |
| 2014/0375465 A1 | 12/2014 | Fenuccio et al. |
| 2015/0018654 A1 | 1/2015 | Mestha et al. |
| 2015/0031967 A1 | 1/2015 | LeBoeuf et al. |
| 2015/0037616 A1 | 2/2015 | Wyatt et al. |
| 2015/0057511 A1 | 2/2015 | Basu |
| 2015/0065090 A1 | 3/2015 | Yeh |
| 2015/0092360 A1 | 4/2015 | Stillman et al. |
| 2015/0100245 A1 | 4/2015 | Huang et al. |
| 2015/0116125 A1 | 4/2015 | Armstrong et al. |
| 2015/0118669 A1 | 4/2015 | Wisbey et al. |
| 2015/0119732 A1 | 4/2015 | Wisbey et al. |
| 2015/0120019 A1 | 4/2015 | Wisbey et al. |
| 2015/0124566 A1 | 5/2015 | Lake et al. |
| 2015/0127265 A1 | 5/2015 | Iizuka |
| 2015/0148623 A1 | 5/2015 | Benaron |
| 2015/0148625 A1 | 5/2015 | Benaron |
| 2015/0148636 A1 | 5/2015 | Benaron |
| 2015/0157256 A1 | 6/2015 | Galeev |
| 2015/0161876 A1 | 6/2015 | Castillo |
| 2015/0190072 A1 | 7/2015 | Armstrong |
| 2015/0220109 A1 | 8/2015 | von Badinski et al. |
| 2015/0238138 A1 | 8/2015 | Lehmann et al. |
| 2015/0250396 A1 | 9/2015 | Ahmed et al. |

(56) References Cited

U.S. PATENT DOCUMENTS

| | | |
|---|---|---|
| 2015/0177559 A1 | 10/2015 | Vescovi et al. |
| 2015/0277559 A1 | 10/2015 | Verscovi et al. |
| 2015/0286277 A1 | 10/2015 | Kim et al. |
| 2015/0289797 A1 | 10/2015 | Pacione et al. |
| 2015/0289800 A1 | 10/2015 | Pacione et al. |
| 2015/0289808 A1 | 10/2015 | Pacione et al. |
| 2015/0289809 A1 | 10/2015 | Pacione et al. |
| 2015/0289812 A1 | 10/2015 | Pacione et al. |
| 2015/0289818 A1 | 10/2015 | LeBoeuf et al. |
| 2015/0294575 A1 | 10/2015 | Pacione et al. |
| 2015/0294576 A1 | 10/2015 | Pacione et al. |
| 2015/0303722 A1 | 10/2015 | Li |
| 2015/0305688 A1 | 10/2015 | Rath et al. |
| 2015/0327809 A1 | 11/2015 | Tateda et al. |
| 2015/0339946 A1 | 11/2015 | Pacione et al. |
| 2015/0342468 A1 | 12/2015 | Semler et al. |
| 2015/0349556 A1 | 12/2015 | Mercando et al. |
| 2015/0380961 A1 | 12/2015 | Tseng et al. |
| 2016/0013602 A1 | 1/2016 | Strisower et al. |
| 2016/0026156 A1 | 1/2016 | Jackson et al. |
| 2016/0066827 A1 | 3/2016 | Workman et al. |
| 2016/0066839 A1 | 3/2016 | Ikeda et al. |
| 2016/0081627 A1 | 3/2016 | Mcgloin et al. |
| 2016/0100781 A1 | 4/2016 | Bechtel et al. |
| 2016/0113503 A1 | 4/2016 | Benaron |
| 2016/0120460 A1 | 5/2016 | Eom |
| 2016/0124579 A1 | 5/2016 | Tokutake |
| 2016/0171201 A1 | 6/2016 | Schröder |
| 2016/0184637 A1 | 6/2016 | Pulkkinen et al. |
| 2016/0209875 A1 | 7/2016 | Kim |
| 2016/0274621 A1 | 9/2016 | Meyer et al. |
| 2016/0324462 A1 | 11/2016 | Hämäläinen et al. |
| 2016/0327979 A1 | 11/2016 | Lettow |
| 2017/0006414 A1 | 1/2017 | Tomassini |
| 2017/0031449 A1 | 2/2017 | Karsten et al. |
| 2017/0068437 A1 | 3/2017 | Warren |
| 2017/0116472 A1 | 4/2017 | Sako et al. |
| 2017/0281081 A1 | 10/2017 | Nousiainen |
| 2017/0323285 A1 | 11/2017 | Xing et al. |
| 2018/0014782 A1 | 1/2018 | Marcus et al. |
| 2018/0055450 A1 | 3/2018 | LeBoeuf et al. |
| 2018/0156660 A1 | 6/2018 | Turgeon et al. |
| 2018/0192950 A1 | 7/2018 | LeBoeuf et al. |
| 2018/0296166 A1 | 10/2018 | LeBoeuf et al. |
| 2019/0204865 A1 | 7/2019 | von Badinski et al. |
| 2019/0302835 A1 | 10/2019 | Yamazaki |
| 2020/0129096 A1 | 4/2020 | Poeze et al. |
| 2020/0221979 A1 | 7/2020 | Poeze et al. |
| 2020/0221981 A1 | 7/2020 | Poeze et al. |
| 2021/0131863 A9 | 5/2021 | Turgeon et al. |
| 2021/0293616 A1 | 9/2021 | Capella et al. |
| 2021/0314502 A1 | 10/2021 | Liu |
| 2022/0121339 A1 | 4/2022 | Pranav et al. |
| 2022/0264302 A1 | 8/2022 | Segal |
| 2023/0066299 A1 | 3/2023 | Park et al. |
| 2023/0172455 A1 | 6/2023 | Islam |
| 2023/0253090 A1 | 8/2023 | Ahmed et al. |
| 2024/0021287 A1 | 1/2024 | Ahmed et al. |
| 2024/0023841 A1 | 1/2024 | Bechtel et al. |
| 2024/0041324 A1 | 2/2024 | Yuen et al. |

FOREIGN PATENT DOCUMENTS

| | | |
|---|---|---|
| AU | 2016200692 A1 | 2/2016 |
| AU | 2017100912 A4 | 8/2017 |
| CA | 2274521 A1 | 10/1998 |
| CA | 2369386 A1 | 1/2002 |
| CA | 2684013 A1 | 10/2008 |
| CA | 2732996 A1 | 5/2010 |
| CA | 2825167 A1 | 7/2012 |
| CA | 2883852 A1 | 3/2014 |
| CA | 2931973 A1 | 6/2015 |
| CA | 2950297 C | 1/2023 |
| CN | 2153079 Y | 1/1994 |
| CN | 2242470 Y | 12/1996 |
| CN | 1188918 A | 7/1998 |
| CN | 2618475 Y | 6/2004 |
| CN | 1843288 A | 10/2006 |
| CN | 2868185 Y | 2/2007 |
| CN | 2916709 Y | 6/2007 |
| CN | 201069519 Y | 6/2008 |
| CN | 201174038 Y | 12/2008 |
| CN | 201302659 Y | 9/2009 |
| CN | 201392456 Y | 1/2010 |
| CN | 201897708 U | 7/2011 |
| CN | 201917786 U | 8/2011 |
| CN | 202010149 U | 10/2011 |
| CN | 202110384 U | 1/2012 |
| CN | 202133955 U | 2/2012 |
| CN | 102436303 A | 5/2012 |
| CN | 102440487 A | 5/2012 |
| CN | 202270344 U | 6/2012 |
| CN | 202289426 U | 7/2012 |
| CN | 202306166 U | 7/2012 |
| CN | 202306442 U | 7/2012 |
| CN | 202362606 U | 8/2012 |
| CN | 202383438 U | 8/2012 |
| CN | 202472814 U | 10/2012 |
| CN | 202697966 U | 1/2013 |
| CN | 102389300 B | 3/2013 |
| CN | 202891907 U | 4/2013 |
| CN | 103109462 A | 5/2013 |
| CN | 202941450 U | 5/2013 |
| CN | 103126132 A | 6/2013 |
| CN | 202983025 U | 6/2013 |
| CN | 203105873 U | 8/2013 |
| CN | 203117654 U | 8/2013 |
| CN | 102166057 B | 11/2013 |
| CN | 203278941 U | 11/2013 |
| CN | 103441306 A | 12/2013 |
| CN | 203490651 U | 3/2014 |
| CN | 203505758 U | 4/2014 |
| CN | 103799624 A | 5/2014 |
| CN | 203576485 U | 5/2014 |
| CN | 103919536 A | 7/2014 |
| CN | 104081295 A | 10/2014 |
| CN | 204119281 U | 1/2015 |
| CN | 104414037 A | 3/2015 |
| CN | 104656420 A | 5/2015 |
| CN | 104665820 A | 6/2015 |
| CN | 104736047 A | 6/2015 |
| CN | 104750220 A | 7/2015 |
| CN | 204440426 U | 7/2015 |
| CN | 204520692 U | 8/2015 |
| CN | 204732935 U | 10/2015 |
| CN | 103582449 B | 6/2017 |
| CN | 104518273 B | 6/2017 |
| CN | 104145232 B | 9/2017 |
| CN | 105473021 B | 1/2018 |
| CN | 105492976 B | 11/2018 |
| CN | 105393395 B | 12/2019 |
| CN | 106104408 B | 7/2021 |
| DE | 2248710 A1 | 4/1974 |
| DE | 2829992 A1 | 1/1979 |
| DE | 3838823 A1 | 7/1989 |
| DE | 9320743 U1 | 2/1995 |
| DE | 10206672 A1 | 8/2003 |
| DE | 202006000119 U1 | 4/2006 |
| DE | 102013012339 A1 | 1/2015 |
| EP | 0660204 A1 | 6/1995 |
| EP | 0809172 A2 | 11/1997 |
| EP | 1462880 A2 | 9/2004 |
| EP | 2413263 A1 | 8/2009 |
| EP | 2281205 B1 | 7/2011 |
| EP | 2503624 A1 | 9/2012 |
| EP | 2555676 A1 | 2/2013 |
| EP | 2665417 A2 | 10/2013 |
| EP | 2660680 A1 | 11/2013 |
| EP | 2822463 A2 | 1/2015 |
| EP | 2883497 A1 | 6/2015 |
| EP | 2884889 A2 | 6/2015 |
| EP | 2892421 A1 | 7/2015 |
| EP | 2974650 A1 | 7/2015 |
| EP | 2912532 A1 | 9/2015 |

(56) References Cited

FOREIGN PATENT DOCUMENTS

| | | |
|---|---|---|
| EP | 2967358 A2 | 11/2016 |
| EP | 3128761 A1 | 2/2017 |
| EP | 2667768 B1 | 8/2017 |
| EP | 3074838 A1 | 8/2017 |
| EP | 3248539 A1 | 11/2017 |
| EP | 1906294 B1 | 7/2018 |
| EP | 3415090 A1 | 12/2018 |
| EP | 2323554 B1 | 2/2019 |
| EP | 4032469 A1 | 7/2022 |
| EP | 4071581 A1 | 10/2022 |
| FR | 2767384 B3 | 8/1997 |
| GB | 1568475 A | 5/1980 |
| GB | 2426099 B | 5/2007 |
| GB | 2431522 B | 1/2010 |
| IN | 5289CHENP2013 A | 8/2016 |
| JP | S63167292 A | 7/1988 |
| JP | H02182545 A | 7/1990 |
| JP | H07171116 A | 7/1995 |
| JP | 3018622 U | 11/1995 |
| JP | H08211166 A | 8/1996 |
| JP | 2567149 B2 | 12/1996 |
| JP | 2743462 B2 | 4/1998 |
| JP | 2957218 B2 | 10/1999 |
| JP | 2000199791 A | 7/2000 |
| JP | 2000342547 A | 12/2000 |
| JP | 3096467 U | 9/2003 |
| JP | 3096468 U | 9/2003 |
| JP | 2003275192 A | 9/2003 |
| JP | 2004174179 A | 6/2004 |
| JP | 2005146499 A | 6/2005 |
| JP | 2006188772 A | 7/2006 |
| JP | 2007219894 A | 8/2007 |
| JP | 2007222276 A | 9/2007 |
| JP | 2007279020 A | 10/2007 |
| JP | 200879676 A | 4/2008 |
| JP | 2008188215 A | 8/2008 |
| JP | 2008194186 A | 8/2008 |
| JP | 2008531215 A | 8/2008 |
| JP | 2009028225 A | 2/2009 |
| JP | 2009172182 A | 8/2009 |
| JP | 2009539541 A | 11/2009 |
| JP | 4763392 B2 | 8/2011 |
| JP | 2013503327 A | 1/2013 |
| JP | 2013143997 A | 7/2013 |
| JP | 2013544140 A | 12/2013 |
| JP | 2016529676 A | 9/2016 |
| JP | 2017506376 A | 3/2017 |
| KR | 19980066928 U | 12/1998 |
| KR | 200167069 Y1 | 2/2000 |
| KR | 20000034322 A | 6/2000 |
| KR | 200248697 Y1 | 11/2001 |
| KR | 200417885 Y1 | 3/2006 |
| KR | 20090027200 A | 3/2009 |
| KR | 100912086 B1 | 8/2009 |
| KR | 20100091592 A | 8/2010 |
| KR | 20120008484 U | 12/2012 |
| KR | 20130111570 A | 10/2013 |
| KR | 20130126760 A | 11/2013 |
| KR | 20130137507 A | 12/2013 |
| KR | 20140024845 A | 3/2014 |
| KR | 20140073448 A | 6/2014 |
| KR | 20150007586 A | 1/2015 |
| KR | 20150076233 A | 7/2015 |
| KR | 20160036602 A | 4/2016 |
| KR | 101653119 B1 | 8/2016 |
| KR | 102083685 B1 | 3/2020 |
| SG | 168794 B | 8/2013 |
| WO | 1991010175 A1 | 7/1991 |
| WO | 2000064338 A2 | 11/2000 |
| WO | 2001017421 A1 | 3/2001 |
| WO | 2004078028 A2 | 9/2004 |
| WO | 2004088437 A2 | 10/2004 |
| WO | 2006060949 A1 | 6/2006 |
| WO | 2006097012 A1 | 9/2006 |
| WO | 2007064654 A1 | 6/2007 |
| WO | 2009079461 A | 6/2009 |
| WO | 2009124076 A1 | 10/2009 |
| WO | 2010053617 A3 | 7/2010 |
| WO | 2010120945 A1 | 10/2010 |
| WO | 2011053235 A1 | 5/2011 |
| WO | 2011094876 A1 | 8/2011 |
| WO | 2011132009 A2 | 10/2011 |
| WO | 2012024889 A1 | 3/2012 |
| WO | 2012076225 A1 | 6/2012 |
| WO | 2012100090 A3 | 9/2012 |
| WO | 2012103273 A3 | 10/2012 |
| WO | 2012170110 A1 | 12/2012 |
| WO | 2012170366 A1 | 12/2012 |
| WO | 2013024058 A1 | 2/2013 |
| WO | 2013030744 A1 | 3/2013 |
| WO | 2013093638 A2 | 6/2013 |
| WO | 2013104629 A1 | 7/2013 |
| WO | 2013148753 A1 | 10/2013 |
| WO | 2013163326 A1 | 10/2013 |
| WO | 2013177323 A1 | 11/2013 |
| WO | 2014039567 A1 | 3/2014 |
| WO | 2014060642 A1 | 4/2014 |
| WO | 2014070560 A1 | 5/2014 |
| WO | 2014081184 A1 | 5/2014 |
| WO | 2014145942 A2 | 9/2014 |
| WO | 2014165049 A1 | 10/2014 |
| WO | 2014178793 A1 | 11/2014 |
| WO | 2015001434 A1 | 1/2015 |
| WO | 2015013931 A1 | 2/2015 |
| WO | 2015013933 A1 | 2/2015 |
| WO | 2015051013 A1 | 4/2015 |
| WO | 2015065516 A1 | 5/2015 |
| WO | 2015076861 A1 | 5/2015 |
| WO | 2015081321 A1 | 6/2015 |
| WO | 2015081299 A3 | 10/2015 |
| WO | 2015183773 A1 | 12/2015 |

OTHER PUBLICATIONS

Kevin K. Tremper et al., Pulse Oximetry, 70 Journal of American Society of Anesthesiologists, Inc. (Jan. 1989) ("Tremper").

Y. Mendelson et al., A Wearable Reflectance Pulse Oximeter for Remote Physiological Monitoring, Proceedings of 28th IEEE EMBS Annual International Conference (Aug. 30-Sep. 3, 2006) ("Mendelson 2006").

Sokwoo Rhee et al., Artifact-Resistant, Power-Efficient Design of Finger-Ring Plethysmographic Sensors Part I: Design and Analysis, IEEE (2000) ("Rhee 2000 Part I ").

Sokwoo Rhee et al., Artifact-Resistant, Power-Efficient Design of Finger-Ring Plethysmographic Sensors Part II: Prototyping and Benchmarking, IEEE Proceedings of 22nd Annual EMBS Int'l Conference (Jul. 23-28, 2000) ("Rhee 2000 Part II").

Sokwoo Rhee et al., Artifact-Resistant Power-Efficient Design of Finger-Ring Plethysmographic Sensors, 48 IEEE Transactions of Biomedical Engineering (Jul. 2001) ("Rhee 2001").

Sokwoo Rhee, Design and Analysis of Artifact-Resistive Finger Photoplethysmographic Sensors for Vital Sign Monitoring, MIT (Jun. 2000) ("Rhee Thesis 2000").

C.T. Olofson et al., Machining of Titanium Alloys (1965) ("Olofson").

H. Harry Asada et al., Mobile Monitoring with Wearable Photoplethysmographic Biosensors, IEEE Engineering in Medicine & Biology Magazine 28 (May-Jun. 2003) ("Asada 2003").

Denisse Castaneda et al., A review on wearable photoplethysmography sensors and their potential future applications in health care, Int J Biosens Bioelectron (2018).

Guidelines to Enhancing the Heart-Rate Monitoring Performance of Biosensing Wearables (2014).

Tom Lister et al., Optical Properties of human skin, Journal of Biomedical Optics (2012).

John G. Webster, Design of Pulse Oximeters, CRC Press (1997).

Lawrence K. Au et al., Episodic Sampling: Towards Energy-Efficient Patient Monitoring with Wearable Sensors, Annual International Conference of the IEEE Engineering in Medicine and Biology Society (2009).

(56) References Cited

OTHER PUBLICATIONS

Anastasios Petropoulos et al., Flexible PCB-MEMS flow sensor, Procedia Engineering 47 236-239 (2012) ("Petropoulos").
Tianjia Sun et al., Wireless Power Transfer for Medical Microsystems, Springer (2013) ("Sun").
H. Ardebili and Michael G. Pecht, Encapsulation Technologies for Electronic Applications, William Andrew (2009) ("Ardebili").
Ciprian Ciofu et al., Injection and Micro Injection of Polymeric Plastics Materials: A Review, Int'l J. Modern Mfg. Techs. 49 (2013).
Richard J. Ross, LCP Injection Molded Packages—Keys to JEDEC 1 Performance, IEEE, 2004 Electronic Components and Technology Conference 1807 (2004).
Tadamoto Sakai, Encapsulation Process for Electronic Devices Using Injection Molding Method, 12 Advances in Polymer Technology 61 (1993).
N.J. Teh et al., Embedding of Electronics within Thermoplastic Polymers using Injection Moulding Technique, IEEE, 2000 Int'l Electronics Manufacturing Technology Symposium 10 (2000).
Alexander Silverman, Fifty Years of Glass-Making, 18 Indus. & Eng'g Chem. 896-899 (1926).
B.A.J. Clark, Color in Sunglass Lenses, 46 Optometry & Vision Sci. 825-840 (1969).
Frank Kaltenbach ed., Translucent Materials, Institut fur Internationale Architektur-Dokumentation GmbH & Co. KG (2004).
Takashi Uchino et al., Prediction of optical properties of commercial soda-lime-silicate glasses containing iron, 261 Journal of Non-Crystalline Solids 72-78, 1-3 (2000).
Chao Chen and Carlos Pomalaza-Raez, Monitoring Human Movements at Home Using Wearable Wireless Sensors, Proceedings of ISMICT (2009) ("Chen 2").
Christoph Amma et al., Airwriting Recognition Using Wearable Motion Sensors, Proceedings of Augmented Human Conference (2010) ("Amma").
Yinghui Zhou et al., Analysis and Selection of Features for Gesture Recognition Based on a Micro Wearable Device, Int'l. J. Adv. Comput. Sci. & Appls., vol. 3, No. 1 (2012) ("Zhou").
Taiwoo Park et al., E-Gesture: A Collaborative Architecture for Energy-efficient Gesture Recognition with Hand-worn Sensor and Mobile Devices, SenSys '11 (2011) ("Park").
Jun Rekimoto, GestureWrist and GesturePad: Unobtrusive Wearable Interaction Devices, Proc. 5th Int'l. Symposium on Wearable Computs. (2001) ("Rekimoto").
H. Ying et al., Automatic Step Detection in the Accelerometer Signal, 4th Int'l. Workshop on Wearable and Implantable body Sensor Networks, Springer (2007) ("Ying").
Chun Zhu and Weihua Sheng, Wearable Sensor-Based Hand Gesture and Daily Activity Recognition for Robot-Assisted Living, IEEE Trans. Sys., Man, and Cybernetics, vol. 41, No. 3 (May 2011) ("Zhu").
Jiayang Liu et al., uWave: Accelerometer-based Personalized Gesture Recognition and Its Applications, IEEE Int. Conference on Pervasive Comput. and Commc'ns (2009) ("Liu").
Thomas Schlömer et al., Gesture Recognition With a Wii Controller, Proceedings 2d Int'l. Conf. Tangible & Embedded Interaction (2008) ("Schlömer").
Mohamed Fezari, Microcontroller Based Heart Rate Monitor, The International Arab Journal of Information Technology, 2008, vol. 5, No. 4.
Kevin P. Murphy, Machine Learning: A Probabilistic Perspective, The MIT Press (2012) ("Murphy").
Paulo Trigueiros et al., A Comparison of Machine Learning Algorithms Applied to Hand Gesture Recognition, 7th Iberian Conf. Inf. Syst. & Techs. (2012) ("Trigueiros").
Declaration of Dr. Andrew Wolfe for U.S. Pat. No. 10,842,429.
Daniel Siewiorek, Wearable Computing: Retrospectives on the first decade, GetMobile: Mobile Computing and Communications, vol. 21, Issue 1, 5-10 (Carla Schlatter Ellis ed., Mar. 2017).
David M. Ewalt, Getting Fitbit, Forbes (Jun. 11, 2010), https://www.forbes.com/2010/06/11/fitbit-tracker-pedometerlifestyle-heatlh-lifetracking.html.

Brian Santo, The Consumer Electronics Hall of Fame: Fitbit, IEEE Spectrum (Nov. 7, 2019), https://spectrum.ieee.org/the-consumerelectronics-hall-of-fame-fitbit.
Boo-Ho Yang, A twenty-four hour tele-nursing system using a ring sensor, 1998 IEEE International Conference on Robotics and Automation, 1998, vol. 1, p. 387-392., vol. 1.
Sokwoo Rhee, The ring sensor: a new ambulatory wearable sensor for twenty-four hour patient monitoring, Biology Society. vol. 20 Biomedical Engineering Towards the Year 2000 and Beyond, 1998, vol. 4, p. 1906-1909 vol.4.
Russell Paul Dresher, Wearable Forehead Pulse Oximetry: Minimization of Motion and Pressure Artifacts, Masters Theses Worcester Polytechnic Institute (All Theses, All Years). 660, 2006, https://digitalcommons.wpi.edu/etd-theses/660.
Emre Ertin, AutoSense: Unobtrusively Wearable Sensor Suite for Inferring the Onset, Causality, and Consequences of Stress in the Field, SenSys 2011—Proceedings of the 9th ACM Conference on Embedded Networked Sensor Systems, 2011, p. 274-287.
Declaration of Dr. Brian W. Anthony for U.S. Pat. No. 9,582,034.
Declaration of Dr. Brian W. Anthony for U.S. Pat. No. 10,139,859.
Declaration of Dr. Brian W. Anthony for U.S. Pat. No. 10,281,953.
Declaration of Dr. Brian W. Anthony for U.S. Pat. No. 10,893,833.
Declaration of Dr. Brian W. Anthony for U.S. Pat. No. 11,599,147.
Declaration of Dr. Brian W. Anthony for U.S. Pat. No. 11,868,178.
Declaration of Dr. Brian W. Anthony for U.S. Pat. No. 11,868,179.
Declaration of Dr. Brian W. Anthony for U.S. Pat. No. 11,874,701.
Declaration of Dr. Brian W. Anthony for U.S. Pat. No. 11,874,702.
Boo-Ho Yang et al. "Development of the Ring Sensor for Healthcare Automation" Robotics and Autonomous Systems (May 21, 1999).
K. Hung et al. "Wearable Medical Devices for Tele-Home Healthcare" Jont Research Center for Biomedical Engineering—Department of Electronic Engineering.
Peter T. Gibbs et al., "Active Motion Artifact Cancellation for Wearable Health Monitoring Sensors Using Collocated MEMS Accelerometers" Massachusetts Institute of Technologys.
J. Sola et al., "SpO2 Sensor Embedded in a Finger Ring: Design and Implementation" Proceedings of the 28th IEEE, EMBS Annual International Conference, New York City, Aug. 30-Sep. 3, 2006.
H. Harry Asada et al. "Wearable Sensors for Human Health Monitoring" Proc. of SPIE vol. 6174.
Lithium Ion Curved Batteries Curved LiPo 201030.
H. Harry Asada, Mobile monitoring with wearable photoplethysmographic biosensors, IEEE Engineering in Medicine and Biology Magazine, May 2004, vol. 22 (3), p. 28-40; H. Harry Asada.
Yu-Chi Wu, A Mobile Health Monitoring System Using RFID Ring-Type Pulse Sensor, 2009 Eighth IEEE International Conference on Dependable, Autonomic and Secure Computing, 2009, p. 317-322.
Yu-Chi Wu et al., A Mobile-Phone-Based Health Management System, Health Management—Different Approaches and Solutions, 2011, p. 21-40.
Lester, Jonathan, et al., A Hybrid Discriminative Generative Approach for Modeling Human Activities, 2005.
Rennie, K, et al., A combined heart rate and movement sensor: proof of concept and preliminary testing study, European Journal of Clinical Nutrition, 2000, vol. 54, pp. 409-414.
Jones, Alice Yee-Men, PhD, et al., Activity Levels and Resting Energy Expenditure in an Elderly Population: A Pilot Study, Hong Kong Physiotherapy Journal, 2004, vol. 22, pp. 29-32.
Ohtaki, Yasuaki, et al., Automatic classification of ambulatory movements and evaluation of energy consumptions utilizing accelerometers and a barometer, Microsyst Technol, 2005, vol. 11, pp. 1034-1040.
Firstbeat Technologies, Ltd., Heart Beat Based Recovery Analysis for Athletic Training, Published: Mar. 2009, Last Update: Mar. 2012. pp. 1-5.
Firstbeat Technologies, Ltd., Stress and Recovery Analysis Method Based on 24-hour Heart Rate Variability, Published: Sep. 16, 2014, updated: Apr. 11, 2014. pp. 1-13.
Mamiit, Aaron, CES 2015: The 'Ring' to Control Them All? How Logbar Gesture Control Ring Works, Published Jan. 7, 2015, 8:39 AM EST, TechTimes.com.

(56) References Cited

OTHER PUBLICATIONS

Livingstone, M. Barbara E. et al., Simultaneous measurement of free-living expenditure by the doubly labeled water method and heart-rate monitoring, The American Journal of Clinical Nutrition, 1990, vol. 52, pp. 59-65.

Appelboom, Geoff, et al., Smart wearable body sensors for patient self-assessment and monitoring, Archives of Public Health, 2014, vol. 72:28, pp. 1-9.

Ceesay, Sana M., et al., The use of heart rate monitoring in the estimation of energy expenditure: a validation study using indirect whole-body calorimetry, British Journal of Nutrition, 1989, vol. 61, pp. 175-186.

Hung, K., et al., Wearable Medical Devices for Tele-Home Healthcare, Proceedings of the 26th Annual International Conference of the IEEE EMBS San Francisco, CA, USA, Sep. 1-5, 2004, pp. 5384-5387.

Whoop 2014 Video, 2014, https://web.archive.org/web/20141026044619/http://whoop.com:80/.

Hoyt, Reed W., Jaques Reifman, Trinka S. Coster, and Mark J. Buller. "Combat Medical Informatics: Present and Future." AMIA 2002 Annual Symposium Proceedings.

Buchheit, Martin. "Monitoring training status with HR measures: do all roads lead to Rome?" 5 Frontiers in Physiology 73.

Bunn, Jennifer A., James W. Navalta, Charles J. Fountaine, and Joel D. Reece. "Current State of Commercial Wearable Technology in Physical Activity Monitoring 2015-2017." International Journal of Exercise Science 11(7): 503-515.

Kiviniemi, Antti M., Arto J. Hautala, Hannu Kinnunen, and Mikko P. Tulppo. "Endurance training guided individually by daily heart rate variability measurements." 101 Eur. J. Appl. Physiol. 743-751.

Kiviniemi, Antti M., Arto J. Hautala, Hannu Kinnunen, Juuso Nissilä, Paula Virtanen, Jaana Karjalainen, and Mikko P. Tulppo. "Daily Exercise Prescription on the Basis of HR Variability among Men and Women." 42(7) Medicine and Science in Sports and Exercise 1355-1363.

Fogt, Donovan L., Page J. Cooper, Christine N. Freeman, John E. Kalns, and William H. Cooke. "Heart Rate Variability to Assess Combat Readiness." 174(5) Military Medicine 491.

Garber, Carol Ewing, Bryan Blissmer, Michael R. Deschenes, Barry A. Franklin, Michael J. Lamonte, I-Min Lee, David C. Nieman, and David P. Swain. "Quantity and Quality of Exercise for Developing and Maintaining Cardiorespiratory, Musculoskeletal, and Neuromotor Fitness in Apparently Healthy Adults: Guidance for Prescribing Exercise." Medicine and Science in Sports and Exercise 1334-1359.

Savell, C. Thomas, Maurizio Borsotto, Jaques Reifman, and Reed W. Hoyt. "Life Sign Decision Support Algorithms." IMIA Medinfo 2004 1453-1458.

Samedayflash, "Set of 10 2GB/4GB/8GB/16GB Wooden Bamboo Flash Drive—Bulk Pack O USB 2.0 Wood Bamboo Stick Design—Wood USB Flash Drive, www.etsy.com/listing/248051205/set-of-10-2gb4gb8gb16gb-wooden-bamboo?ref+m", Jun. 2, 2016, Publisher: Etsy, Published in: US.

Medical Mood Ring—Anonymous—Technology Review; Apr. 2004; 107, 3; ProQuest p. 18.

Pingu: Another User-friendly Interface Device: Multi-sensor Based Gestural Interaction for Smart Home Environments; Department of Signal and Systems; Communication Systems Group; Chalmers University of Technology; Göteborg, Sweden, 2012; Report No. EX070/2012.

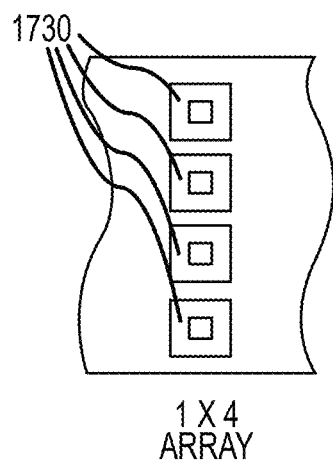
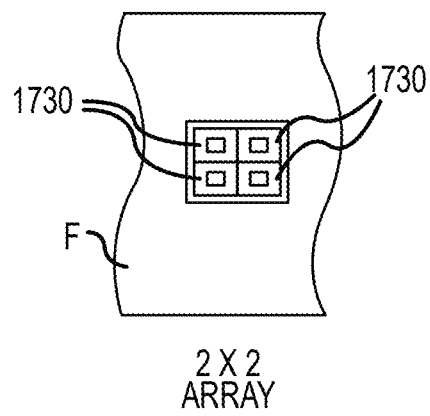
1 X 4 ARRAY
FIG.17E
2 X 2 ARRAY
FIG.17F
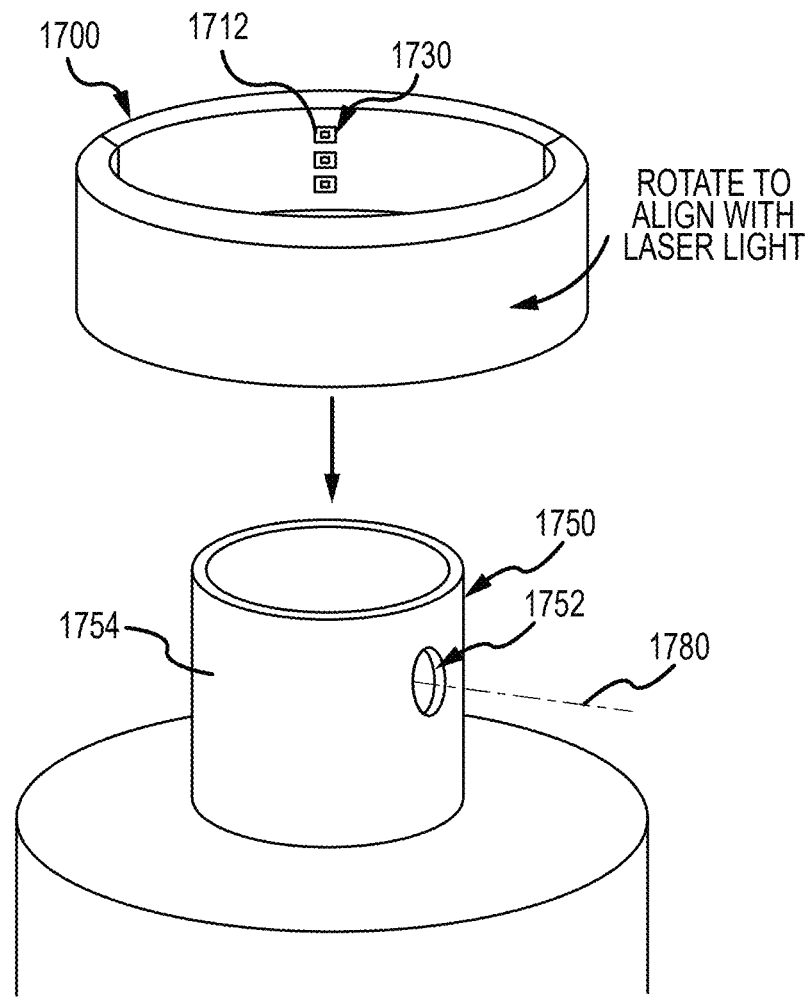
FIG.17G

* SYSTEM WILL ONLY MATCH TO A SUBSET OF THE TOTAL SCANNED AREA

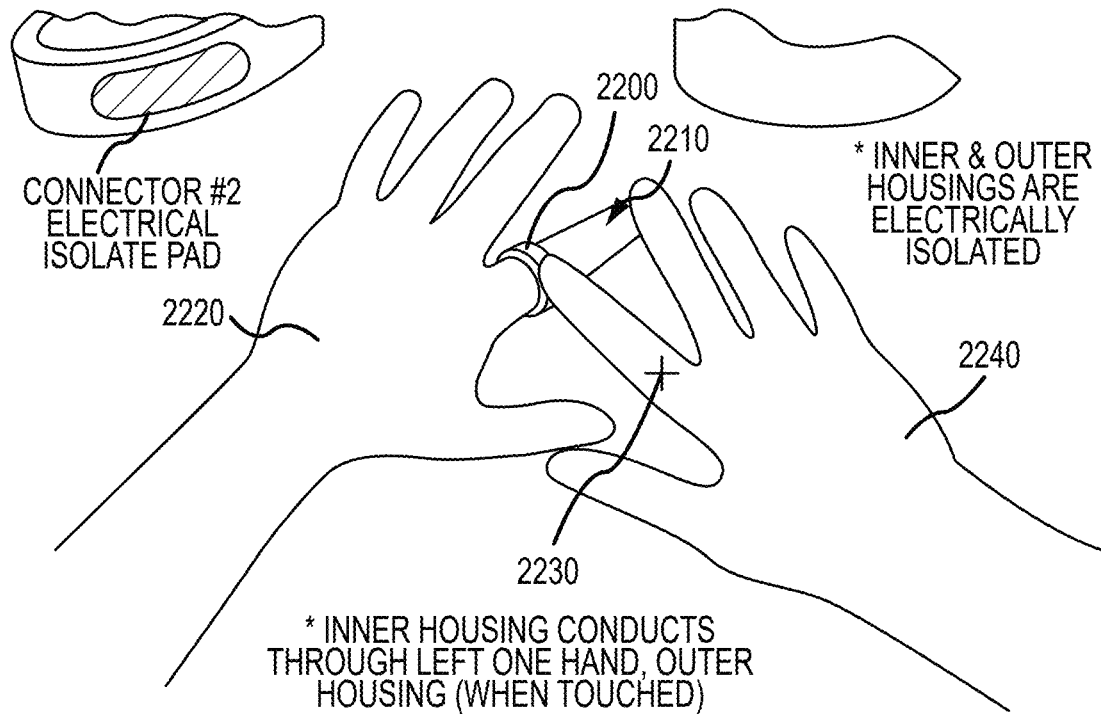
FIG.22A
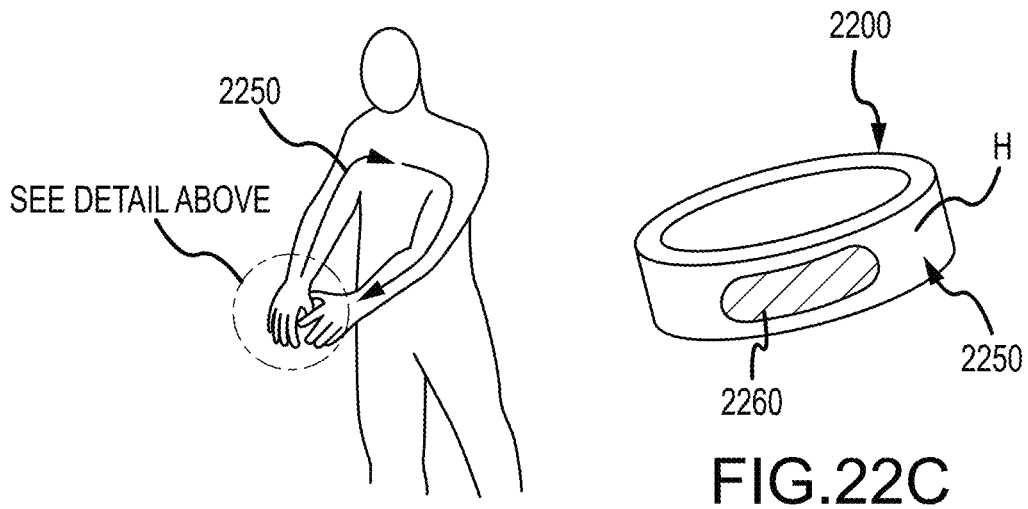
FIG.22B
FIG.22C

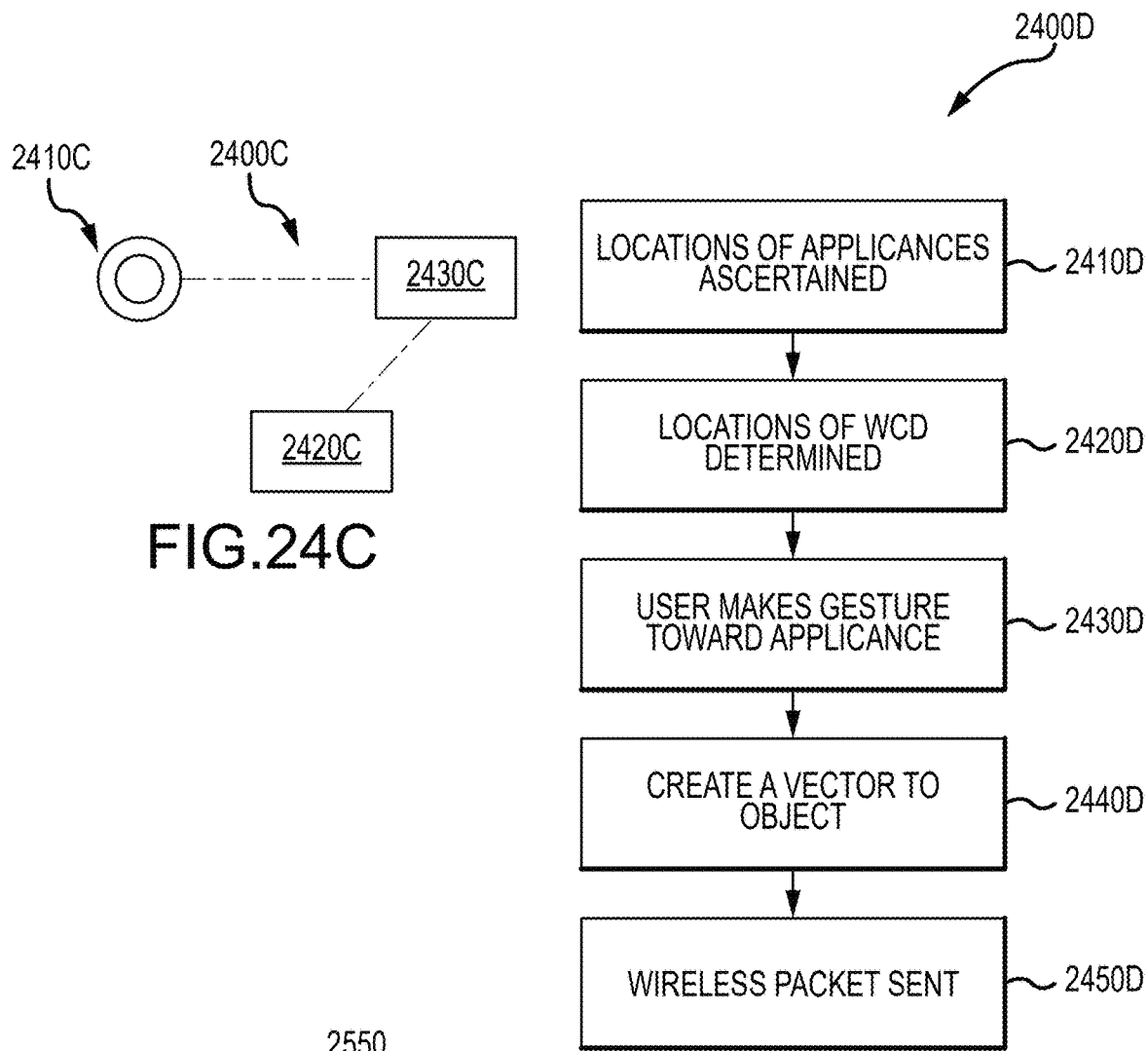

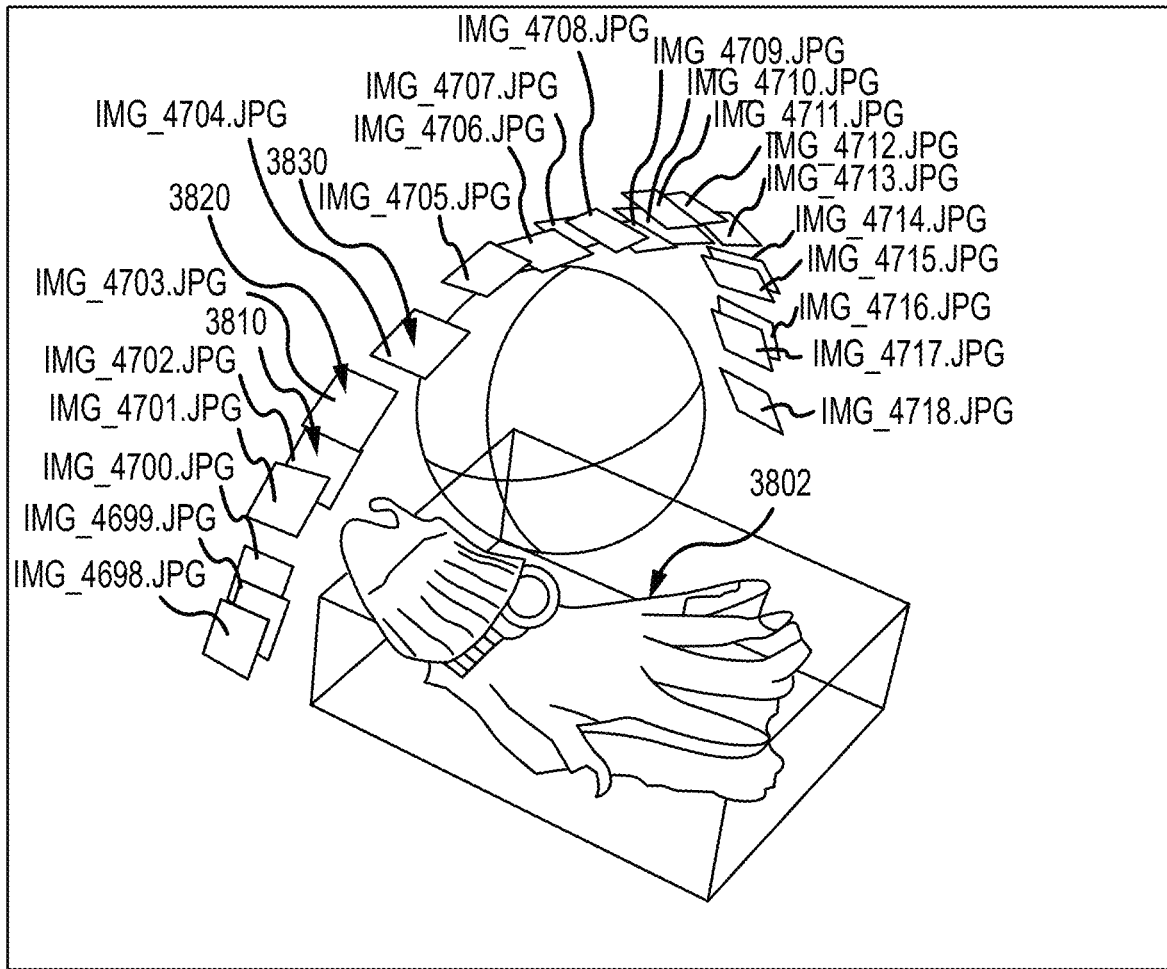
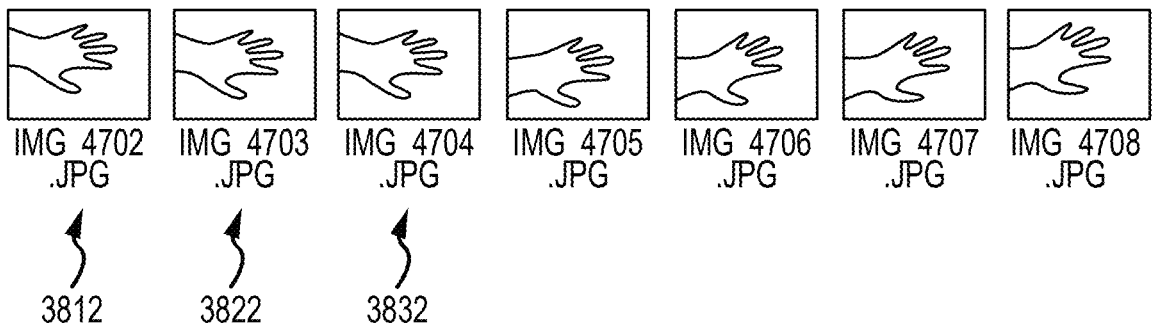
FIG.38

WEARABLE COMPUTING DEVICE

CROSS REFERENCE

The present Application for Patent is a Continuation of U.S. patent application Ser. No. 18/323,387, by von Badinski et al., entitled "WEARABLE COMPUTING DEVICE," filed May 24, 2023, which is a Continuation of U.S. patent application Ser. No. 18/179,272, by von Badinski et al., entitled "WEARABLE COMPUTING DEVICE," filed Mar. 6, 2023, which is a Continuation of U.S. patent application Ser. No. 17/519,201, by von Badinski et al., entitled "WEARABLE COMPUTING DEVICE," filed Nov. 4, 2021, which is a Continuation of U.S. patent application Ser. No. 17/013,348, by von Badinski et al., entitled "WEARABLE COMPUTING DEVICE," filed Sep. 4, 2020, which is a Continuation of U.S. patent application Ser. No. 16/224,686, by von Badinski et al, entitled "WEARABLE COMPUTING DEVICE," filed Dec. 18, 2018, which is a Division of U.S. patent application Ser. No. 15/444,217, by von Badinski et al., entitled "WEARABLE COMPUTING DEVICE," filed Feb. 27, 2017, which is a Division of U.S. patent application Ser. No. 14/556,062, by von Badinski et al, entitled "WEARABLE COMPUTING DEVICE," filed Nov. 28, 2014, which claims the benefit of U.S. Provisional Application Ser. No. 62/006,835, by von Badinski et al., entitled "WEARABLE COMPUTING DEVICE," filed Jun. 2, 2014, and U.S. Provisional Application Ser. No. 61/910,201, by von Badinski et al., entitled "FINGER RING DEVICE FOR ACTIVITY MONITORING OR GESTURAL INPUT," filed Nov. 29, 2013, each of which is expressly incorporated by reference herein.

FIELD OF TECHNOLOGY

This invention is in the field of wearable electronic devices.

BACKGROUND

Wearable electronics are an emerging technology with many applications for the wearer. They can improve lifestyles, ease access to technology and help monitor activity within the wearer's body. However, many current wearable electronics are bulky and can be intrusive or interfere with a person's daily life. In this regard, the wearer may not be comfortable wearing the device for extended periods of time.

SUMMARY OF THE INVENTION

This invention overcomes the disadvantages of the prior art by providing a wearable computing device (WCD) in the shape of a ring. The wearable computing device can be worn for extended periods of time and can take many measurements and perform various functions because of its form factor and position on the finger of a user.

One aspect of the disclosure provides a wearable computing device, comprising: an interior wall; an exterior wall; a flexible printed circuit board disposed between the interior wall and the exterior wall; at least one component disposed on the flexible printed circuit board; and wherein at least one of the interior wall and the exterior wall defines a window that facilitates at least one of data transmission, battery recharge, and status indication.

In one example, the window comprises an internal window defined by the interior wall.

In one example, the window comprises an exterior window defined by the exterior wall.

In one example, the window comprises a plurality of exterior windows defined by the exterior wall.

In one example, the plurality of exterior windows comprises a first exterior window and a second exterior window, wherein the first exterior window facilities battery charging and the second exterior window facilities data transmission.

In one example, at least one concentrated photovoltaic cell, an antenna, and at least one LED are accessible via the window.

Another aspect of the disclosure provides a wearable computing device, comprising: an internal housing portion configured to be disposed near a finger of a user; a flexible printed circuit board arranged around a portion of a circumference of an interior surface of the internal housing; at least one component disposed on the flexible printed circuit board; and an external housing portion configured to seal the at least one component and the printed circuit board in an internal space defined by the interior surface of the internal housing.

In one example, the external housing portion comprises a substantially transparent external potting.

In one example, the at least one component comprises at least one LED configured to emit at least one of visible light, infrared radiation, and ultraviolet radiation through the external potting.

In one example, the at least one component comprises a concentrated photovoltaic cell configured to receive concentrated light through the transparent external potting.

In one example, the flexible printed circuit board includes a plurality of stiffener elements configured to engage with a corresponding plurality of flanges disposed on the internal housing portion.

Another aspect of the disclosure provides a wearable computing device, comprising: an external housing portion; a flexible printed circuit board arranged around a portion of a circumference of an interior surface of the external housing; at least one component disposed on the flexible printed circuit board; and an internal housing portion configured to seal the at least one component and the printed circuit board in an internal space defined by the interior surface of the external housing.

In one example, the internal housing portion comprises a substantially transparent internal potting.

In one example, the at least one component comprises at least one LED configured to emit at least one of visible light, infrared radiation, and ultraviolet radiation through the internal potting.

In one example, the at least one component comprises a concentrated photovoltaic cell configured to receive concentrated light through the transparent internal potting.

In one example, the flexible printed circuit board includes a plurality of stiffener elements configured to engage with a corresponding plurality of flanges disposed on the external housing portion.

Another aspect of the disclosure provides a system, comprising: a wearable computing device, including a housing and a photovoltaic element disposed at least partially within the housing; and a base assembly, the base assembly including a concentrated light source directed at the photovoltaic element.

In one example, the wearable computing device includes at least one ferrous element disposed within the housing, and wherein the base assembly includes at least one magnetic element disposed therein.

In one example, the concentrated light source is arranged circumferentially around the wearable computing device when the wearable computing device is engaged with the base assembly.

In one example, the concentrated light source comprises at least one of a laser diode and a light emitting diode (LED).

In one example, a housing of the WCD defines an opening through which the WCD is configured to receive concentrated light.

In one example, the base assembly comprises an optical element for focusing concentrated light emitted from the concentrated light source.

In one example, the optical element comprises a lens and is selected from the group consisting of concave, convex, piano-concave, piano-convex.

In one example, the WCD comprises at least one transparent potting configured to allow concentrated light to pass therethrough.

In one example, the WCD is ring-shaped and the base assembly comprises at least one post configured to engaged with a finger space of the WCD.

In one example, the photovoltaic cell comprises a plurality of photovoltaic cells.

Another aspect of the disclosure provides an enclosure for a wearable computing device, the enclosure comprising: a base defining a receptacle for receiving the wearable computing; a lid configured to engage with the base to substantially enclose the wearable computing device, the lid having an optical element configured to direct incident electromagnetic radiation to photovoltaic cell disposed on the wearable computing device to allow charging thereof.

In one example, the lid includes a plurality of vent holes that prevent overheating within the enclosure.

In one example, the optical element comprises a lens.

In one example, the lens has a focal length and wherein a distance between a central portion of the lens and the photovoltaic cell is greater than or less than the focal length.

Another aspect of the disclosure provides a timepiece system, comprising: a timepiece having a substantially planar under surface; and a timepiece computing device adhered to the planar under surface, the timepiece computing device being substantially cylindrical and comprising: a processor; a memory; and at least one sensor.

Another aspect of the disclosure provides a wearable computing device system, comprising: a wearable computing device; an attachment frame coupled to the wearable computing device; and an optical element removably coupled to the attachment frame, wherein the optical element is configured to direct electromagnetic radiation to a photovoltaic cell disposed on a surface of the wearable computing device to allow for charging of the wearable computing device.

In one example, the attachment frame is removably coupled to the wearable computing device.

In one example, the attachment frame engages with an inward-facing surface of the wearable computing device.

Another aspect of the disclosure provides a method of identifying an authorized user of a wearable computing device, comprising: illuminating a portion of a skin surface of the user; imaging the portion of the skin surface of the user to generate at least one first image; generating a reference capillary map corresponding to the user based at least in part on the at least one image.

In one example, the method further includes rotating the wearable computing device during the illuminating and imaging steps.

In one example, the method further includes imaging the portion of the skin surface of the user to generate at least one second image; and comparing the at least one second image to the reference capillary map in order to authenticate the user.

Another aspect of the disclosure provides a method of navigating, comprising: gesturing in a first direction while wearing a wearable computing device; comparing the first direction to a predetermined direction in a predetermined set of directions; providing feedback based on the comparison of the first direction of the predetermined direction.

In one example, the gesture comprises pointing a finger and the first direction comprises a first heading.

Another aspect of the disclosure provides a method of regulating temperature, comprising: measuring a skin temperature of a user via a first temperature sensor; measuring an ambient temperature via a second temperature sensor; comparing the skin temperature to a predetermined threshold temperature; and adjusting the ambient temperature based in part on the comparison.

In one example, measuring the skin temperature comprises measuring the skin temperature via a first temperature sensor disposed at an inward facing surface of a wearable computing device.

In one example, measuring the ambient temperature comprises measuring the ambient temperature via a second temperature sensor disposed at an outward facing surface of the wearable computing device.

Another aspect of the disclosure provides a method for controlling appliances, comprising: identifying a position of a first appliance in a room; gesturing a first gesture in a direction of the first appliance; identifying the direction of the first direction via a wearable computing device; issuing a controlling command to the first appliance based in part on the identified direction of the gesture.

Another aspect of the disclosure provides a method of generating an alert, comprising: authenticating a first wearer of a first wearable computing device as a first authenticated user; transmitting first biometric data associated with the first wearer; associating the first biometric data with a first profile associated with the first wearer of the first wearable computing device; comparing the first biometric data with a group profile comprising aggregated biometric data from a plurality of distinct wearers of a plurality of distinct wearable computing devices; and generating an alert if the first biometric data falls outside of a predetermined threshold set by the aggregated biometric data.

In one example, the biometric data comprises at least one of heart rate; ECG profile; blood sugar, and blood pressure.

In one example, the plurality of distinct wearers share a common trait, resulting in their aggregation into the group profile.

In one example, the common trait comprises at least one of: age, gender, profession, and location.

Another aspect of the disclosure provides a method of determine a sampling rate of a wearable computing device, comprising: determining an activity level of a wearer of a wearable computing device based at least in part on data from at least one sensor disposed onboard the wearable computing device; comparing the activity level to a predetermined activity threshold; and increasing a first sensor sampling rate if the activity level is above a predetermined activity threshold.

In one example, the method further includes decreasing the first sensor sampling rate if the activity level is below a predetermined activity threshold.

In one example, the predetermined activity threshold comprises an acceleration measurement.

BRIEF DESCRIPTION OF THE DRAWINGS

The invention description below refers to the accompanying drawings, of which:

FIGS. 17E-F depict other CPV configurations according to one or more aspects of the disclosure;

FIG. 17G is perspective view of a WCD and base assembly with a 1×3 CPV arrangement;

FIG. 22A is a perspective view of a user employing ECG monitoring according to one or more aspects of the disclosure;

FIG. 22B is a view of a human with an electric pathway though his body according to one or more aspects of the disclosure;

FIG. 22C is a perspective view of a WCD that can employ ECG monitoring according to one aspect of the disclosure;

FIG. 24C is a system diagram of a system for controlling home appliances according to one or more aspects of the disclosure;

FIG. 24D is a flow chart depicting a method of controlling home appliances according to one or more aspects of the disclosure;

FIG. 25 is a perspective view of the hand of a user employing a two-factor authentication technique according to one or more aspects of the disclosure;

FIG. 38 is a pictorial diagram showing a plurality of image perspectives of a user's hand;

DETAILED DESCRIPTION

The present disclosure describes a wearable computing device (WCD) that enables a wearable fitness monitor(s)/computer(s) which is suitable for prolonged usage with accurate results. The WCD can be in the form of a ring that can be worn on the finger of a human (or animal) user. Although the WCD of the present disclosure is depicted as a ring that can be worn on the finger of a user, other shapes, designs, and form factors can be utilized for the WCD. For example, the WCD can be in the form of a wrist band, bracelet, necklace, earring, or any other type of wearable accessory. In this regard, references to the finger of a user in the present application can be considered to apply to other portions of a human body depending on the form of the WCD, such as wrist, neck, ear, etc.

The term "coupled" as used herein means connected directly to or connected through one or more intervening components or circuits. Any of the signals provided over various buses described herein may be time-multiplexed with other signals and provided over one or more common buses. Additionally, the interconnection between circuit elements or software blocks may be shown as buses or as single signal lines. Each of the buses may alternatively be a single signal line, and each of the single signal lines may alternatively be buses, and a single line or bus might represent any one or more of a myriad of physical or logical mechanisms for communication (e.g., a network) between components. The present embodiments are not to be construed as limited to specific examples described herein but rather to include within their scope all embodiments defined by the appended claims.

Figure 1A:
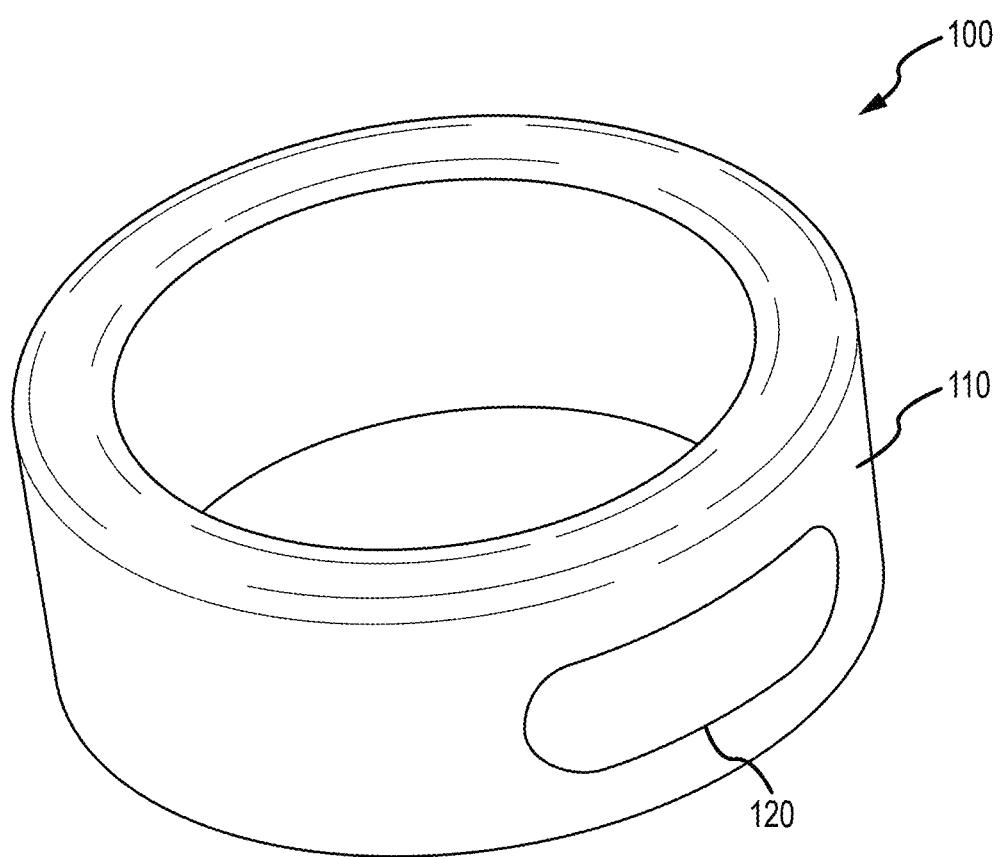
FIG. 1A is a perspective view of a WCD illustrating an exterior window in accordance with some embodiments.
Figure 1B:
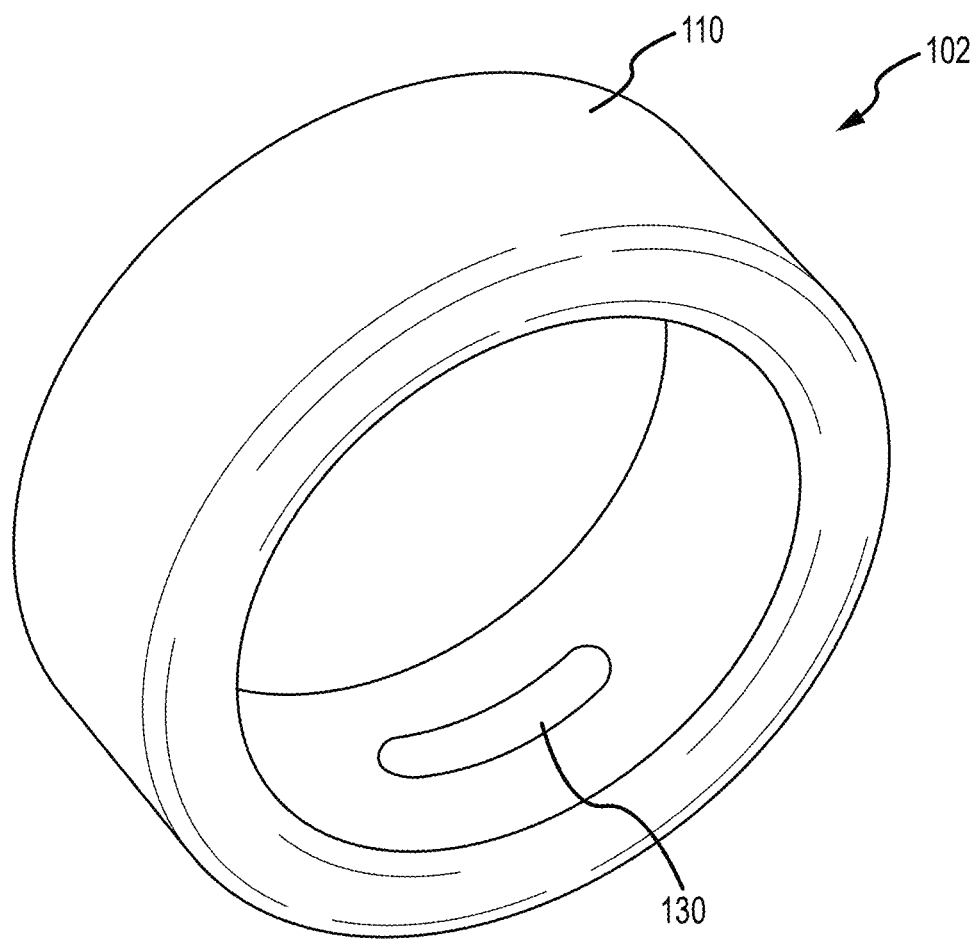
FIG. 1B is a perspective view of the WCD of FIG. 1A illustrating an interior window in accordance with some embodiments.

FIG. 1A is a perspective view of 100 of a WCD 110 illustrating an exterior window 120 in accordance with some embodiments, and FIG. 1B is a perspective view 102 of the WCD 110 of FIG. 1A illustrating an interior window 130.

As previously mentioned, it is recognized in the present disclosure that conventional wearable fitness monitors such as clip-on devices, wristbands, or watch-type monitors still often suffer from inaccuracy mainly because they lack constant and consistent ways to read from the body areas they aim to monitor. It can also be an extra burden for the person to remember and wear such conventional fitness monitors each time the person perform exercises in order to create an accurate history tracking the exercise activities.

Accordingly, the present embodiments of the WCD 110 can function as fitness monitors/computer which is suitable for prolonged usage so as to create accurate results. In addition or as an alternative to fitness monitoring, as will be discussed in more detail below, the WCD 110 can function as a remote input device through, for example, gesture recognition. In some embodiments, the WCD 110 can further function as a sleep monitor, a heart rate sensor, a cardiac monitor a body temperature detector, or the like. It is noted that, for those embodiments which can function as a cardiac monitor (e.g., that measures electrocardiogram (EKG)), it may be necessary to establish a closed loop (e.g., for the electrical measurement of EKG) across the heart. As such, in some of those embodiments, a separate conductive pad can be coupled to the WCD 110 so that a user can pinch the pad with fingers on an opposite hand, Specifically, in some embodiments of the present disclosure, the WCD 110 can be worn by the user (e.g., on a finger) for fitness, physical activity, biological data monitoring as well as for gestural input or other suitable purposes. As shown in FIGS. 1A and 1B, the WCD 110 can include the exterior window 120 on its exterior wall for input/output data transmission and reception, battery recharge, or status indication. The WCD 110 can also include the interior window 130 on its interior wall for various monitoring or sensing activities. The form factor of the WCD 110 allows it to be worn for prolonged hours with constant and consistent contact with the skin area, thereby creating a more reliable and extended recording (e.g., as compared to aforementioned conventional fitness monitors) of the user's fitness activity, physical exercise, as well as health information such as heart rates and body temperature. More implementation details regarding the WCD 110 are discussed below.

Figure 1C:
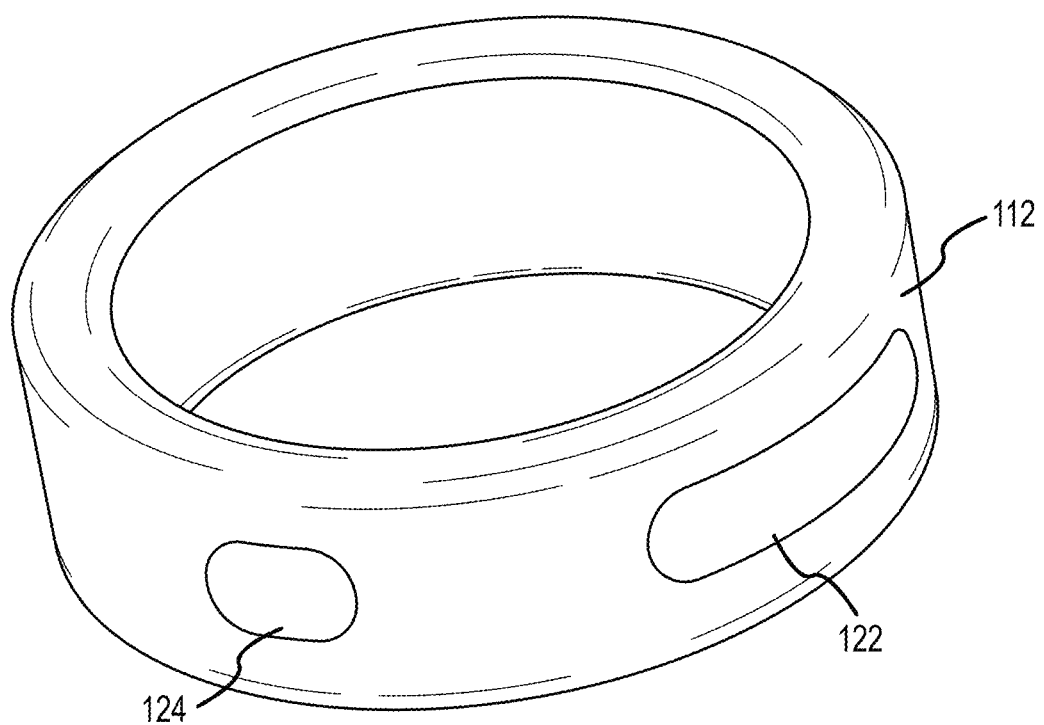
FIG. 1C is a perspective view of an alternative WCD design of the ring of FIG. 1A in accordance with some embodiments.

FIG. 1C is a perspective view of an alternative design of the WCD 110 of FIG. 1A in accordance with some embodiments. As shown in FIG. 1C, the WCD 112 includes a second exterior window 124 in addition to a first exterior window 122. The two exterior windows 122 and 124 can include spacing between the two windows 122 and 124 so that the mechanical strength of the housing structure of the WCD 112 may be stronger than that of the WCD 110, which is shown to include one single exterior window 120. Further, in some embodiments, radio antennas (e.g., Bluetooth) or other sensitive circuitry can be positioned in the second exterior window 124 away from the first exterior window 122 so that quality of reception may be improved.

Figure 2:
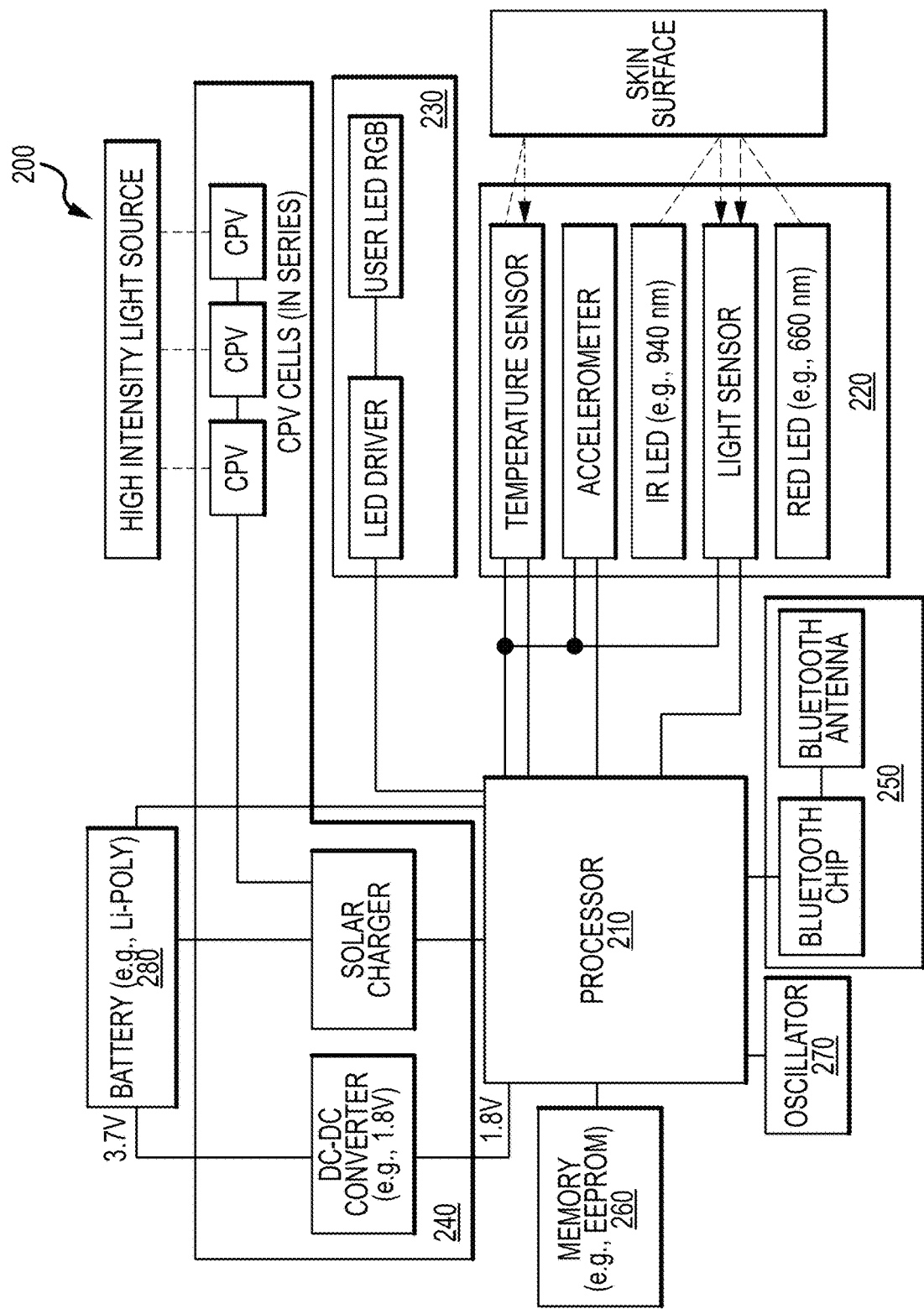
FIG. 2 is an abstract functional diagram illustrating example components within the WCD in accordance with some embodiments.

FIG. 2 is an abstract functional diagram 200 illustrating example components within the WCD (e.g., WCD 110) in accordance with some embodiments. As shown in diagram 200, the WCD 110 can include a processor module 210, a plurality of sensor modules 220, a status indicator module 230, a power generation and management module 240, a communication module 250, a memory 260, and miscellaneous modules 270 (e.g., a real-time clock (RTC) crystal oscillator as illustrated in FIG. 2). The WCD 110 can also include a battery 280 module that provides electrical power for the WCD 110. In some embodiments, the battery 280 can be of a lithium-polymer type or a zinc-polymer type. It is noted that modules illustrated in diagram 200 are for purposes of facilitating a better understanding of the present embodiments; other suitable modules may be included in the WCD 110 and are not shown for simplicity. As used herein, the term "components" is considered to generally include any of the modules depicted and/or described in FIG. 2, as well as any other modules described herein.

It is noted that the aforementioned modules are intended for purposes of enabling the present embodiments, rather than limiting. As such, a person of ordinary skill in the art will understand that the present disclosure covers apparent alternatives, modifications, and equivalents (e.g., combining or separating the modules) made to the techniques described herein. For example, in some embodiments, a portion of the communication module 250 (e.g., the Bluetooth Chip as shown in FIG. 2) can be combined into the processor module 210. For another example, one or more modules herein can be combined into one to form a system-on-the-chip (SOC).

The processor module 210 can have generic characteristics similar to general purpose processors or may be application specific integrated circuitry that provides arithmetic and control functions to the WCD 110. The processor can be any type of processor, such as a processor manufactured by AMtel, Freescale, Nordic Semiconductor, Intel®, AMD®, or an ARM® type processor. The processor module 210 can include a dedicated cache memory (not shown for simplicity). The processor module 210 is coupled to all modules 220-270 in the WCD 110, either directly or indirectly, for data and control signal transmission.

The memory 260 may include any suitable type of storage device including, for example, ROM, such as Mask ROM, PROM, EPROM, EEPROM; NVRAM, such as Flash memory; Early stage NVRAM, such as nvSRAM, FeRAM, MRAM, or PRAM, or any other type, such as, CBRAM, SONOS, RRAM, Racetrack memory, NRAM, Millipede memory, or FJG. Other types of data memory can be employed as such are available in the form factor desired.

In addition to storing instructions which can be executed by the processor module 210, the memory 260 can also store data generated from the processor module 210. It is noted that the memory 260 can be an abstract representation of a generic storage environment. According to some embodiments, the memory 260 may be comprised of one or more actual memory chips or modules. In some embodiments, the memory 260 can function as a temporary storage (e.g., for firmware updates, and/or for avoiding accidental malfunctions (such as so-called "bricking")).

Figure 3A:
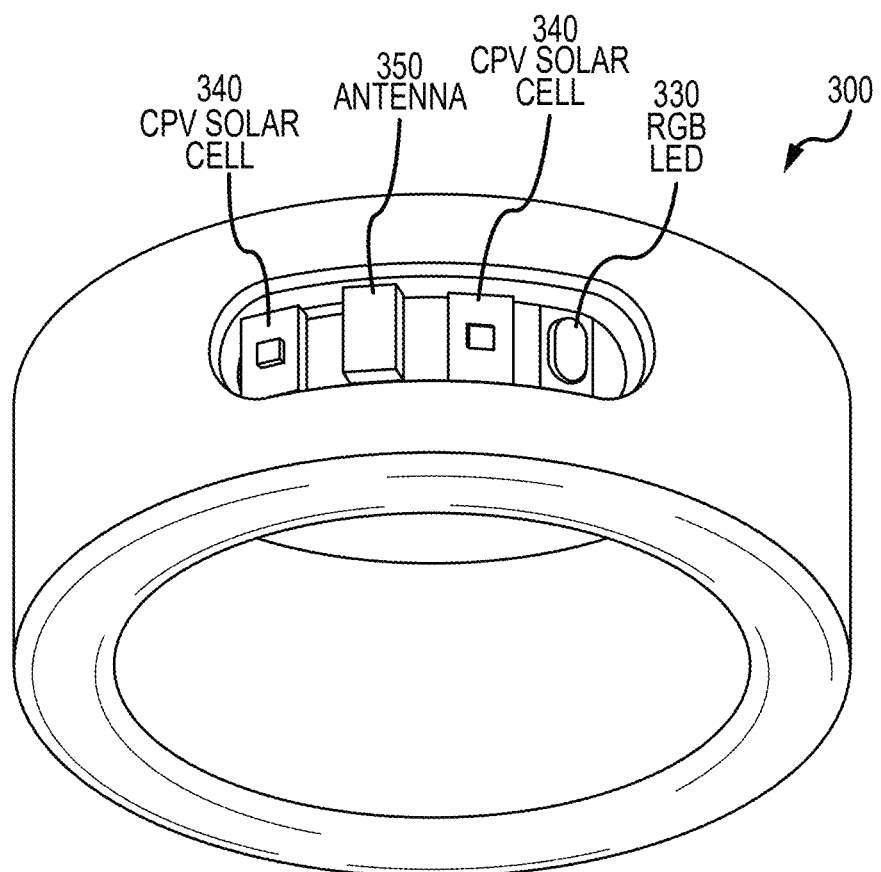
FIG. 3A is a view of an exterior window of a WCD with example components exposed in accordance with some embodiments.
Figure 3B:
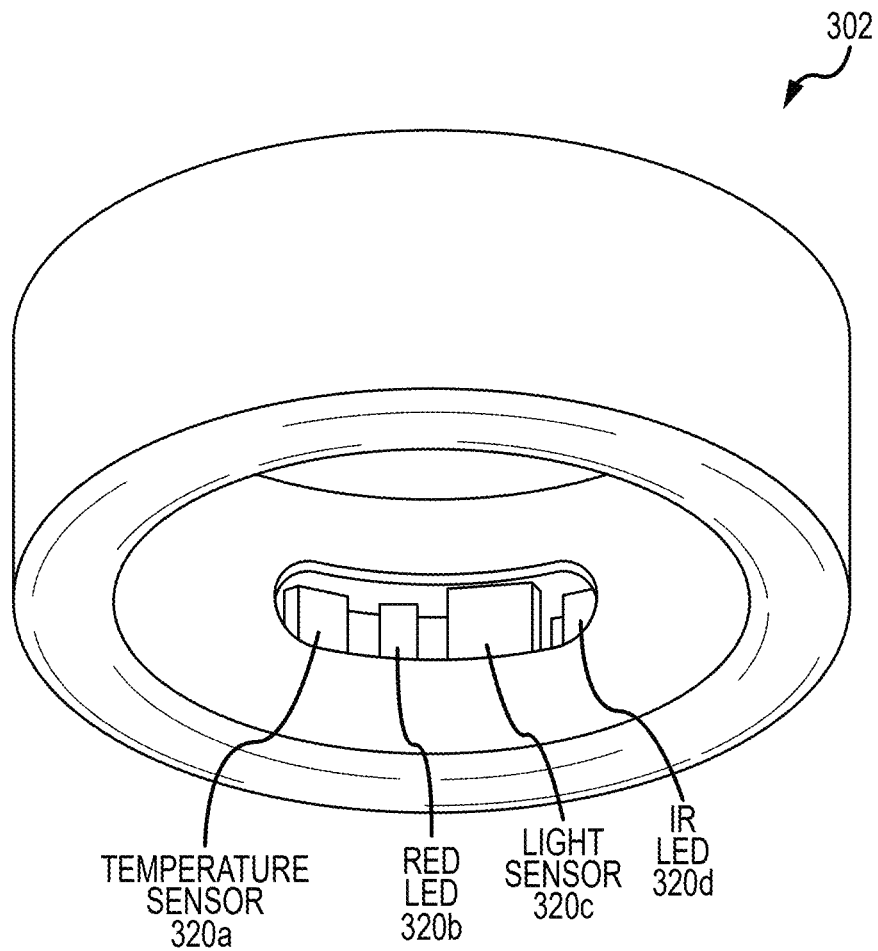
FIG. 3B is a view of an interior window of a WCD with example components exposed in accordance with some embodiments.

In accordance with one or more embodiments, the sensor modules 220 can include various sub-modules for the WCD 110 to perform different monitoring or sensing activities. A view 302 of the interior window (e.g., window 130) of a WCD (e.g., WCD 110) with example components exposed is shown in FIG. 3B. As shown in the example of FIG. 3B, the sensor modules 220 can include a temperature sensor 320a, a red light emitting diode (LED) 320b, a light sensor 320c, and an infra-red LED 320d. Among the sensors in the sensor modules 220, those sensors (e.g., sensors 320a-320d) which are directly related to biological sign monitoring can be configured and positioned in a way that is close to the skin (e.g., facing the interior window 130 of the WCD 110). Although not shown in FIG. 3B for simplicity, the sensor modules 220 can further include sensors that are not directly related to biological sign monitoring; some examples of these sensors include accelerometers, gyroscopes, vibration, sensors (e.g., a magnetometer or a digital compass), or other suitable sensors (e.g., for gesture recognition). The magnetometer can measure the strength and/or direction of a prevailing magnetic field. In this regard, the magnetometer can be used during global positioning and/or navigation. In particular, the magnetometer can be used to measure a directional heading when the WCD is in motion and can supplement position data where the WCD is out of communication range. In one or more embodiments, the accelerometers in the sensor modules 220 can detect movements in multiple (e.g., 3) dimensions or axes. The accelerometer can measure force of acceleration of the WCD and can measure gestures performed by a user while wearing the WCD. In other examples, the accelerometer can detect acceleration of the user while wearing the WCD. This can permit tracking of activity level, such as steps taken or number of laps swum in a pool.

The temperature sensor can be any type of sensor that detects temperature, such as a thermistor, PTC, NTC, etc. In another example, the temperature sensor can use IR light emitted from an object to calculate a surface temperature of the object in a manner clear to those of ordinary skill in the art.

Together, the processor module 210 and the sensor modules 220 can enable the WCD 110 to perform multiple functions including, for example, pedometer, sleep monitor (e.g., which monitors sleep quality), heart rate sensor, pulse oximetry, skin (and in select embodiments, ambient) temperature. In addition, some embodiments of the WCD 110 can further function as a gesture input device. In particular, the present embodiments recognize that the WCD 110 can detect finger motions or gestures which may be difficult for conventional fitness sensors to detect, such as a tap, a snap, a knock on the table, and the like. In some embodiments, the WCD 110 can utilize the accelerometer to measure the activity level (e.g., arm movement) in conjunction with the measured heart rate to determine if the user is walking horizontally, running, swimming, or climbing stairs. Other activities can be identified by the WCD 110 may include biking or sleeping.

In some embodiments, the WCD 110 can also be programmed to learn particular gestures or physical exercise from the user using, for example, a training mode. For example, the user can instruct (e.g., using a computer or a mobile device of the user) the WCD 110 to enter the training mode and perform the gesture or physical exercise; the WCD 110 can record the readings from the sensor modules 220, recognize patterns therefrom, and store the result in, for example the memory 260, so that such gesture or exercise can be recognized by the WCD 110 after the training. The WCD 110 can be configured (e.g., via a mobile application running on a mobile device of the user) so that the recognized gestures can perform functions designated by the user, such as clicks, swipes, unlocks, or media player controls. In one embodiment, the WCD 110 can include near field communication (NFC) chips so that certain functions (e.g., unlocking a smart phone) can be performed when the WCD 110 touches upon or otherwise be detected by another NFC device. In some embodiments, the unlocking function of the WCD 110 can also unlock a user device (e.g., a phone) via the communication module 250 (e.g., Bluetooth) by the WCD 110 transmitting a proper unlock code.

Moreover, the WCD 110 can function as a key or a control device for keyless access to home, automobile, or other suitable user authentication processes. The WCD 110 can also be integrated with games and game consoles so that it can function as an input device to those games and consoles. In some embodiments, the WCD 110 can be adapted for use in medical and home health monitoring, or as a transportation safety device (e.g., that broadcasts emergency messages to relevant authorities). Additional examples of sensors/functionalities of the WCD 110 can include an inertial measurement unit (IMU) (e.g., for more complex gesture recognition, a near-infrared (NIR) spectrometer (e.g., for measuring light absorption and deriving blood glucose/blood alcohol/CO2 content), a Galvanic skin response sensor (e.g., for measuring sweat/nervousness), an electrocardiogram (ECG or EKG), and so forth.

In some embodiments, the processor module 210 can determine (e.g., based on identified physical activities, routine pattern, and/or time) a frequency at which one or more sensors in the sensor modules 220 should operate. Because it is recognized in the present disclosure that the heart rate of a human being typically does not vary too widely (e.g., beyond a certain percentage of what has been previously measured), in some embodiments, the WCD 110 can automatically adjust the sensor modules 220 (e.g., to slow down) so as to save power. More specifically, some embodiments of the WCD 110 can include a phase-locked loop or logic to predict the pulse width by determining lower and upper ranges in which the heart rate is predicted to be, thus only powering up the sensor modules 220 at the time of the predicted heartbeats. For one example, if the WCD 110 determines that the user is at sleep (e.g., based on the heart rate, the body temperature, together with the movements detected by the accelerometer and/or the vibration detector), the WCD 110 can slow down its heart rate detection frequency (e.g., from 1 measurement per second to 1 measurement per 10 seconds) and skip the measurement of several heartbeats because it is unlikely that the heart rate will change drastically during that period. Conversely, if the WCD 110 determines that the user is performing a high intensity physical exercise, the WCD 110 can increase the frequency of monitoring and recording of the sensor modules 220.

In accordance with one or more embodiments, the WCD 110 also includes various modules coupled to the processor module 210 for, by way of example but not limitation, input/output data transmission, battery recharge, or status indication. A view 300 of the exterior window (e.g., window 120) of a WCD (e.g., WCD 110) with example components exposed is shown in FIG. 3A. As shown in the example of FIG. 3A, the modules configured to face the exterior window 120 of the WCD 110 can include parts from the status indicator module 230, the power generation and management module 240, and the communication module 250.

Specifically, one embodiment of the WCD 110 includes the status indicator module 230 coupled to the processor module 210 to indicate various statuses. In some embodiments, the status indicator module 230 includes a light emitting diode (LED) 330, such as shown in FIG. 3A. The LED 330 can be a single red/green/blue (RGB) LED. In other embodiments, the status indicator module 230 can include other suitable types of indicator devices including, for example, a single color LED, an electrophoretic ink (or "e-ink") display, a persistent display, or the like. In accordance with some embodiments, the WCD 110 can utilize the indicator module 230 (e.g., via the RGB LED 330 through the exterior window 120) to visually communicate with the user. For example, a red color can be displayed (e.g., for a predetermined period of time) by the LED 330 that the WCD 110 needs to be recharged, and a green color can be displayed to indicate that the WCD 110 is fully charged. For another example, a blue color can be displayed when the communication module 250 is in use. In one or more embodiments, the user can program a fitness goal (e.g., a target heart rate) to the WCD 110 so that, for example, a green color can be displayed when the heart rate is below the target, a yellow color can be displayed when the target is reached, and a red color can be displayed when the heart rate is above a certain percentage of the set target. Some embodiments of the WCD 110 include the communication module 250 for wireless data transmission. Particularly, in some embodiments, the communication module 250 includes one Bluetooth chip and a Bluetooth antenna 350, such as shown in FIG. 3A. One or more embodiments of the WCD 110 also provides the capability of storing activity logs (e.g., in the memory 260). More specifically, fitness activities, exercise histories, as well as recorded biological signs such as heart rate and body temperature, can be stored onboard in the memory 260 of the WCD 110. Each data entry in the activity logs can be time-stamped using, for example, an onboard real-time clock (e.g., which may be included in miscellaneous modules 270). For power saving and other purposes, the activity log can be downloaded (e.g., via the communication module 250) when requested by the user. In other embodiments, the activity log can be pushed (e.g., via email or other suitable means) by the WCD 110 to a user device at a time designated by the user. In some embodiments, the memory 260 can store up to a full week worth of activity logs.

The WCD 110 can include the power generation and management module 240 for recharging the battery 280 and for providing electrical power to various modules 210-270 in the WCD 110. Particularly, in some embodiments, the power generation and management module 240 includes one or more concentrated photovoltaic (CPV) cells 340, such as shown in FIG. 3A. The CPV cells 340 can be high-efficiency tandem solar cells and can be attached on the flexible printed circuit (e.g., circuit 415,515). Because the small form factor of the embodiments of the WCD 110, CPV cells 340, which can absorb more light energy from a wider spectrum of light than the traditional solar cells, are used. In some embodiments, multiple (e.g., 3) CPV cells 340 can be configured in series to provide sufficient voltage and/or current for charging the battery 280.

According to some embodiments, the WCD can include one or more sensing or imaging devices that can be any type of device capable of detecting electromagnetic radiation, such as visible light, IR, NIR, UV, etc. In one example, the device is an imaging device, such as a CMOS or CCD camera.

Figure 9A:
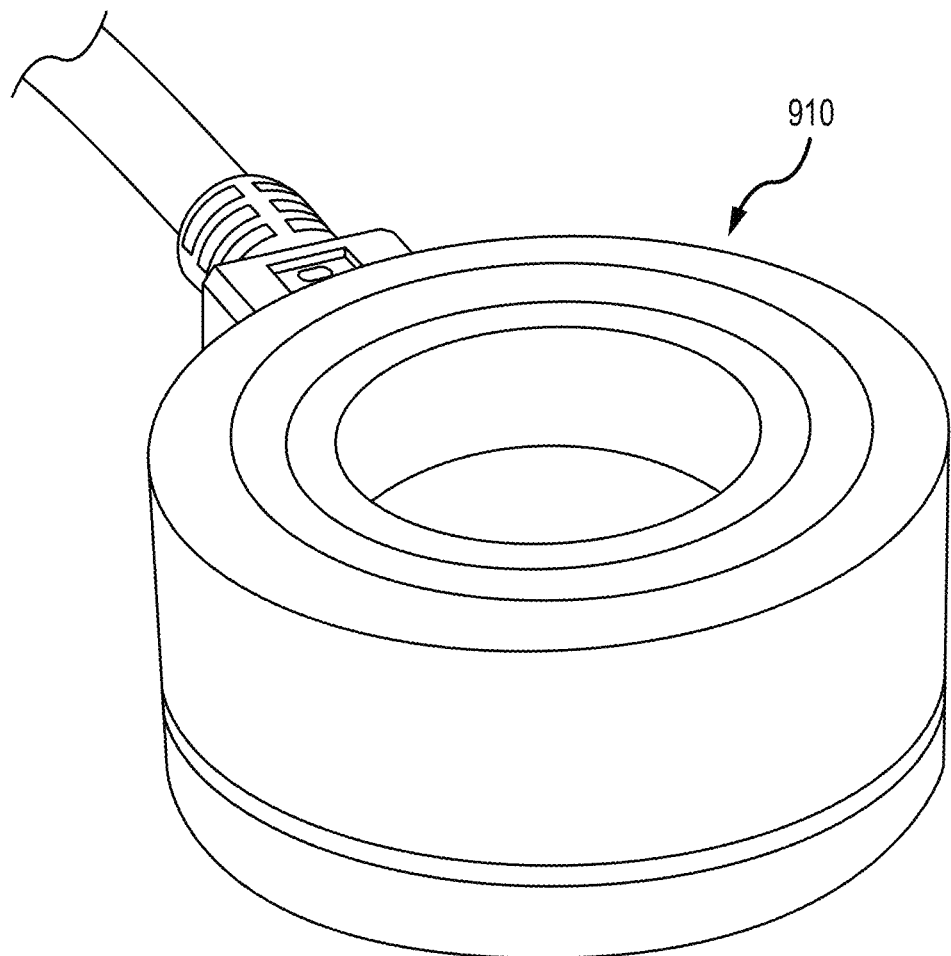
FIG. 9A is a perspective view of a charging device for the ring station in accordance with some embodiments.
Figure 9B:
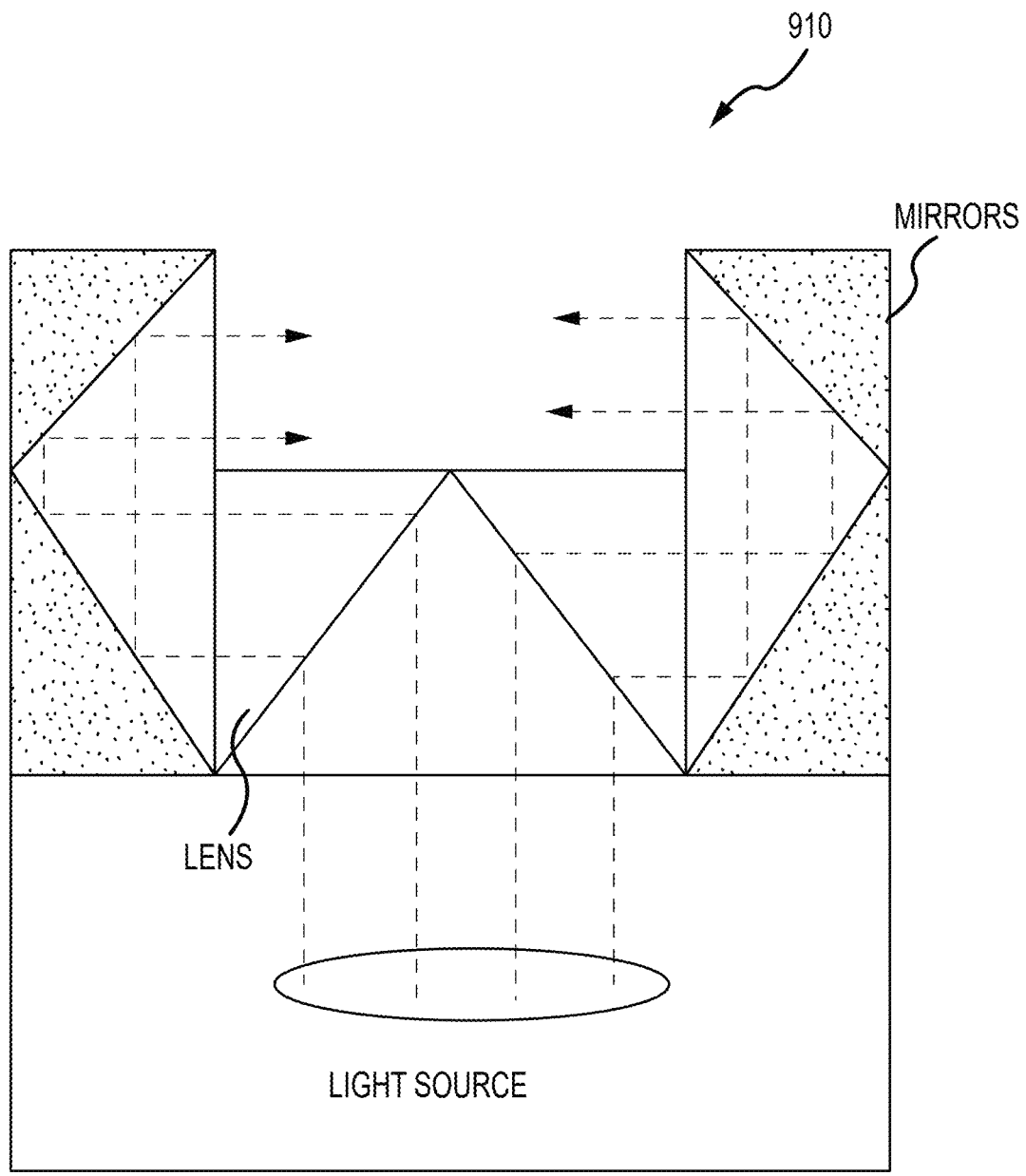
FIG. 9B is an abstract diagram illustrating a partial structure of the charging station of FIG. 9A in accordance with some embodiments.

According to some embodiments, the WCD 110 can be placed or docked into a charging station for recharging. A perspective view 900 of an example charging station 910 for the WCD 110 is shown in FIG. 9A. The charging station 910 can have concentrated light source circumferentially around the WCD 110 so that the user does not have to be concerned with whether the WCD 110 is facing the right direction for charging. Some embodiments of the charging station 910 can include a light distribution means that takes a single light source and distributes the light all around. An abstract diagram illustrating a partial structure of the light distribution means inside the charging device of FIG. 9A is shown in FIG. 9B. It is noted that, even with the charging station 910, for some embodiments, regular outdoor sunlight or other ambient light source can still function as a secondary source of energy so that the CPV cells 340 on the WCD 110 can extend the operational time provided by the battery 280.

Additionally or alternatively, energy source attached to the power generation and management module 240 can be passive; for example, some embodiments provides that a clip with a concentrator lens can be attached to the WCD 110 in a way such that the power generation and management module 240 can charge the battery 280 using natural sunlight. In an alternative embodiment, gemstone(s) (e.g., sapphire, diamond, or other suitable materials) in the shape of a dome or with faceted protrusion can be configured to concentrate/magnify light energy while also serving as a decorative feature.

Figure 6:
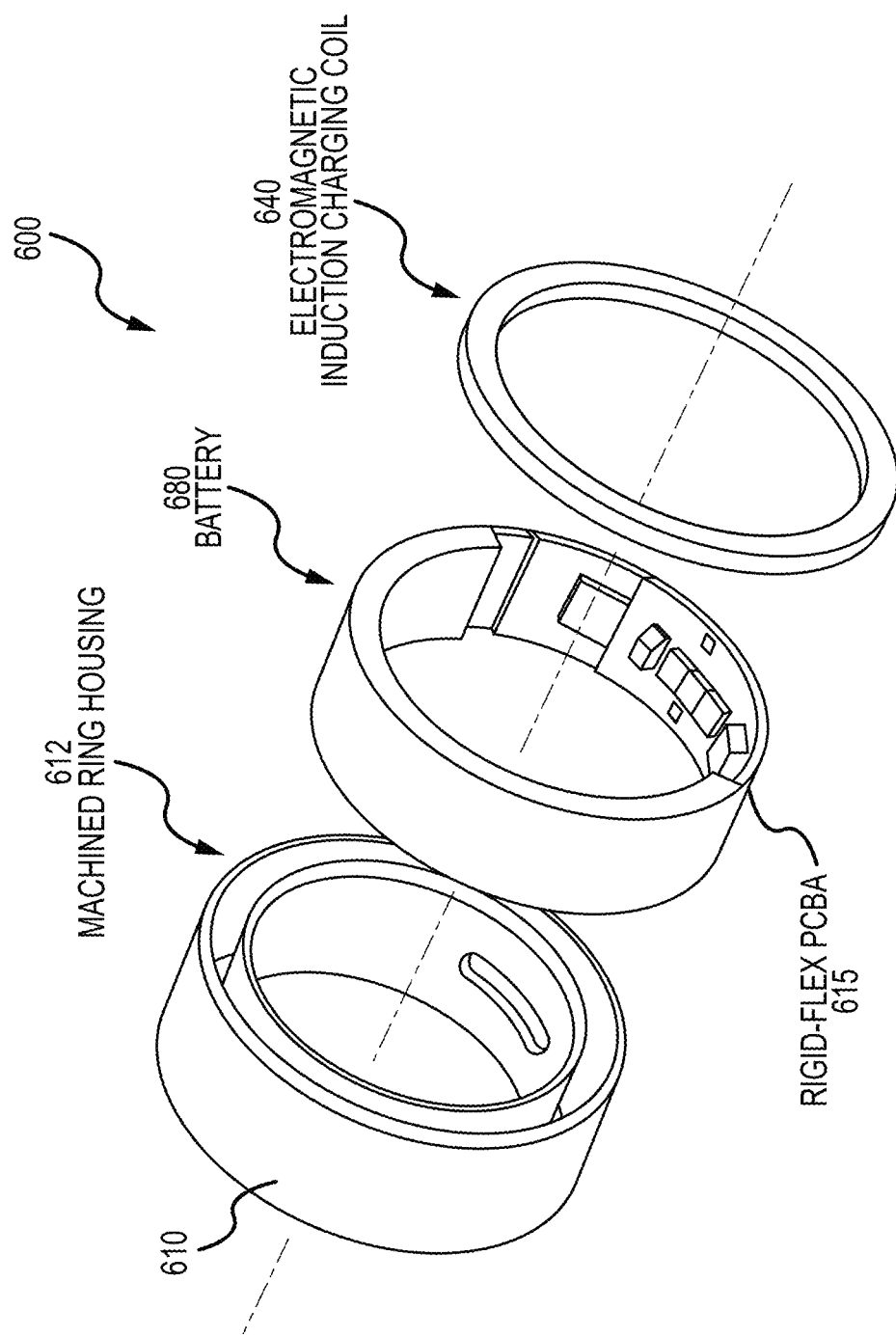
FIG. 6 is an exploded view of a WCD with an alternative charging mechanism in accordance with some embodiments.

In some alternative embodiments, the power generation and management module 240 can include electromagnetic induction charging coil so that a WCD (e.g., ring 610) can be charged using an inductive charger. FIG. 6 shows an exploded view 600 of such alternative embodiment of WCD with the inductive charging mechanism including the charging coil 640, as well as battery 680, housing 612, and rigid-flex PCBA 615. However, it is noted that there may be a need to manufacture the inductive charging coil 640 in different sizes that correspond to different ring sizes. Further, it is noted that the efficiency of the electromagnetic induction charging mechanism may be adversely affected by the adoption of a metallic housing. Additionally or alternatively, to avoid multiple sized coils mounted to the edge of the ring, the coil can be placed on the inner or outer sides of the ring by positioning the coil beneath a window in the metal housing of the ring.

In order to achieve optimal power management of the WCD, one or more of the components can be selected to minimize power usage. For example, a processor, memory, or any other component can be selected based on rated power usage. In one example, it may be desirable to select components that draw current on the order of microamps in order to extend the battery life of the WCD and to allow the WCD to perform health/activity monitoring functions between charging sessions.

Figure 7:
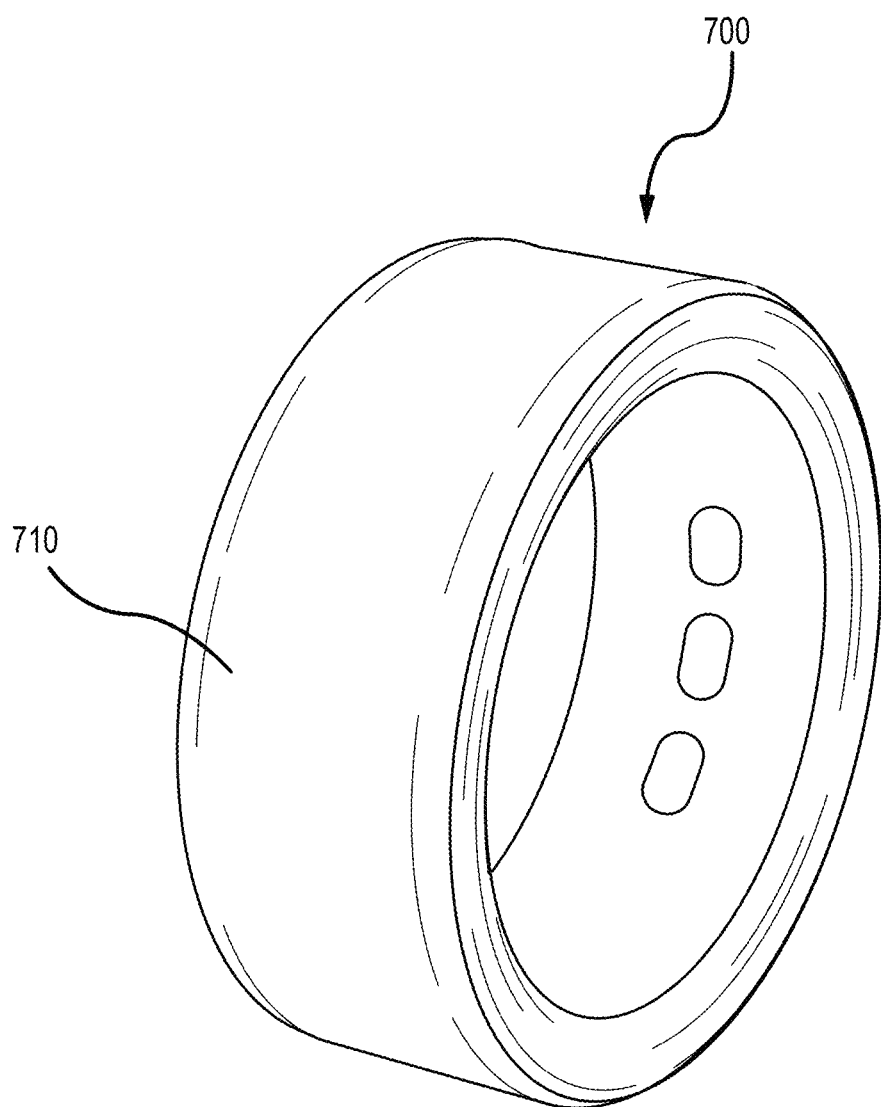
FIG. 7 is a perspective view of an alternative design of a WCD in accordance with some embodiments.
Figure 8:
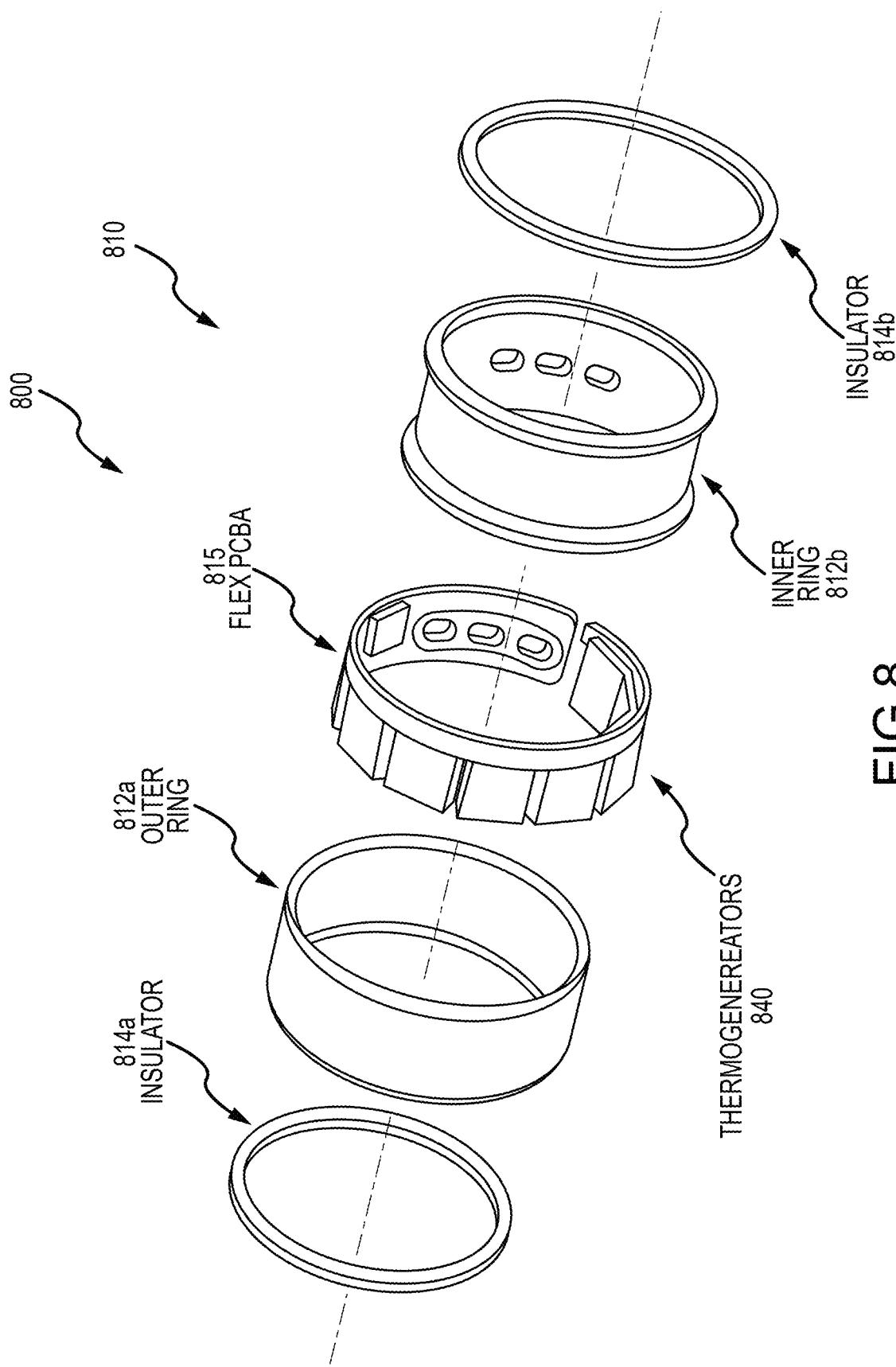
FIG. 8 is an exploded view of the WCD of FIG. 7 illustrating another alternative charging mechanism in accordance with some embodiments.

In still some other alternative embodiments, the power generation and management module 240 can include thermoelectric generator (TEG) modules so that a WCD (e.g., WCD 710,810) can be charged by the difference between the body temperature and the ambient temperature. FIG. 7 is a perspective view 700 of such alternative design, and FIG. 8 is an exploded view 800 of the WCD 710 of FIG. 7. Also shown in FIGS. 7 and 8 is an alternative design of the housing for the WCD where the ring includes an outer ring 812a, an inner ring 812b, and insulators 814a and 814b. However, it is noted that utilizing TEGs for charging the battery may be less than ideal since the difference between body temperature and ambient temperature might not be great enough to fully charge the battery, and that in many occasions (e.g., during sleep), the temperature difference needed for TEG to generate electricity may quickly disappear (e.g., since the WCD 710, 810 may be covered inside the comforter).

The battery can be any type of battery, such as a rechargeable battery. The battery can be a thin, flexible lithium ceramic chemistry battery. In another example, the battery can be a circular formed lithium polymer or lithium ion battery. The battery can provide power to any of the components described above. In one example, the battery can be a lithium cell integrated directly with the flexible PCB described above. Other implementations can integrated the battery directly onto the housing to reduce the volume of space taken up by battery packaging.

The WCD can also include one or more polymer or piezo actuators for providing appropriate haptic or physical feedback and alerts to a user while the user is wearing the ring. The piezo actuator can also provide audible feedback to a user.

Figure 10:
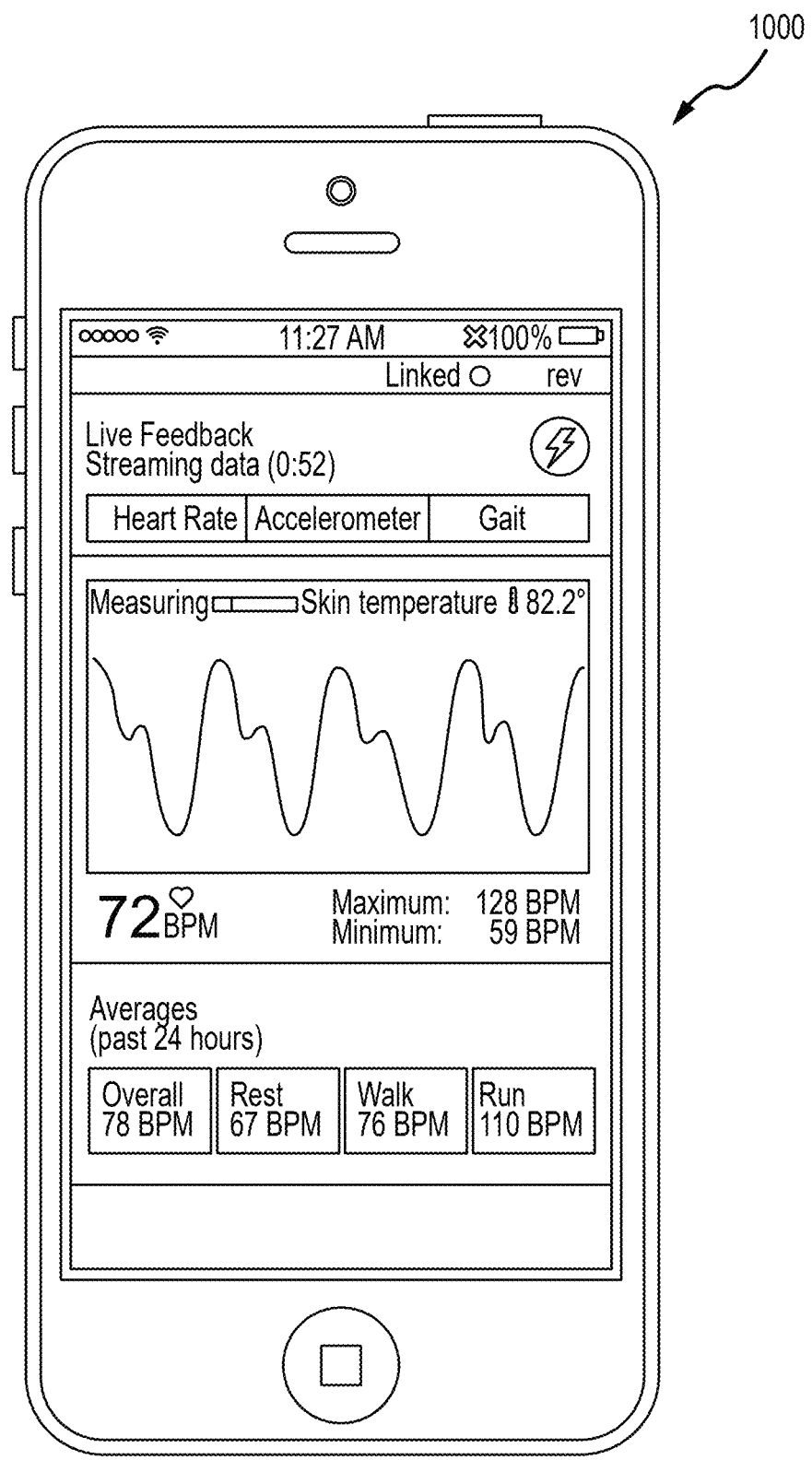
FIG. 10 is an example screenshot illustrating a user interface of a mobile application coupled to the WCD and displaying fitness monitoring readings in accordance with some embodiments.

As previously mentioned, the WCD 110 can be used with a software application (e.g., a mobile phone application for the Apple iOS or the Google Android OS) which can run on the user's computing device (e.g., a mobile device such as a smart phone). Specifically, the software application can facilitate the mobile device of the user to couple to the WCD 110 (e.g., via the communication module 250) for data communication, such as downloading activity logs, changing configuration and preferences, training the WCD. The software application can also generate a user interface showing the results or readings from the health and fitness tracking performed by the WCD 110. FIG. 10 is an example screenshot illustrating such user interface 1000 displaying fitness monitoring readings in accordance with some embodiments.

Figure 11:
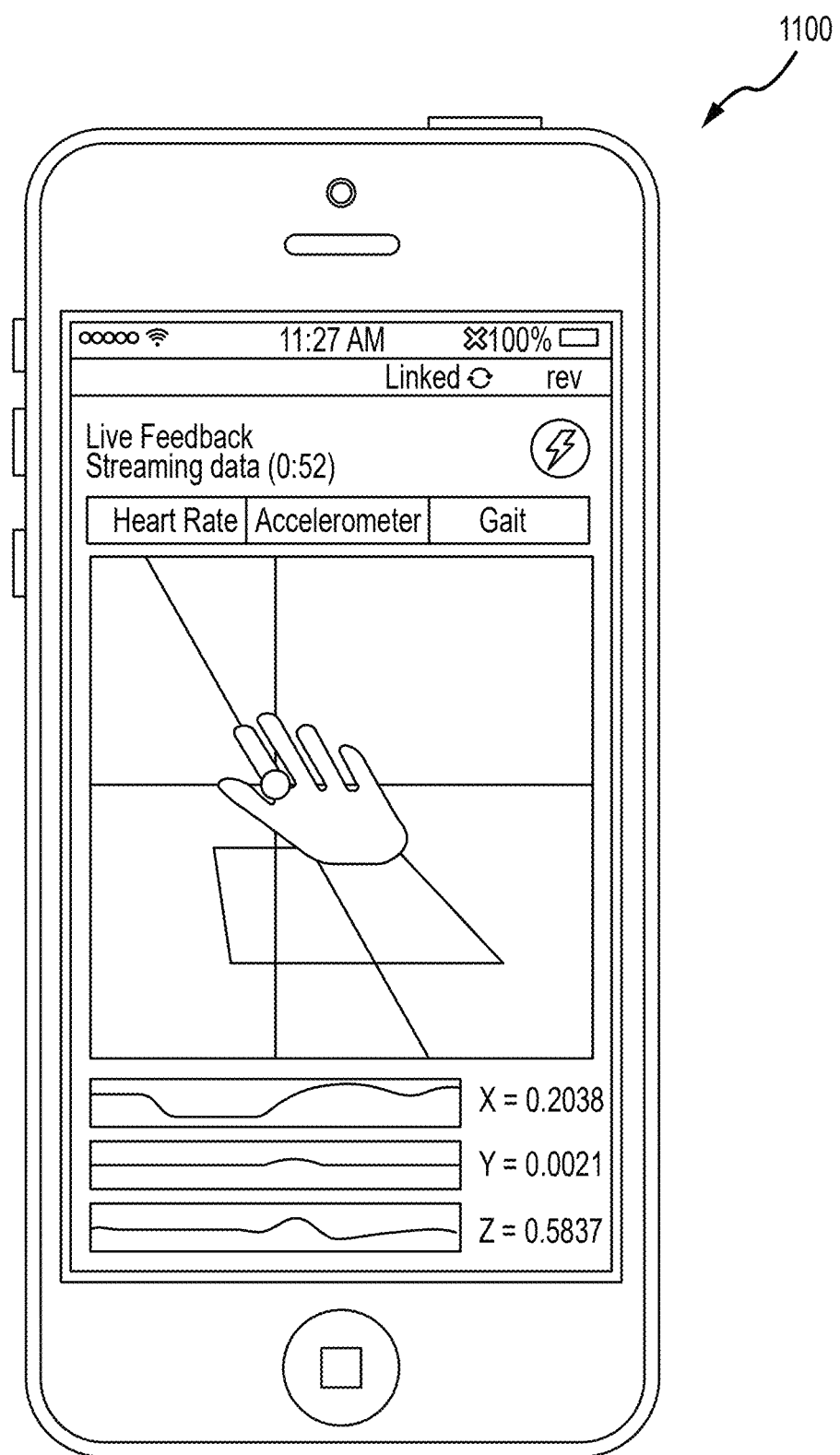
FIG. 11 is an example screenshot illustrating a user interface of a mobile application coupled to the WCD and displaying sensor readings (e.g., for calibration purposes) in accordance with some embodiments.

Further, the WCD 110 can be used for gesture input, and the software application can facilitate the user to customize gesture input and control. FIG. 11 is an example screenshot illustrating such user interface 1100 displaying sensor readings (e.g., for calibration purposes) in accordance with some embodiments. In one or more embodiments, the WCD 110 can also be used directly with other Bluetooth enabled devices such as electronic locks or keyless car entry. In other examples, the WCD 110 can also control other devices via a smartphone and other Wireless LAN enabled devices such as home automation systems.

Figure 3C:
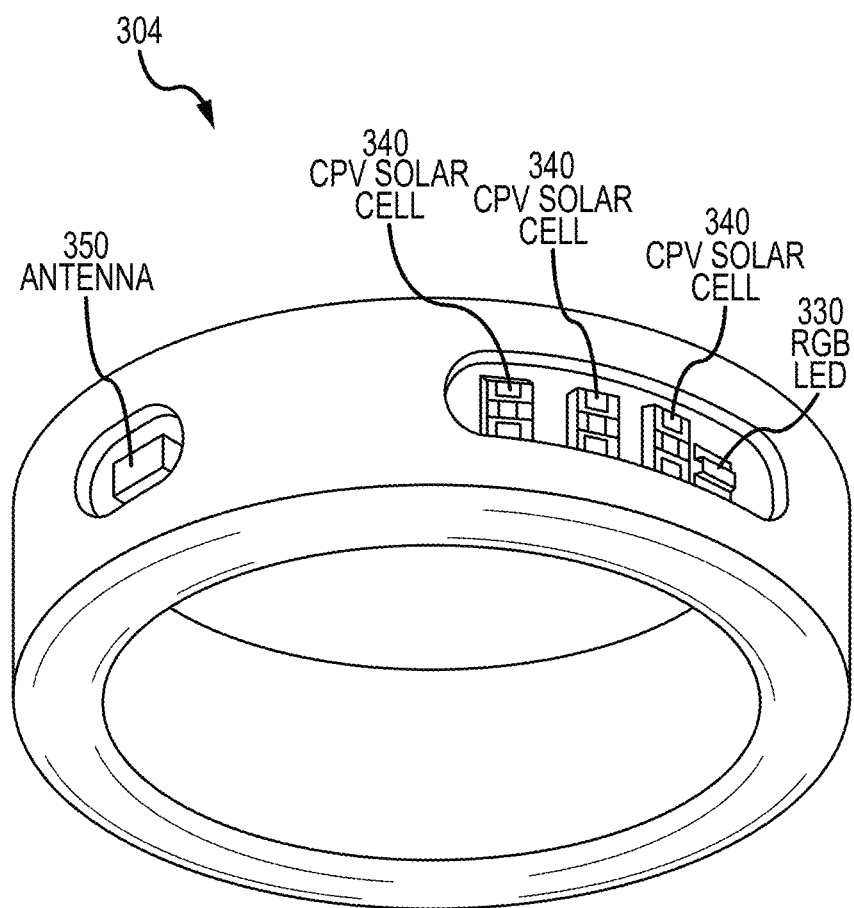
FIG. 3C is a view of the exterior windows of an alternative WCD with example components exposed in accordance with some embodiments.

FIG. 3C is a view 304 of two exterior windows of an alternative WCD (e.g., WCD 112 of FIG. 3C) with example components exposed in accordance with some embodiments. The components 330, 340, and 350 shown in FIG. 3C function similarly to those components described in FIG. 3A. However, some components (e.g., antenna 350) can be positioned to face a different exterior window than the exterior window the rest of the components face. This may increase the mechanical strength of the housing structure of the ring, and/or may reduce signal interference among the components.

Figure 4:
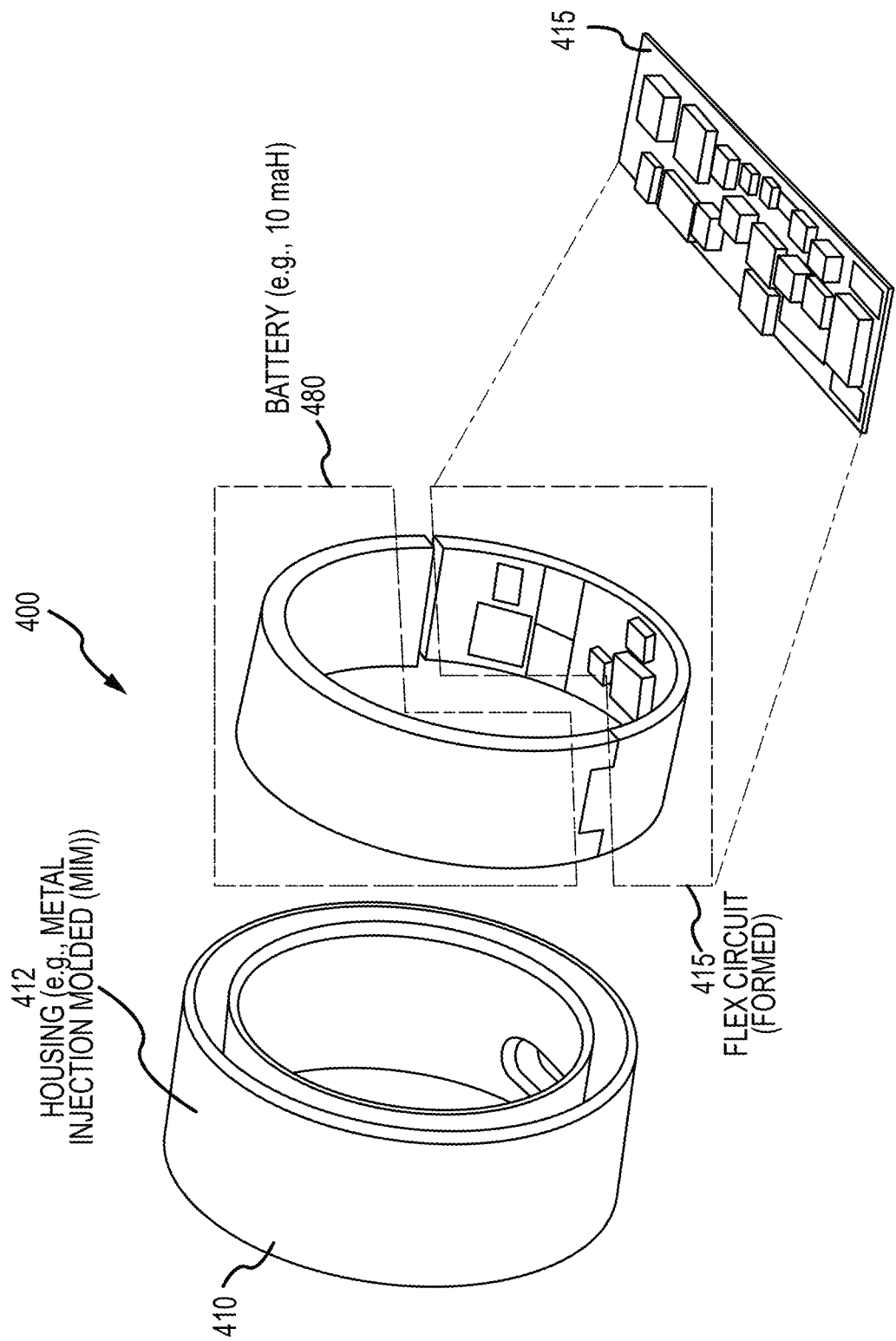
FIG. 4 is an exploded view of a WCD illustrating a battery and a flexible circuit which are configured to fit inside the housing of the WCD in accordance with some embodiments.
Figure 5:
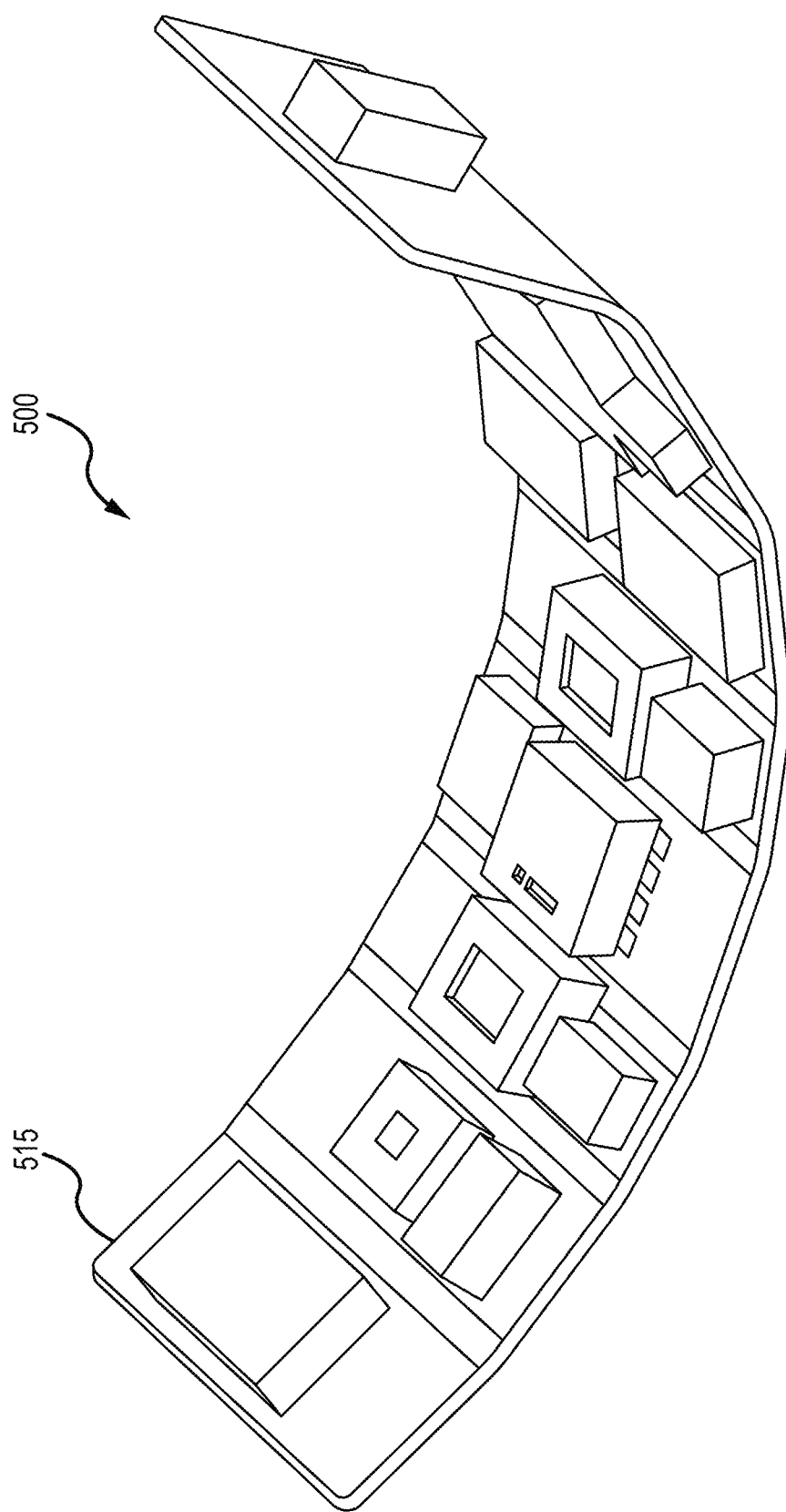
FIG. 5 is a perspective view of the flexible circuit of FIG. 4 in accordance with some embodiments.

FIG. 4 is an exploded view 400 showing an exemplary WCD 410 (e.g., WCD 110) illustrating a battery 480 and a flexible circuit 415 which are configured to fit inside a housing 412 of the WCD 410. It is recognized by the present disclosure that a human being's finger can come in various different sizes and so should the WCD 410. In order to reduce the cost of manufacturing different sizes of printed circuits, in some embodiments, the modules 210-270 (of FIG. 2) are formed on a flexible or rigid-flex printed circuit (FPC) board, an example 500 of which is shown as FPC 515 in FIG. 5. In particular, one or more embodiments provide that the FPC 515 and the battery 480 are not specific to a ring size, and that the same circuitry and/or battery can fit a multitude of sizes.

According to some embodiments, the WCD 410 provides a desirable form factor for a user to wear it for a prolonged period of time. The edges and the shape of the WCD 410 can be configured in a way that is comfortable and ergonomic; for example, the finished parts of the embodiments are to be free from burrs and sharp edges. The material which forms the housing portion of the WCD 410 can include medical grade metallic alloys that reduce the likelihood of allergic reactions. Examples of the housing material include stainless steel, tungsten carbide, titanium alloy, silver, platinum or gold.

In the examples shown in FIG. 4, the U-shape of the ring housing 412 allows for the flexible PCB 415 to be inserted into the edge of the WCD 410. The windows (e.g., windows 120, 130) on the walls of the WCD 410 can align with the operating circuitry to allow, for example, battery charging, Bluetooth connection, and user feedback LED/micro display on the outer wall, and biological feedback sensors (e.g., pulse oximetry, temperature sensor) on the inner wall. In one or more embodiments, the WCD 410 can be completely sealed using potting epoxy. The sealing epoxy can be transparent to allow light to pass through for the CPVs and sensors. In some embodiments, the WCD 410 can be potted with two different compounds. In these embodiments, the body of the WCD 410 can be filled with clear material, and the edge of the WCD 410 can be filled with an opaque material so that different colors can be incorporated (e.g., as a decorative element). It is noted that sealing the assembly using potting epoxy can also bring the additional benefit of making the WCD 410 completely or almost completely waterproof as well as increasing the structural rigidity of the WCD 410.

I. INTERNAL HOUSING/EXTERNAL POTTING

Figure 12A:
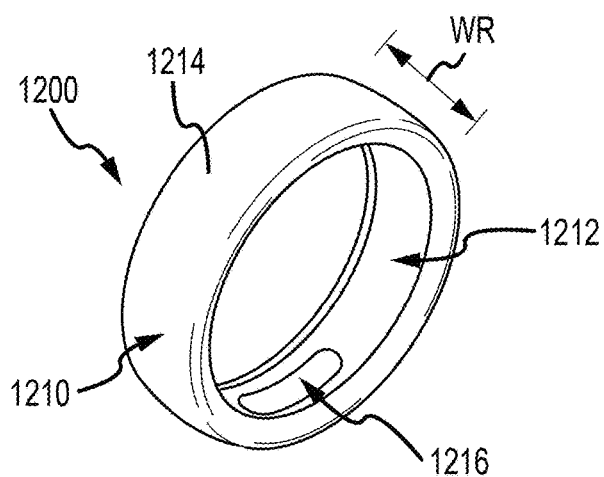
FIG. 12A is a perspective view of a wearable computing device (WCD) according to one or more aspects of the disclosure.
Figure 12C:
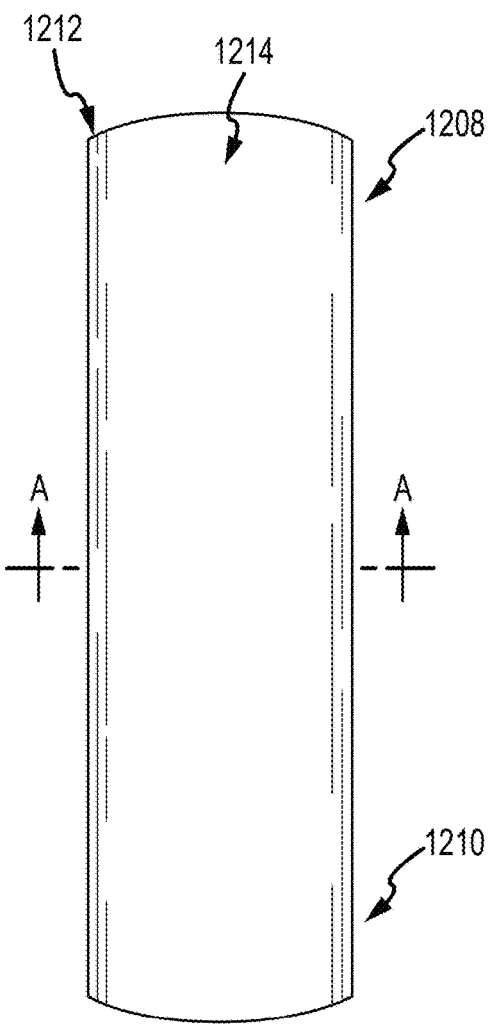
FIG. 12C is a front view of the WCD according to one or more aspects of the disclosure.
Figure 12B:
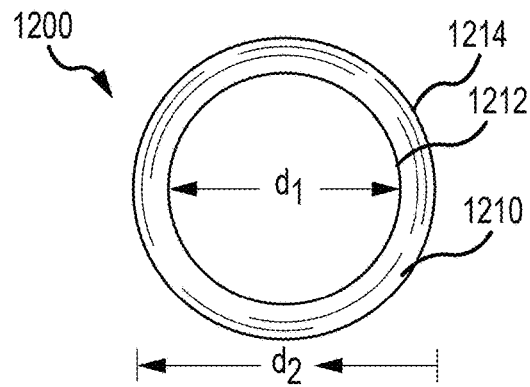
FIG. 12B is a side view of a WCD according to one or more aspects of the disclosure.

FIG. 12A is a perspective view and FIG. 12B is a side view of a WCD 1200 according to one or more aspects of the disclosure. The WCD 1200 can be in the shape of a ring and can be worn on any of the five fingers (including the thumb) of (typically) a human user. In this regard, the WCD 1200 can define an interior diameter d1 and exterior diameter d2. The interior diameter d1 can be defined as the distance between opposing points on the interior surface of the ring, with the interior surface being the portion of the WCD facing the finger of a user while the device is worn by the user. The interior surface of the WCD can generally define a finger space for receiving the finger of the user. The exterior diameter d2 can be defined as the diameter between opposing points on the exterior surface of the ring, with the exterior surface being the portion of the WCD opposed to the interior surface and facing away from the finger of the user.

The interior diameter d1 and exterior diameter d2 can be any size to accommodate any finger size. In one example, d2 is determined by d1 plus a thickness of any components and/or flexible circuit boards disposed within the WCD. Additionally, although depicted as being circular, the finger space of the WCD 1200 can be any shape, such as ovular, elliptical, or the like, to accommodate users with atypical finger profiles. In these examples, the dimensions of the interior and/or exterior diameter may be measured according to other variables, such as length, width, major diameter, minor diameter, etc. By way of non-limiting example, the WCD interior diameter d1 (the diameter generally defining the ring size) can be in an approximate range of 12 mm to 24 mm so as to accommodate finger sizes ranging from a small child to a larger adult, and on any acceptable finger, including the thumb. The exterior diameter d2 can also be any reasonable size or shape, and can define an approximate range of between 18 mm and 30 mm. Likewise, the thickness between diameters d1 and d2 can vary widely, but can typically reside in an approximate range of 1.5 mm to 3 mm. The width WR of the WCD along the direction of finger extension (finger longitudinal direction) is widely variable, and can be selected, in part to accommodate internal and external components. In a non-limiting example, the width WR is in a range of approximately 3 mm to 8 mm.

The WCD 1200 can include an overall housing 1210 that includes an internal housing 1212 and an external potting or encapsulant 1214. Together, the internal housing 1212 and external potting 1214 combine to form the overall form factor of the WCD 1200, in addition to providing a housing for one or more electronic components stored within the housing 1210 of the WCD 1200, as will be described in greater detail below.

The internal housing 1212 can be formed of any material, such as a nonconductive material, a conductive material, a ferrous material and/or a nonferrous metal, composite material (e.g. carbon-fiber and/or glass fiber composite) a dielectric material, or a combination of any of the above. In one example, the material of the inner housing 1212 is conductive and nonferrous, such as aluminum, titanium, or stainless steel. In other examples, the internal housing can be formed of a polymer, such as plastic. The external potting 1214 can be formed of any material, solid or gelatinous, that can provide resistance to shock and/or vibration and can prevent moisture and/or debris from entering the housing 1210 of the WCD 1200, such as silicone, epoxy, polyester resin or any other polymer.

In one example, the external potting 1214 can be transparent. In this regard, the transparent external potting can allow electromagnetic radiation, such as visible, IR, or UV light sources from inside the housing 1210 to pass through the external potting 1214 without the need of a window or discontinuity in the external potting 1214 and without changing the optical properties of the radiation. In the same vein, electromagnetic radiation sources, such as visible, IR, or UV light, external to the housing can pass through the external potting 1214 and can be detected by, sensed by, or fall incident upon internal components of the WCD 1200 without the need for a window or discontinuity in the housing and without changing the optical properties of the radiation. In another example, the external potting 1214 can be tinted. The tint can be cosmetic and can prevent the internal components of the WCD to be visible by the user. In this regard, depending on the tint, optical properties of light passing therethough may be slightly changed. For example, certain colors of the light can be filtered and can result in decreased power transmission. The above description regarding external potting 1214 can be applied to any of the pottings described below.

The internal housing 1212 can define a window 1216. In one example, the internal housing is formed of a material that completely or partially prevents light (or other electromagnetic radiation) from passing through the internal housing 1212. In this regard, the internal housing 1212 can define the window 1216 to allow for such radiation to pass through the housing 1212. As shown, the window 1216 can be generally elliptical-shaped, but can be any other suitable shape according to other examples, such as rectangular, circular, ovular, etc. Since the window 116 is defined by the internal housing 1212, the window 1216 can face the finger of the user while the user is wearing the WCD 1200, which can provide many advantageous features and implementations, as will be described in greater detail below.

Figure 12D:
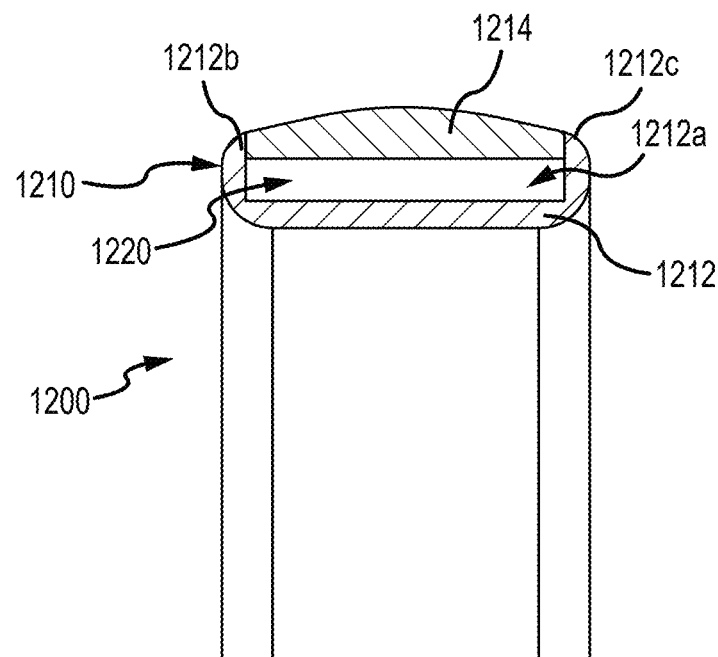
FIG. 12D is a cross section of the WCD along the line A-A of FIG. 12C.

FIG. 12C is a front view of the WCD and FIG. 12D is a cross section of the WCD 1200 along the line A-A of FIG. 12C. As shown, the internal housing 1212 can have a generally U-shaped internal surface 1212a to accommodate one or more internal components and can define a pair of flanges 1212b and 1212c. The external potting 1214 can extend between the flanges 1212b and 1212c of the internal housing to provide an internal space 1220 to accommodate one or more components. By virtue of the external potting 1214, the internal space 1220 defined by the internal surface 1212a and the external potting 1214 can be hermetically sealed, thereby preventing debris, dust, moisture, or any other unwanted fluids or materials from interacting with the internal components of the WCD 1200. Although not depicted, the internal components can reside within the internal space 1220, and the external potting 1214 can be disposed immediately atop the components to provide the seal.

Figure 12E:
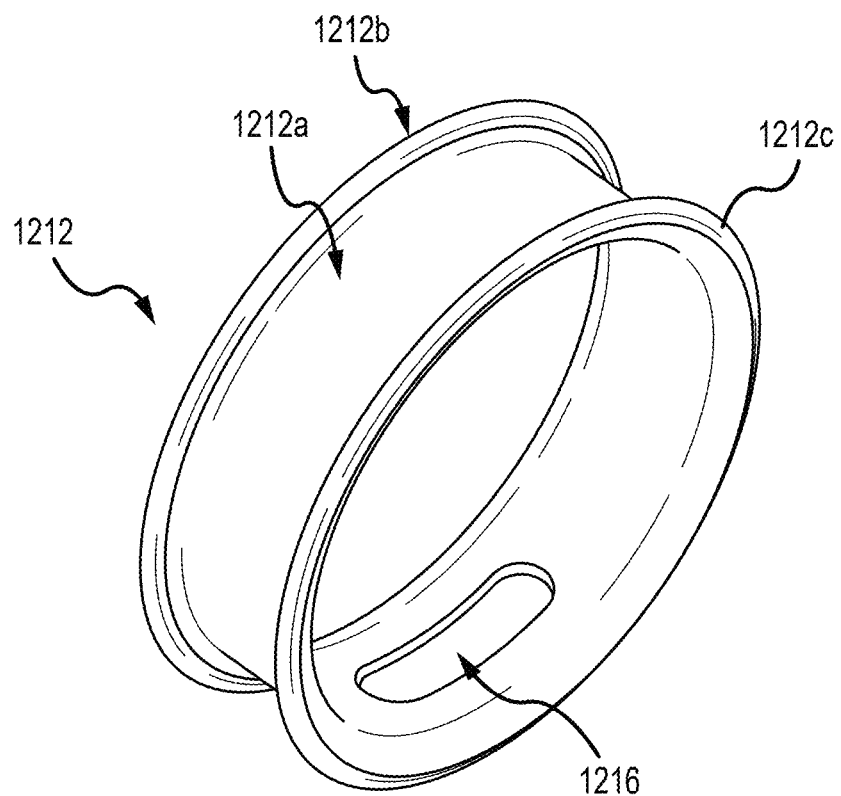
FIG. 12E is a perspective view of the internal housing without external potting.

FIG. 12E is a perspective view of the internal housing 1212 without external potting 1214. As shown, the internal surface 1212a defines a generally U-shaped surface for receiving the components.

Figure 12F:
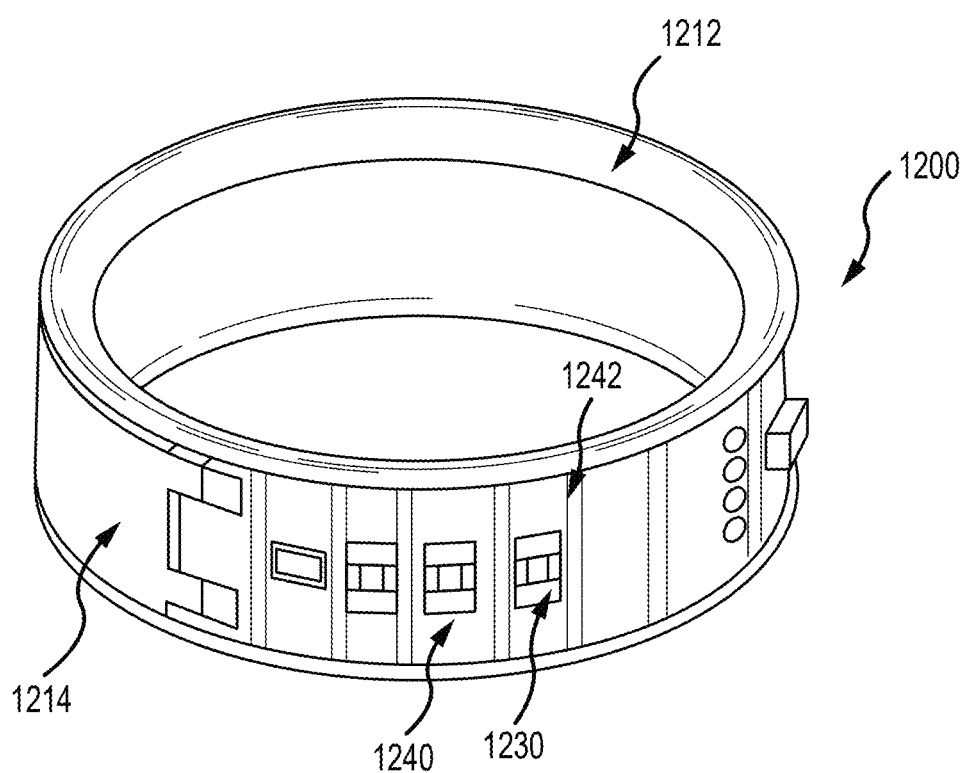
FIG. 12F is a perspective view of the internal housing with a portion of the external potting removed and showing one or more components and printed circuit board (PCB)

FIG. 12F is a perspective view of the internal housing 1212 with a portion of the external potting 1214 removed and showing one or more components 1230 and printed circuit board (PCB) 1240. The components and PCB can be constructed as flex circuits, thereby allowing the components 1230 and PCB 1240 to be geometrically configured within the ring shaped internal space 1220. The PCB 1240 can be any type of flexible material clear to those of skill, such as polyimide, PEEK, etc. Additionally, the PCB could be rigid-flex whereby panels of RF4 are connected together with a flexible substrate.

As shown, the PCB 1240 and the components 1230 can be disposed within the internal space 1220 generally defined by the internal surface 1220a and the flanges 1220b-c. The PCB 1240 can define one or more folding regions 1242 that allow the PCB 1240 to conform to the circumference and/or perimeter of the internal surface 1212a. The PCB 1240 can extend around at least a portion, or up to an entire circumference, of the internal surface 1212a. In one example, the size of the internal diameter d1 of the WCD can determine the portion of the internal surface 1212a around which the PCB 1240 extends. Illustratively, for a larger ring size and a larger internal diameter d1, the PCB 1240 can extend only a portion (an arc) of the overall circumference, while for smaller ring sizes a greater portion (arc) of the circumference can be employed to accommodate PCB 1240 and the internal components 1230. The adjacent portions of PCB can form an arc angle therebetween by virtue of the folding regions disposed therebetween, allowing for the PCB to be conform to the internal surface 1212a.

II, EXTERNAL HOUSING/INTERNAL POTTING

Figure 13:
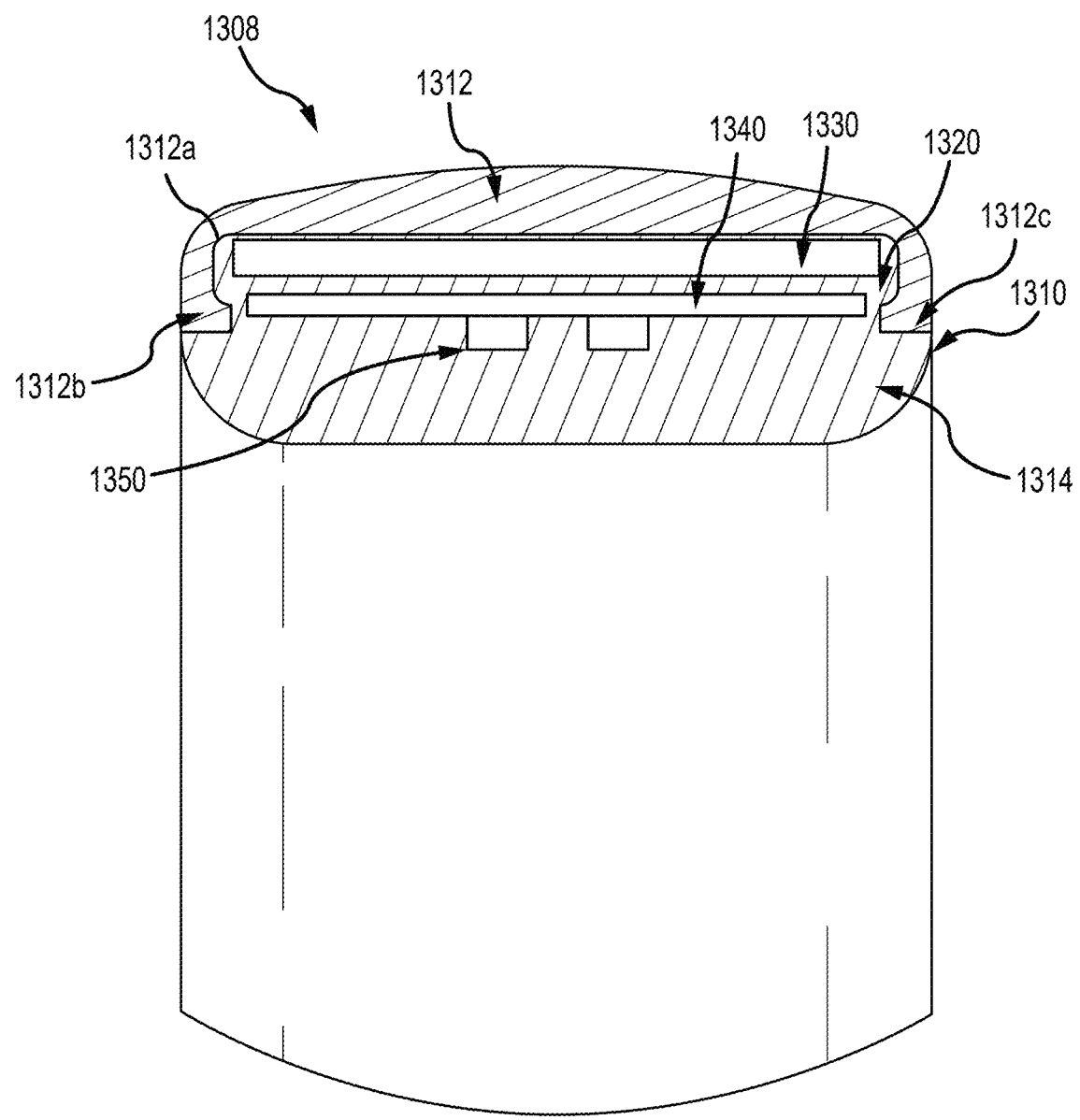
FIG. 13 is a cross section of a WCD according to another aspect of the disclosure.

FIG. 13 is a cross section of a WCD 1300 according to another aspect of the disclosure and illustrative embodiments. In this example, the WCD 1300 includes a housing 1310 that includes an external housing 1312 and an internal potting or encapsulant 1314. The external housing 1312 includes an internal surface 1312a that has a generally C-shaped cross section—but alternate cross section shapes, such shapes with an external notch or groove. The external housing includes flanges 1312b-c that extend toward each other, beyond portions of the internal surface 1312a, to define a partially enclosed internal space 1320. In an assembled state, the WCD 1300 can include a battery 1330, a PCB 1340, and components 1350, which can be at least partially or completely disposed within the partially enclosed internal space 1320. The internal potting 1314 can extend between the flanges 1312b-c and can seal the partially enclosed internal space 1320. The components can be encapsulated by the internal potting 1314. The PCB 1340 and components 1350 can extend along an inner circumference of the internal surface 1312a.

Illustratively, the external housing 1312 can be formed of the same materials as the internal housing 1212 described above, and the internal potting 1314 can be formed of the same materials as the external potting 1214 described above. As also described above, the internal potting 1314 can be transparent and the external housing 1312 can define one or more windows according to one or more aspects of the disclosure.

Figure 14A:
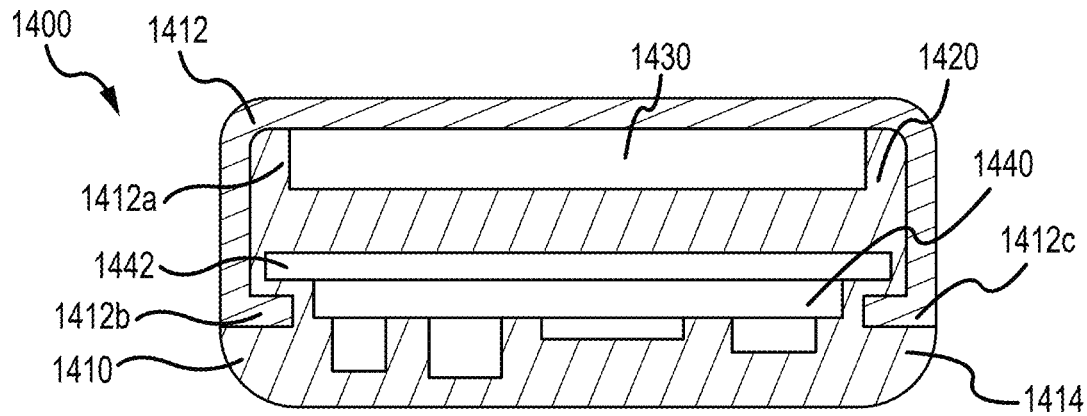
FIG. 14A is a cross section of a WCD according to another aspect of the disclosure.

FIG. 14A is a cross section of a WCD according to another aspect of the disclosure and illustrative embodiment. In this example, the WCD 1400 includes a housing 1410, internal surface 1412a, an internal or external housing 1412, an internal or external potting 1414, an internal space 1420, a battery 1430, a flexible circuit 1440, and one or more components 1450. This example is similar to the examples described above with respect to FIGS. 12 and 13, except the addition of a stiffener element 1442 and the flanges 1412b-c extend further into the space 1420 toward one another such that the flanges 1412b-c overlap with the stiffener element 1442.

Figure 14B:
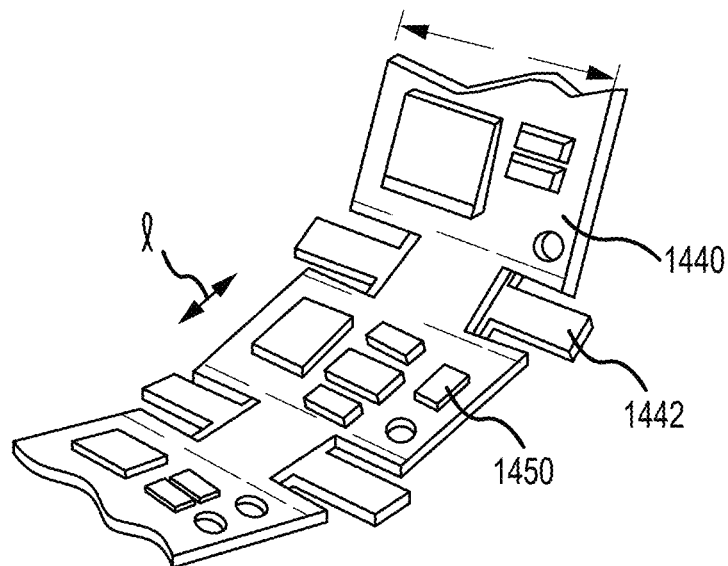
FIG. 14B is a perspective view of the PCB and stiffener element of FIG. 14A.
Figure 14C:
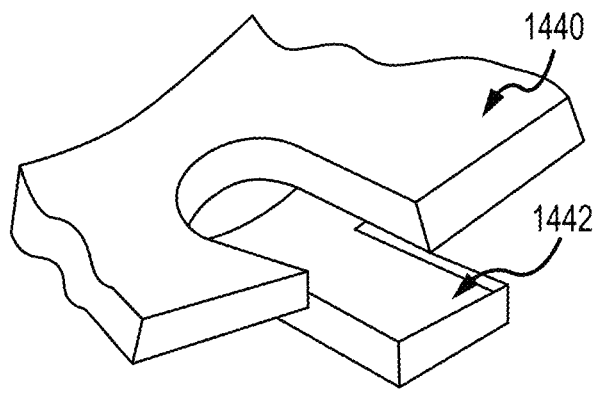
FIG. 14C is a perspective view of the PCB and stiffener element of FIG. 14A.

FIG. 14B is a perspective view of the PCB and stiffener element of FIG. 14A. As shown in FIG. 14B, the stiffener element 1442 extends beyond an overall width w of the PCB 1440 and extends wider than a distance between flanges 1412b-c. The stiffener element is disposed between folding regions 1444. The PCB 1440 can include one or more stiffener elements 1442 attached thereto, and the elements 1442 can be disposed periodically (in separated intervals) along a length l of the PCB 1440. As shown in FIG. 14C, the stiffener element 1442 can be disposed underneath the flexible circuit 1440, e.g., on a face of the flexible circuit 1440 opposed to the face on which the components 1450 are disposed, and can be permanently or semi-permanently attached thereto. The stiffener element can be implemented in any of the configurations described, and in particular, with either the internal housing/external potting arrangement or the external housing/internal potting arrangement.

The stiffener element 1442 can be formed of any material, such as polyamide or thin FR4, depending on construction of the PCB 1440. In particular, the material of the stiffener can be chosen to be more or less flexible than the PCB 1440. In one example, the stiffener element 1442 can be a polyamide stiffener disposed on a back surface of a flexible PCB. In another example, the stiffener element 1442 can be FR4 and can be substantially flush with respect to the flanges 1412b-c. In this regard, the stiffener element can extend substantially the distance between flanges 1412b-c and may not deform upon insertion into the space 1420. The stiffener element can include surface features disposed on an edge thereof, with the edge facing one of the flanges 1412b-c. The surface features can include a sawtooth profile (e.g., intersecting straight lines at acute angles), or any other type of feature capable of providing an interference fit between flanges 1412b-c.

Figure 14D:
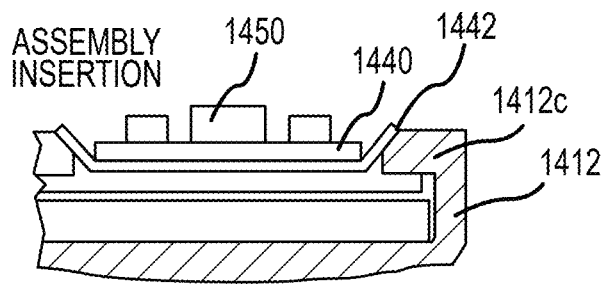
FIG. 14D shows a cross section of the WCD at a point in time when the PCB is being inserted into the internal space and prior to the application of potting.

FIG. 14D shows a cross section of the WCD at a point in time during assembly/manufacture when the PCB 1440 is being inserted into the internal space 1420 and prior to the application of potting 1414. As shown, the stiffener 1442 contacts the flanges 1412b-c of the housing 1410 by virtue of the width w of the stiffener element 1442. Upon an application of force, the PCB 1440 and stiffener 1442 assembly can be inserted into the internal space 1420. In this regard, the stiffener element has a predetermined flexibility that allows for a certain amount of flexion, as shown in FIG. 14D. The flexion allows for the flexible circuit 1440 to be inserted within the internal space 1420 and can prevent the flexible circuit 1440 from being removed or from accidentally falling out once inserted. In this regard, the flexible circuit 1440 is held in place within the space 1420 by virtue of the width of the stiffener element 1442 and the distance between the flanges 1412b-c. Once inserted, the potting 1414 can be applied free of the concern of improper positioning of the flexible circuit 1440.

Figure 14E:
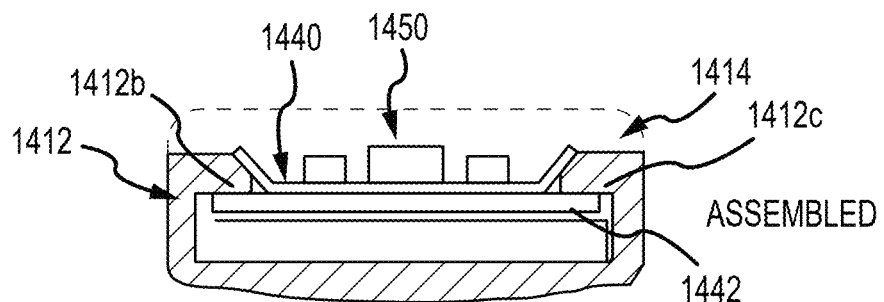
FIG. 14E is a cross section of the WCD of after a potting material has been applied subsequent to the WCD of FIG. 14D.

FIG. 14E is a cross section of the WCD of after a potting material 1414 has been applied subsequent to the WCD of FIG. 14D.

III. INNER/OUTER BANDS

Figure 15A:
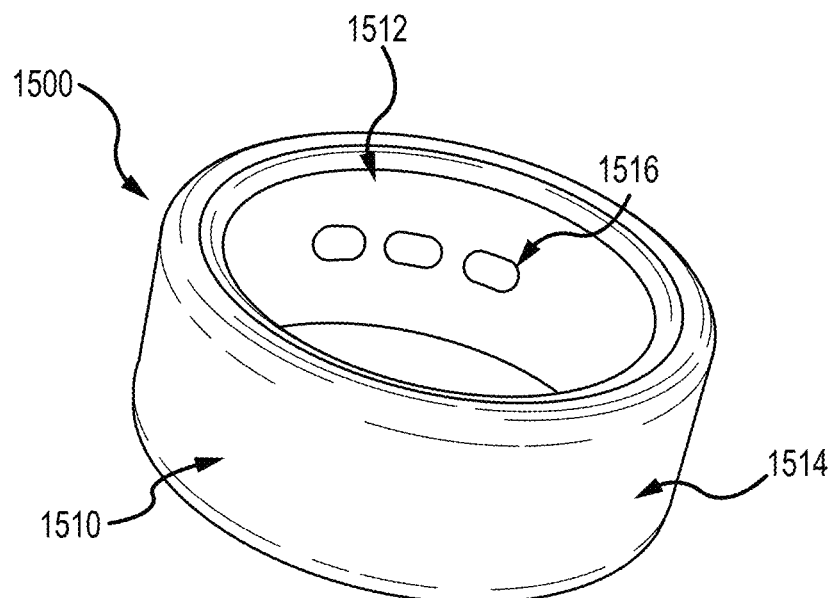
FIG. 15A depicts a perspective view of a WCD according to another aspect of the disclosure.

FIG. 15A depicts a perspective view of a WCD 1500 according to another aspect of the disclosure. In this example, the WCD includes a housing 1510 that includes an internal housing 1512 and an external housing 1514. The internal housing 1512 can be similar to the internal housing described above with respect to internal housing 1212, and the external housing can be similar to the external housing described above with respect to external housing 1312. The internal housing 1512 can include one or more windows 1516 that can allow electromagnetic radiation (e.g. visible and near-visible light) to pass therethrough, allowing it to fall incident upon components disposed within the housing 1510 and allowing EM radiation sources (e.g. visible light, RF, IR, etc.) within the housing to exit the housing.

Figure 15B:
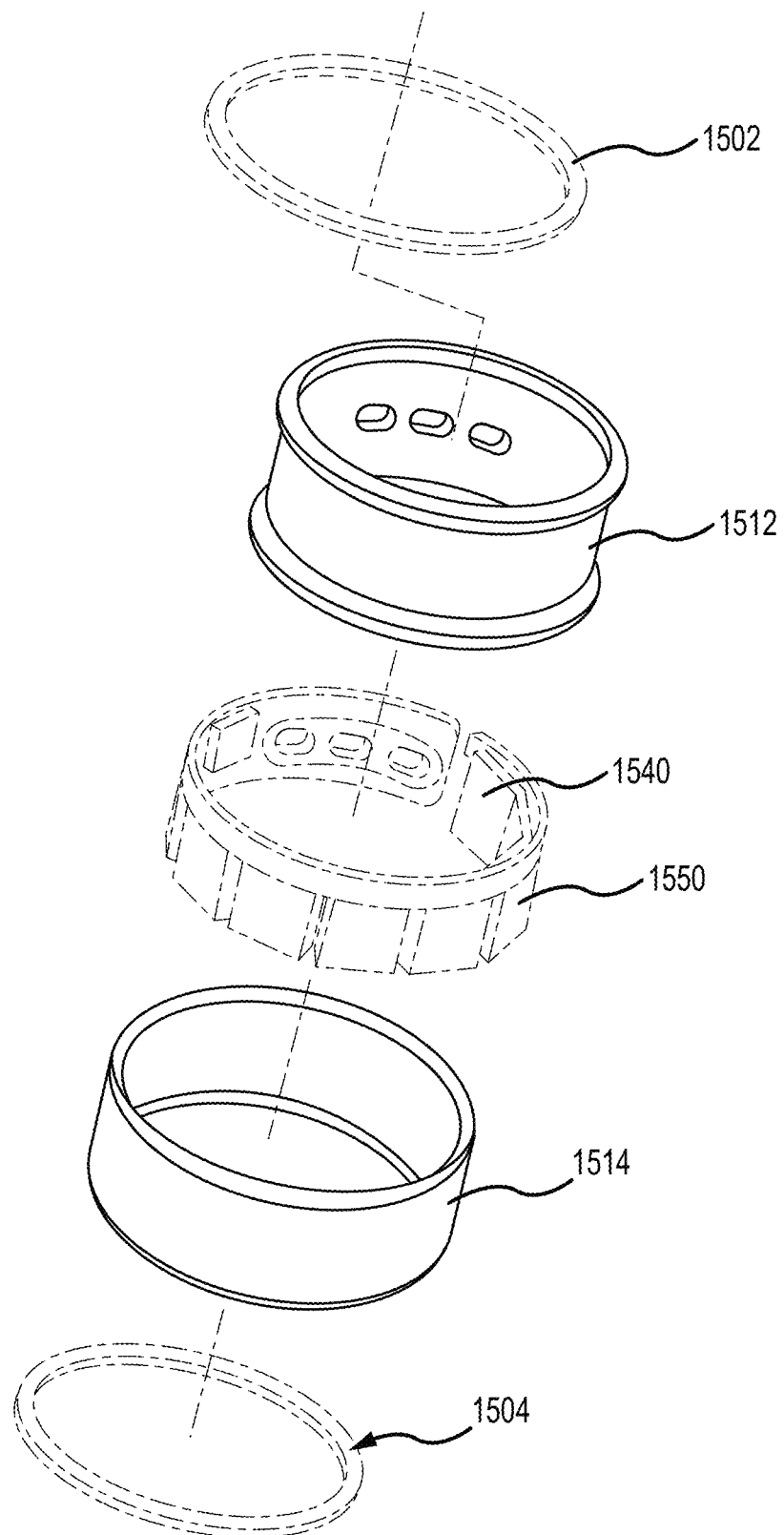
FIG. 15B is a side view of the WCD of FIG. 15A.

FIG. 15B is an exploded view of the WCD 1500. As shown, the WCD can include internal housing and external housing 1512 and 1514. The WCD can further include a PCB 1540 and components 1550. Once the housings 1512-1514 are assembled and the PCB 1540 and components 1550 are assembled within space defined between the housings 1512-414, potting layers 1502 and 1504 can be applied to seal the WCD at both sides thereof to ensure a secure seal.

IV. INNER/OUTER BANDS WITH U SHAPED WINDOW

Figure 16A:
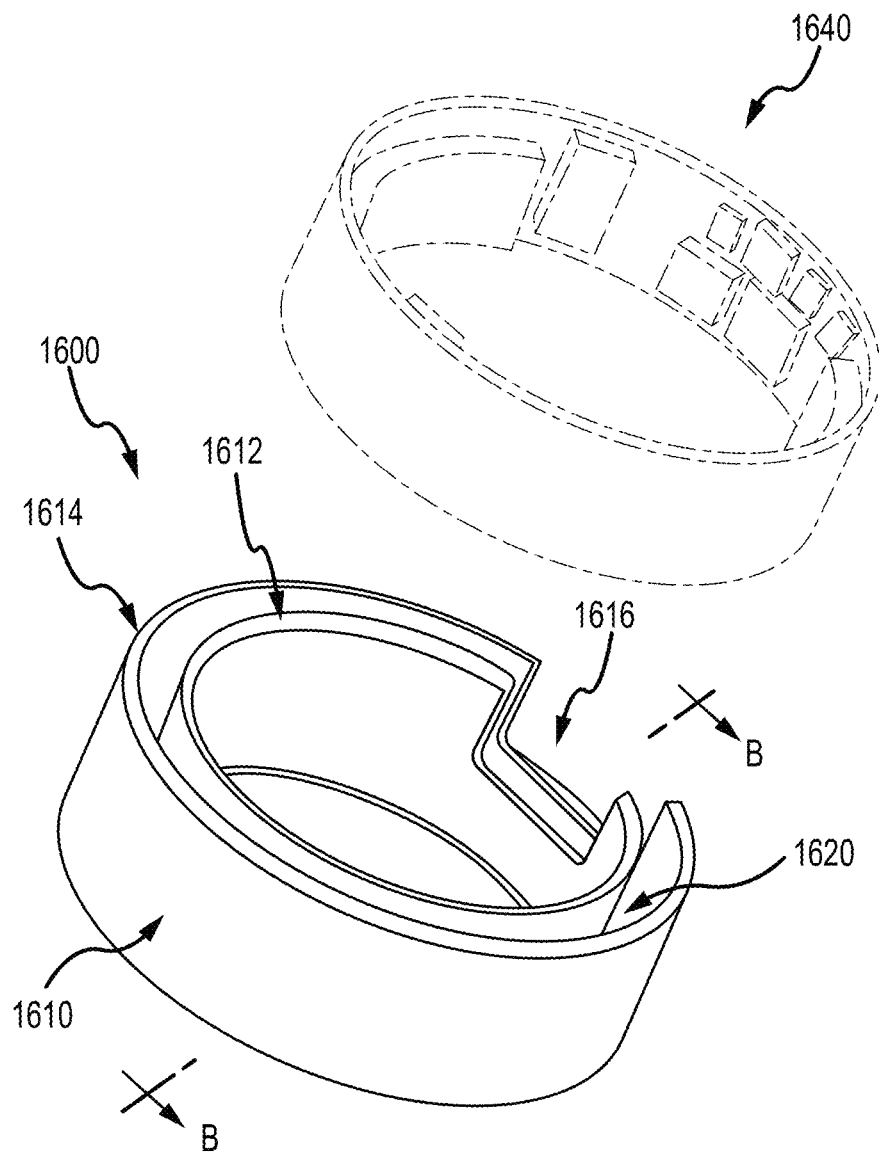
FIG. 16A is an exploded view of a housing and a PCB of a WCD according to one or more aspects of the disclosure.

FIG. 16A is an exploded view of a housing 1610 and a PCB of a WCD according to one or more aspects of the disclosure. The WCD 1600 comprises a housing 1610 with an integral inner wall and outer wall 1612 and 1614. The housing can be made of any material, such as any material described above with respect to the internal/external housing structures. In this example, the inner and outer walls 1612, 1614 each define a window in the shape cutaway portions 1616. The cutaway portions are bounded on three sides by the walls 1612 and 1614 and unbounded at the other side thereof. The cutaway portions 1616 can be aligned with one another to ensure transmission of radiation into/out of the housing 1610. The space 1620 between the inner and outer walls 1612,1614 can receive a PCB 1640, battery, components, etc.

Figure 16B:
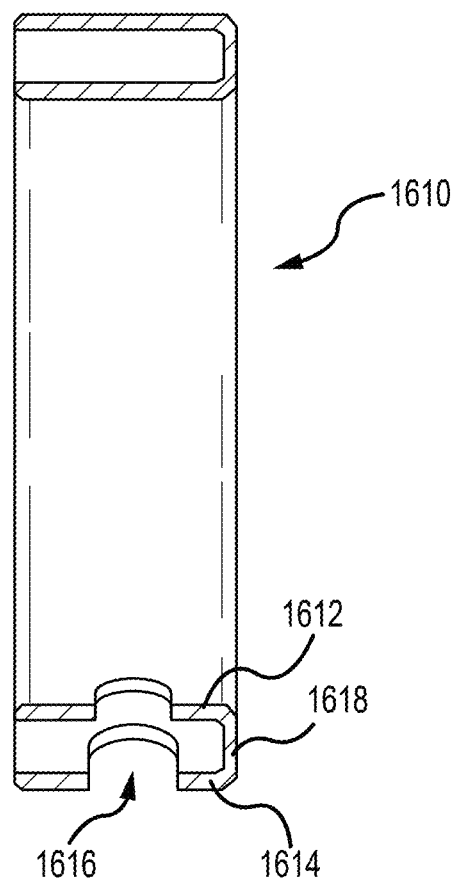
FIG. 16B is a cross section of FIG. 16A along line B-B.

FIG. 16B is a cross section of FIG. 16A along line B-B. As shown, the inner and outer walls 1612,1614 are directly connected by a floor 1618. The space 1620 is defined by the space between the inner and outer walls 1612,1614 and the floor 1618.

Figure 16C:
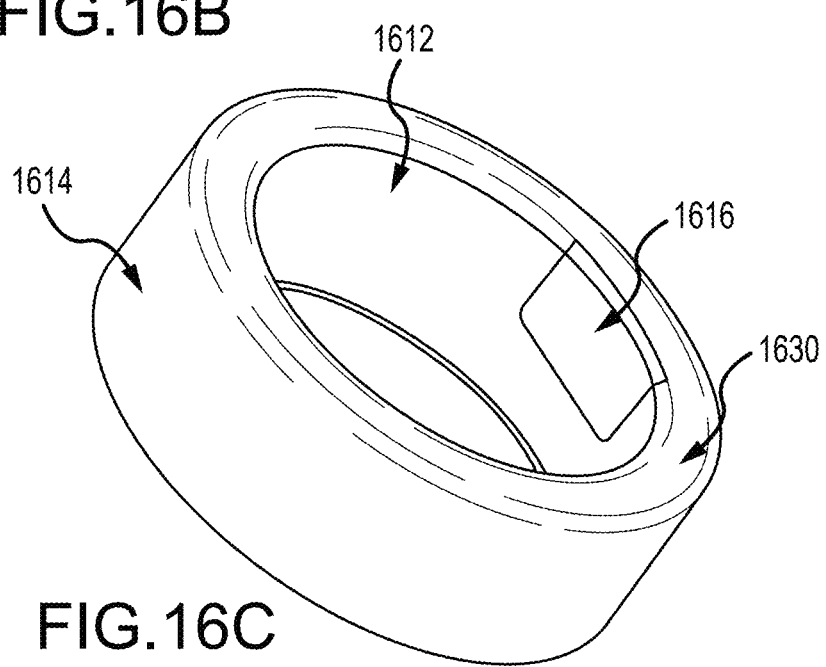
FIG. 16C is a perspective view of the WCD with potting material.

FIG. 16C is a perspective view of the WCD with potting material 1630. As described above, the PCB, battery, and components can be disposed within the space. Once disposed therein, a potting 1630 can be provided atop the components and within the cutaway portion 1616. The potting 1630 can be transparent to allow for transmission of light through the cutaway portions 1616.

V. CHARGING BY CONCENTRATED LIGHT SOURCE

According to one aspect of the disclosure, the WCD can be charged by an external concentrated light source, e.g., laser light, laser diode, etc. In this regard, the photovoltaic device described above can include a concentrated photovoltaic element (CPV) that is constructed and arranged to receive concentrated light from the concentrated light source, e.g., laser light from a laser diode, light from a light emitting diode (LED), etc., and converting the received concentrated light into an electric current. The photovoltaic device can also generate power from nonconcentrated light sources, such as office lighting and ambient sunlight. The electric current can be used to charge one or more batteries stored within the housing of the WCD.

Figure 17A:
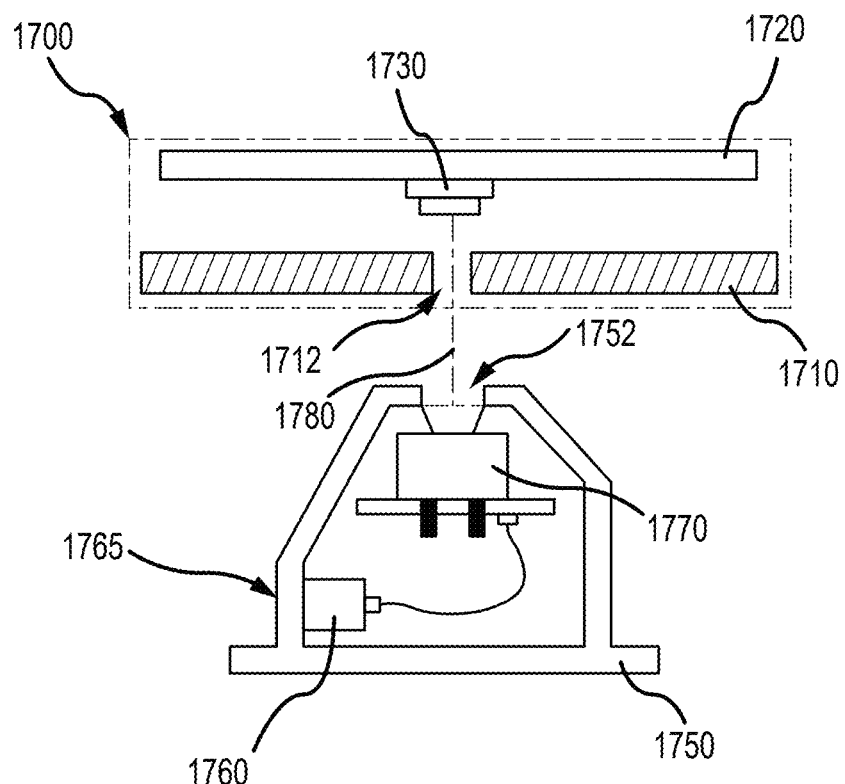
FIG. 17A depicts a cross section of a WCD employing charging by concentrated light source according to one or more aspects of the disclosure.

FIG. 17A depicts a cross section of a WCD employing charging by concentrated light source according to one or more aspects of the disclosure. In this example, the WCD 1700 can include a housing material 1710. The WCD can include a PCB 1720 and a concentrated photovoltaic cell 1730. The WCD can be positioned adjacent a base assembly or base station 1750. The base assembly 1750 can be connected to an external power source 1765 and can have internal circuitry 1760 to power one or more concentrated light sources 1770, e.g., one or more laser diodes and/or one or more LEDs, disposed within the base assembly 1750. In this example, the concentrated light source 1770 comprises one or more laser diodes.

The base assembly 1750 can define a first opening 1752 at one portion thereof to allow the concentrated light 1780 to exit the housing of the base assembly I 750. As shown in the diagram of FIG. 17A, the concentrated light 1780 is generated by the concentrated light source 1770 and exits the housing of the base assembly 1750 via a first opening 1752. The concentrated light 1780 then enters into the WCD by a second opening 1712 in the housing of the WCD 1700 where it can fall upon the CPV 1730. Once the concentrated laser light falls upon the CPV 1730, the CPV 1730 can convert the incident concentrated light into a current that can be used to directly power one or more components within the WCD and/or can be used to charge one or more rechargeable batteries onboard the WCD.

The concentrated light source 1770, as described above, can be any type of light source that is arranged to generate concentrated light, such as an LED or a laser diode. The concentrated light can be any type of concentrated and/or coherent electromagnetic radiation, such as laser light and/or LED light. The concentrated light can have any desired intensity or wavelength, according to the characteristics of the CPV 1730.

In one example, the source 1770 can be a 200 mW laser diode that produces red or green laser light. This can generate approximately 80 mW (or typically less) of power in the WCD where the CPV 1730 includes a plurality of groups of photovoltaics configured in series or in parallel with one another. Each group of photovoltaics can include one or more CPV cells. In another example, the CPV can include a single group of photovoltaics.

The base assembly 1750 described above can include additional components that can interact with the WCD 1700. For example, the base assembly can include one or more antennas that can communicate according to one or more wireless protocols, such as 3G, 4G, WiFi, Bluetooth®, NFC, or the like, for direct or indirect wired or wireless communication with the WCD or mobile device. In addition to the charging methods above, the base assembly can employ inductive charging techniques.

Figure 17B:
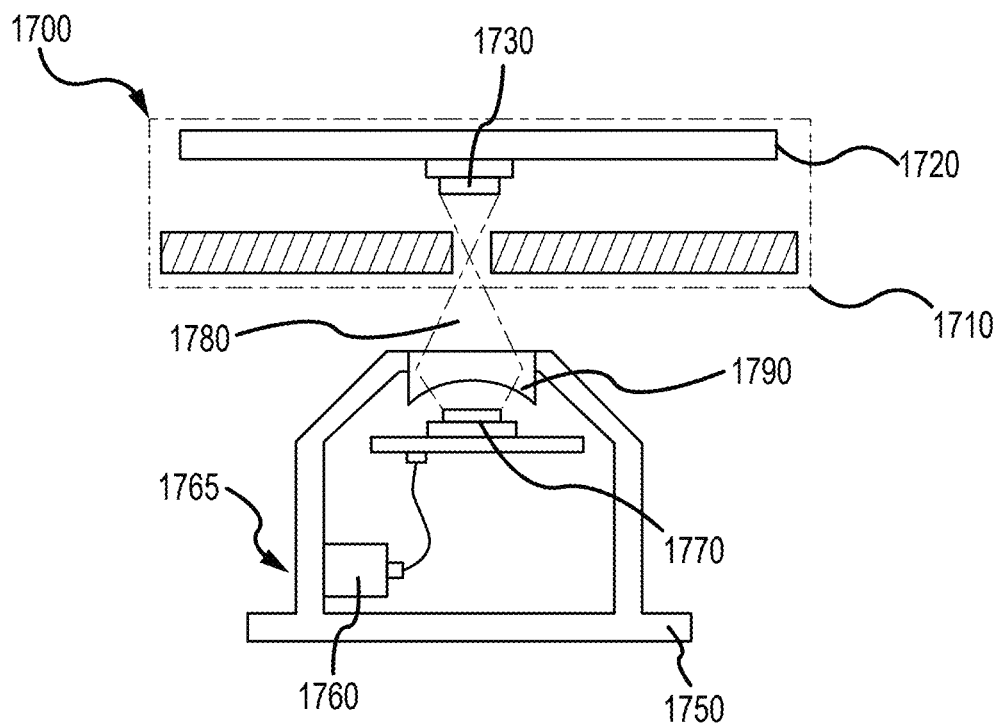
FIG. 17B depicts a cross section of a WCD employing charging by concentrated light source according to another aspect of the disclosure.

FIG. 17B depicts a cross section of a WCD employing charging by concentrated light source according to another aspect of the disclosure. In this example, the concentrated light source 1770 comprises an LED. Further, the base assembly comprises an optical element 1790 positioned adjacent to the concentrated light source I 770 for focusing the LED light onto the CPV inside the WCD. The optical element 1790 can be any type of optical element, such as a lens. The lens can be formed of any material, such as glass, plastic, etc., and can be any type of lens, such as concave, convex, piano-concave, piano-convex, etc. In this example, the optical element 1790 includes a piano-concave, with the concave portion facing the concentrated light source 1770. In the example where the source 1770 is an LED, the LED emits light in many directions. The optical element 1790 can focus the emitted LED light to focus as much of the LED light as possible onto the CPV of the WCD. The optical element 1790 can be disposed at least partially or completely within the first opening 1752. In some implementations, the optical element may not be necessary due to LEDs with substantially focused light.

Figure 17C:
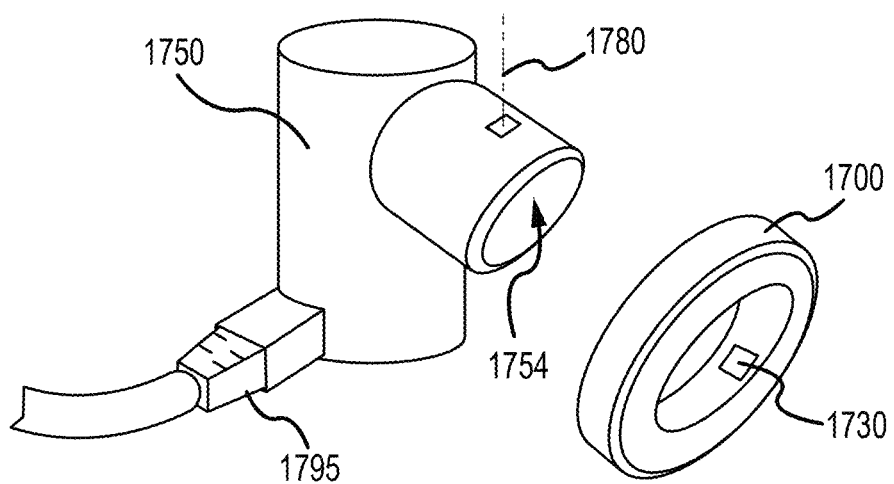
FIG. 17C is a perspective view of a base assembly and WCD 700 according to one or more aspects of the disclosure.

FIG. 17C is a perspective view of a base assembly 1750 and WCD 1700 according to one or more aspects of the disclosure. As shown, the WCD 1700 is in the shape of a ring and the base assembly 1750 includes a post 1754 for receiving the ring. The post 1754 can be cylindrical and can be sized and shaped according to an internal diameter of the WCD in order for the WCD to be received on an external surface of the post. The first opening 1752 of the base assembly 1750 is formed on a portion of the post 1754 such that, when the WCD 1700 is stored on the post, the second opening 1712 can be aligned with the first opening 1752 to ensure alignment of the CPV and the concentrated light source. The base assembly can receive/transmit power and/or data via external input/output 1795, which can be a DC power input, a USB input connection or any other acceptable connection/form factor.

Figure 17D:
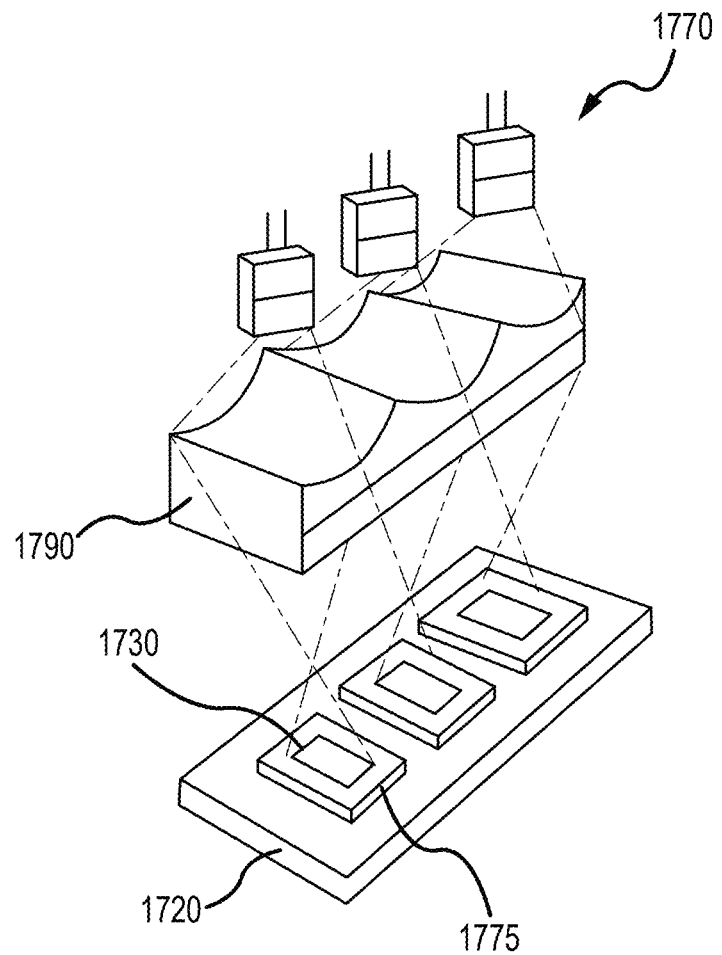
FIG. 17D depicts a perspective view of internal components of the base assembly 750 and WCD 700 according to another aspect of the disclosure.

FIG. 17D depicts a perspective view of internal components of the base assembly 1750 and WCD 1700 according to another aspect of the disclosure. In this figure, the respective housings of the base assembly and WCD have been omitted, thereby showing a plurality of concentrated light sources 1770, optical elements 1790, and a plurality of CPVs 1730 disposed on mounting substrates 1775 on a PCB. In this example, the WCD can include a plurality of CPVs and the base assembly can include a plurality of sources. This allows for a greater current to be generated during charging and for faster charging times of the WCD. The CPVs and concentrated light sources can correspondingly be disposed in a line, with a constant or variable pitch between respective elements. In this regard, the optical element can include corresponding concavities with the same pitch.

FIGS. 17E-F depicts other CPV configurations according to one or more aspects of the disclosure. As shown in FIG. 17E, the CPVs 1730 can be arranged in a 1×4 array, while FIG. 17F depicts the CPVs arranged in a 2×2 array. In addition to the examples shown in the above figures, the WCD can include any number of CPVs according to any number of geometric configurations.

FIG. 17G is perspective view of a WCD and base assembly with a 1×3 CPV arrangement. As shown, the WCD can include a 1×3 array of CPVs and the base assembly can include a corresponding 1×3 array of concentrated light sources. As indicated by the arrow, a user can then rotate the WCD on the base assembly in order to align the respective first and second openings, as well as the CPV and concentrated light sources.

Figure 18A:
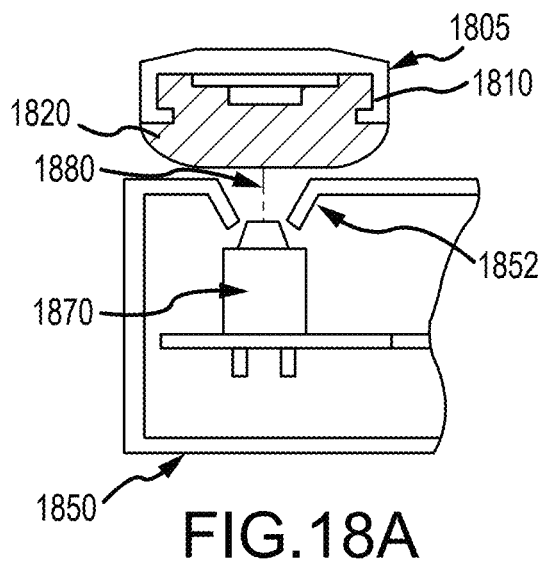
FIG. 18A depicts a cross section of a WCD 800 employing charging by concentrated light source according to another of the disclosure.

FIG. 18A depicts a cross section of a WCD 1800 employing charging by concentrated light source 1870 according to another aspect of the disclosure. In this example, the WCD includes an internal/external housing portion 1810 and an internal/external potting portion 1820, as described above. In this regard, the base assembly 1850 includes a first opening 1852, but is free of a second opening on the WCD. The concentrated light 1880 passes through the transparent potting portion and falls incident upon the CPV cell 1830. In this example, the source can be a laser diode.

Figure 18B:
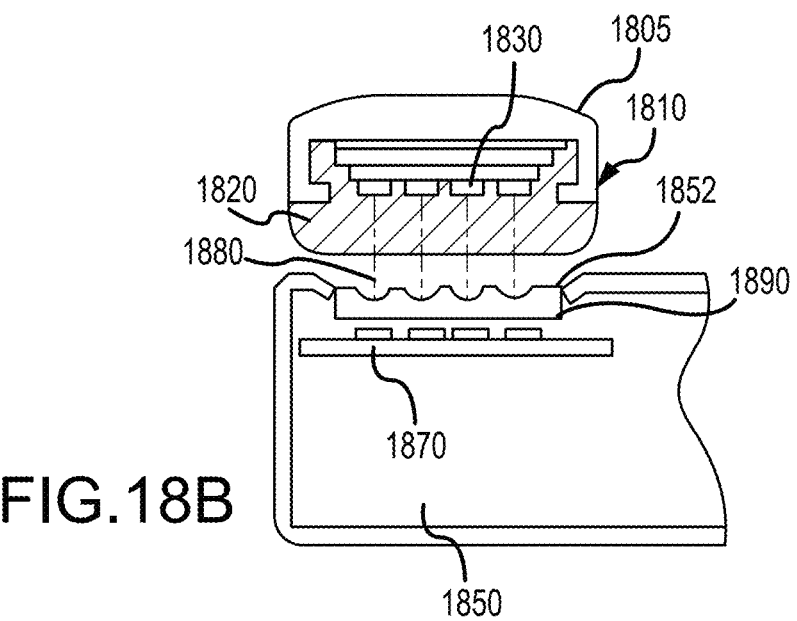
FIG. 18B depicts a cross section of a WCD employing charging by concentrated light source according to another of the disclosure.

FIG. 18B depicts a cross section of a WCD employing charging by concentrated light source according to another of the disclosure. In this example, the concentrated light source 1870 includes one or more LEDs and the base includes one or more optical elements 1890 for focusing the concentrated light 1880. The LEDs may be of different wavelengths to provide power to two or more junctions in the triple junction CPV cell.

Figure 19A:
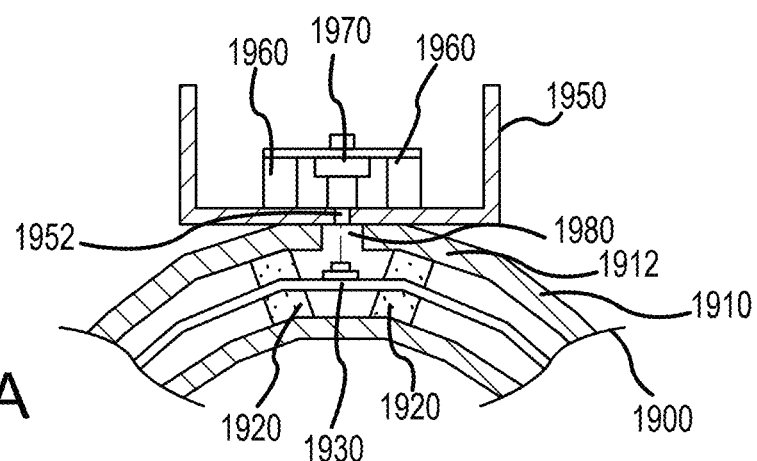
FIG. 19A depicts a cross section of a WCD employing charging by concentrated light source according to another of the disclosure.

FIG. 19A depicts a cross section of a WCD 1900 employing charging by concentrated light source 1970 according to another of the disclosure. In this example, the WCD and/or the base assembly 1950 can employ one or more magnetic and/or ferrous materials to ensure alignment between the concentrated light source and the CPV cell. Such alignment can improve charging efficiency of the WCD.

The base assembly includes a first opening 1952 and the WCD includes a second opening 1912 to allow for concentrated light to fall incident upon the CPV 1930. In this example, the second opening is formed on an external housing portion of the WCD. In this arrangement, the base assembly can charge the WCD from an exterior of the WCD, rather than an internal charging method as identified above.

The WCD can include a ferrous or other suitable (e.g. ferromagnetic) material 1920, such as steel, disposed within the housing 1910. In this example, the ferrous material is disposed in a space defined between an internal housing and an external housing. The ferrous material can surround the CPV.

The base assembly can include corresponding magnets 1960 that can cause an attractive force between the WCD and the base assembly into an optimal configuration for charging. The magnets can be disposed within the base assembly and can surround the concentrated light source. The magnets 1960 can be formed of a rare earth material, such as neodymium or any other acceptable material that provides a requisite magnetic field strength.

Figure 19B:
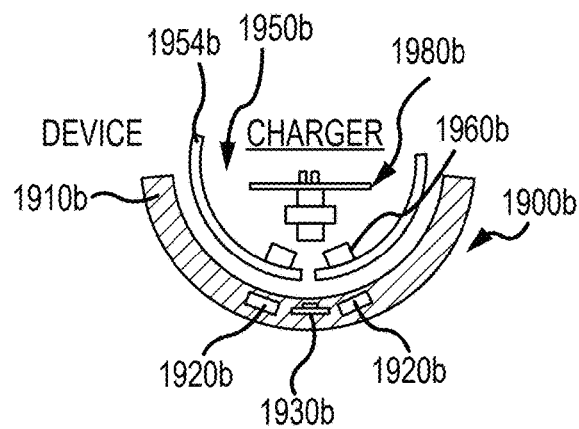
FIG. 19B depicts a cross section of a WCD employing charging by concentrated light source according to another of the disclosure.

FIG. 19B depicts a cross section of a WCD 1900b employing charging by concentrated light source 1980b according to another of the disclosure. The CPV 1930b of the WCD 1900 is charged from an interior portion, such as by a base assembly 1950b with a post 1954b. Similarly, the WCD can include a ferrous material 1920b disposed within the housing 1910b and the base assembly 1950b can include a magnet 1960b.

Figure 19C:
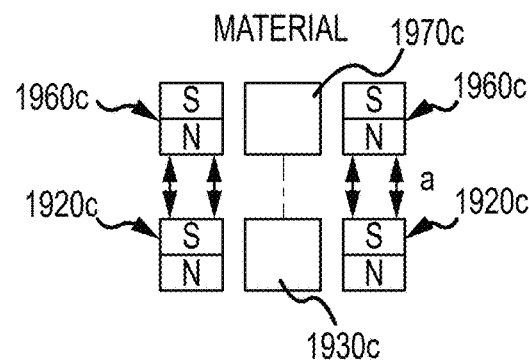
FIG. 19C depicts a schematic diagram of magnets that can be used in a WCD and/or base assembly according to one or more aspects of the disclosure.

FIG. 19C depicts a schematic diagram of magnets 1920c, 1960c that can be used in a WCD and/or base assembly, including a CPV 1930d and concentrated light source 1930d, according to one or more aspects of the disclosure. As shown, the magnets and/or ferrous/ferromagnetic materials can be axially polarized, with each having a respective north pole and south pole. In this regard, the WCD can have axially polarized magnets 1920c with a south pole S facing toward the base assembly, and the base assembly can have axially polarized magnets 1960c with a north pole N facing toward the WCD. The attractive force between the north and south poles can ensure alignment of the CPV 1930c of the WCD and the source 1970c base.

Figure 19D:
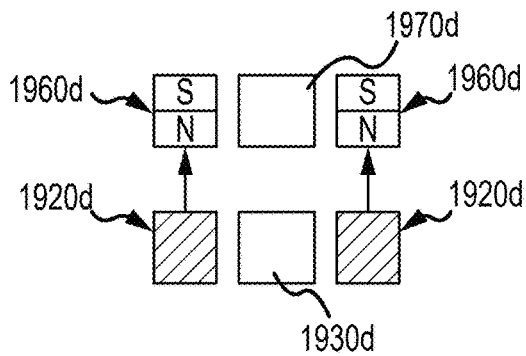
FIG. 19D depicts a schematic diagram of magnets that can be used in a WCD and/or base assembly according to one or more aspects of the disclosure.

FIG. 19D depicts a schematic diagram of magnets that can be used in a WCD and/or base assembly according to one or more aspects of the disclosure. In this example, the base assembly includes axially polarized magnet 1960d, with a north pole N facing toward the WCD. The WCD can include ferrous steel 1920d, with an attractive force between the ferrous steel and the north pole of the base assembly magnet.

Figure 19E:
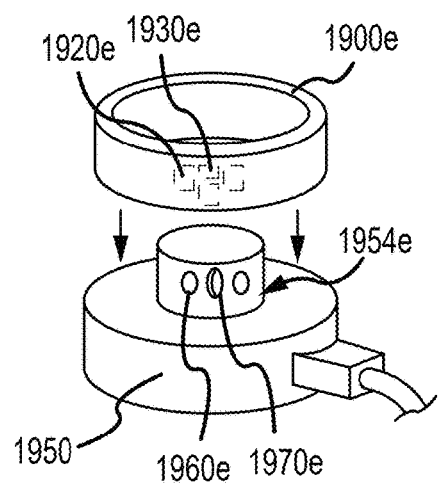
FIG. 19E is a perspective view of a WCD and a base assembly according to one or more aspects of the disclosure.

FIG. 19E is a perspective view of a WCD and a base assembly according to one or more aspects of the disclosure. As shown, the WCD 1900e can be received by a post 1954e of a base assembly 1950e. The respective magnets 1960e and/or ferrous materials 1920e are shown in phantom to illustrate their positioning with respect to the WCD and base assembly devices and the CPV 1930e as well as the concentrated light source 1970e.

Figure 20A:
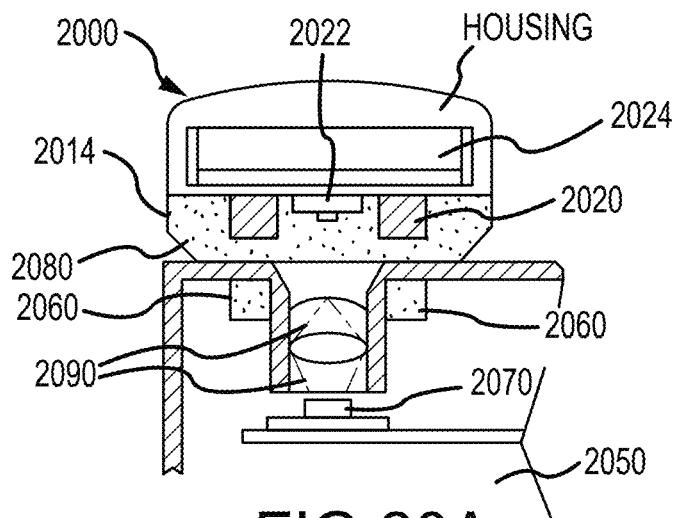
FIG. 20A is a cross section of a WCD engaged with a base assembly 1050 according to one or more aspects of the disclosure.

FIG. 20A is a cross section of a WCD 2000 engaged with a base assembly 2050 according to one or more aspects of the disclosure. In this example, the magnets 2060 can surround the concentrated light source 2070, and the WCD can include a ferrous steel 2020, CPV 2022, and battery 2024 disposed within an internal/external potting 2014 of the WCD. The ferrous steel 2020 can be disposed on a face of the PCB 2040 and can be encapsulated by the internal/external potting 2014. The base assembly can include one or more optical elements 2090 for focusing the concentrated light 2080.

Figure 20B:
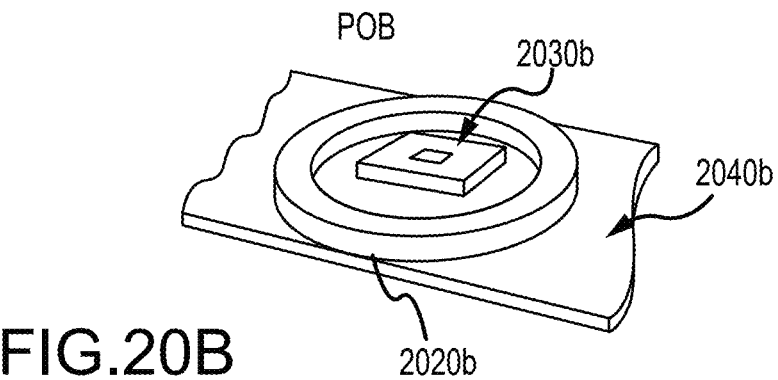
FIG. 20B is a perspective view of a PCB 1040*b* with a CPV 1030*b* and ferrous element 1020*b* configuration according to one or more aspects of the disclosure.

FIG. 20B is a perspective view of a PCB 2040b with a CPV 2030b and ferrous element 2020b configuration according to one or more aspects of the disclosure. In this example, the ferrous element 2020b comprises a steel ring that can surround a CPV 2030b and can be disposed on the PCB 2040b.

Figures 20C, 20D:
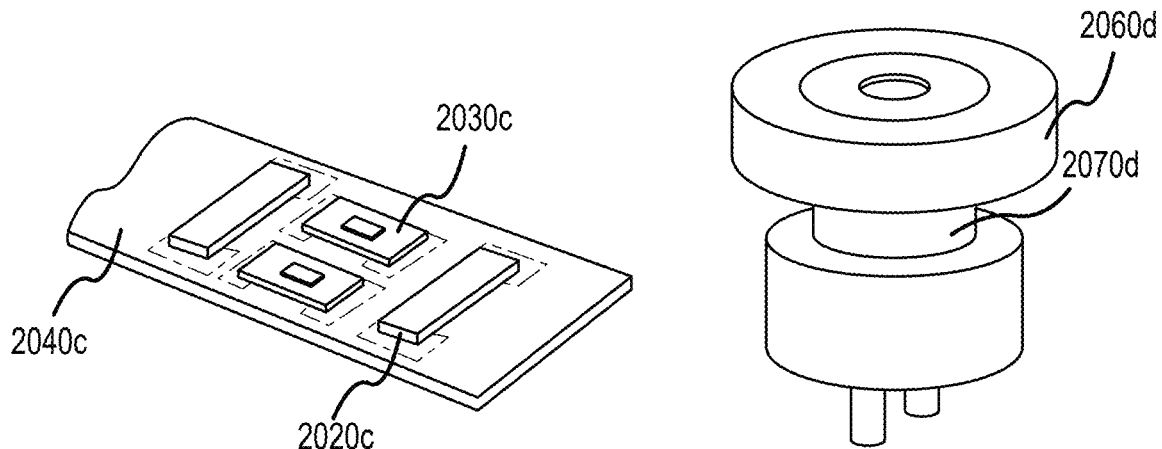
FIG. 20C is a perspective view of a PCB with a CPV 1030*c* and ferrous element 1020*c* configuration according to one or more aspects of the disclosure.
FIG. 20D is a perspective view of a magnet and a concentrated light source 1070d according to one or more aspects of the disclosure.

FIG. 20C is a perspective view of a PCB 2040c with a CPV 2030c and ferrous element 2020c configuration according to one or more aspects of the disclosure. In this example, the ferrous element 2020c comprises a plurality of rectangular bars disposed on the PCB. In this way, the ferrous element 2020c can be coated to be reflowed onto the PCB.

FIG. 20D is a perspective view of a magnet 2060d and a concentrated light source 2070d according to one or more aspects of the disclosure. As shown, the magnet 2060d can include a ring that can extend around a circumference of the concentrated light source 2070d. The magnetic ring can be attracted to the ferrous steel ring and/or the rectangular ferrous steel examples set forth in 20A-C above.

In some examples, the WCD can be adapted to uniquely identify the wearer of the WCD using, for example biometric features unique to the user.

Figure 21A:
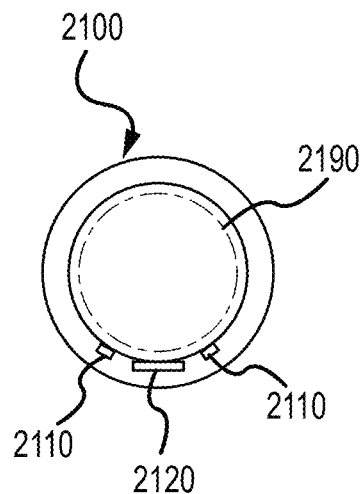
FIG. 21A is a schematic view of a WCD showing components used for identifying the wearer of the WCD.
Figure 21B:
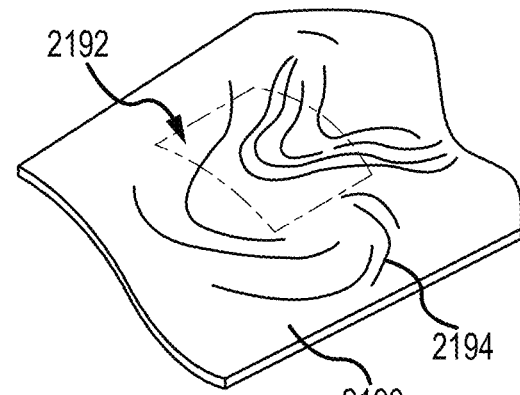
FIGS. 21B-C are perspective views of a skin surface according to one or more aspects of the disclosure.
Figure 21C:
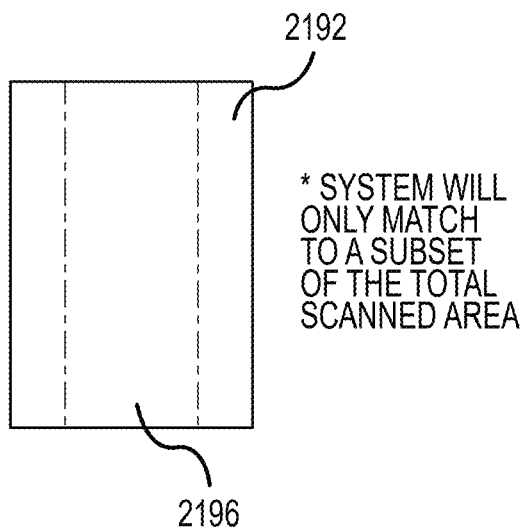

FIG. 21A is a schematic view of a WCD 2100 showing components used for identifying the wearer of the WCD. As shown, the WCD 2100 can include one or more infrared illumination sources 2110 and an infrared CMOS imaging device 2120. The finger 2190 can extend through the finger space of the WCD and the IR source 2110 can illuminate a portion of the skin of the finger 2190. The IR CMOS imaging device 2120 can receive light that has been reflected from the skin surface and produce an image of the skin of the finger 2190. As shown, the IR source 2110 and the imaging device 2120 are positioned near the interior surface of the WCD, e.g., the surface facing the skin of the finger. The IR illumination can pass through a window provided on the interior housing or can pass through a transparent potting material.

During the imaging process, the WCD 2100 can be rotated about an axis passing through the center of the finger space and along the longitudinal direction of the finger. In this regard, the imager 2120 can capture a larger swath of the skin surface than if the WCD 2100 were held stationary with respect to the finger during the imaging process.

At the time of first use, or any time thereafter, the user can generate a reference capillary map in order to identify himself/herself as the authorized user of the WCD. As described above, the user can rotate the WCD around the finger to capture image data of an analyzed section of skin 2192 and on or more capillaries 2194 of the user currently wearing the WCD. The image data can correspond to an overall analyzed section of the skin 2196 of the wearer. The image data of the capillaries can be used to generate a reference capillary map of the wearer, which can be stored in the memory, such as flash memory or EEPROM, of the WCD.

When the same user puts the WCD on his or her finger after generation of the reference capillary map, the WCD can capture image data of the wearer's skin surface that can be compared to the reference capillary map stored in the memory. In this regard, the user need not rotate the device around the finger. Instead, the WCD can compare a subset of the gathered image data to a corresponding subset of reference capillary map. If there a match, within a predetermined error tolerance, the WCD can uniquely identify the wearer as an authorized user of the WCD and as the unique individual who generated the reference capillary map. Once authorized, the wearer can have access to certain functions, features, data, or other content that is not otherwise available without authorization. In another example, the identification can be a step in a transaction or other type of authorization, such as an electronic payment, bank transaction, etc. If the gathered data does not match the reference capillary map, then the user may be prevented from accessing certain features on the WCD.

Illustratively, the comparison process between sensed capillaries and some or all of the capillary map can be implemented using basic pattern recognition algorithms (processes) instantiated in the electronics of the WCD. Such processes can rely on edge detection and similar techniques that should be clear to those of skill in the art and can be sourced from various commercial vendors of biometric recognition software.

In another example, the illumination can include NIR illumination and can project radiation into the skin of the finger. The reflected NIR illumination can then be analyzed to determine one or more characteristics of the blood, such as blood alcohol levels, blood glucose levels, and blood oxygenation levels. In this regard, the WCD analyzes the reflected radiation to identify wavelengths that were absorbed from the projected radiation by the blood of the user. Techniques and processed used in conjunction with commercially available venous oximeters (for example) can be employed to undertake certain readings.

FIG. 22A is a perspective view of a user employing ECG monitoring according to one or more aspects of the disclosure. In this example, the user can wear the WCD 2200 on a first finger 2210 of first hand 2220, and can touch a second finger 2230 of a second hand 2240 to an exterior surface of the WCD 2200. This can provide an electric pathway 2250 through the body, as shown in FIG. 22B, allowing for the transmission of electrical current between distant portions of the body.

FIG. 22C is a perspective view of a WCD that can employ ECG monitoring according to one aspect of the disclosure. In this example, the WCD 2200 includes an internal/external housing 2250 with a conductive pad 2260. The conductive pad 2260 can be electrically isolated from the external/internal housing 2250 of the WCD, thereby providing distinct and isolated electrical contacts on the WCD. The internal/external housing 2250 can be in electrical communication with the first finger 2210 of the first hand, while the conductive pad 2260 can be in electrical communication with the second finger 2230 of the second hand. In this regard, an electrical path 2250 is formed through the respective hands 2220, 2240 and through the rest of the user's body, particularly through the chest. In this regard, the WCD can take various electrical measurements of the user, such as ECG. The ECG measurement can include measurements of the various waveforms, such as P-U waveforms. The WCD can store such ECG data in a memory and/or can communicate the data to a wirelessly connected mobile device. In another example, the WCD can employ electrically isolated internal and external housings, such as those described above. In this regard, the conductive pad may not be utilized, and the user can wear the WCD on a first finger and apply the second finger anywhere on the external housing.

The WCD can also serve as a monitor for those who are mobility impaired or who are prone to falls, such as disabled persons and/or retired persons. The accelerometer onboard the WCD detect a fall of the user via a sudden change in acceleration data. The WCD, in conjunction with a mobile device and/or one or more base stations positioned around the home of the user, can determine the position of the user within the house. For example, the mobile device can employ GPS capabilities, and either the mobile device or the base stations can use GPS in combination with WiFi signal strengths to determine the location of the user within the house. The WCD can then issue an alert, either directly or indirectly (via the mobile device or base station) to a third party that a fall has occurred. The alert can be a phone call, text message, e-mail, or any other type of communication. The third party can then take appropriate measures to aid the fallen user.

The WCD can also monitor heart rate and/or temperature, in addition to the other monitored characteristics described above. If any of the monitored characteristics is abnormal, e.g., measured parameters outside of a predetermined threshold range, an alert can be sent to a third party. In some examples, the third party can be a medical health professional, such as a doctor, nurse, caretaker, etc. It is noted that, for those embodiments which can function as a cardiac monitor (e.g., that measures electrocardiogram (EKG)), it can be necessary to establish a closed loop (e.g., for the electrical measurement of EKG) across the heart. As such, in some of those embodiments, a separate conductive pad or other skin-contacting structure/probe can be coupled to the WCD so that a user can pinch the pad with fingers on an opposite hand.

Since the WCD has the form factor of a ring, the WCD is designed to be worn over long periods of time by a user with little to no discomfort or interference. In this regard, the WCD can monitor the above-described, monitored characteristics over long periods of time (e.g. weeks, months, etc.), and determine trends in the data. For example, the WCD can measure heart rate over a long period of time and determine a unique resting heart rate for a user. If the user's heart rate deviates from the resting heart rate, the WCD can be arranged to issue an alert to a third party. In one specific example, the WCD can use appropriate processes to analyze both the trends of monitored characteristics, as well as current accelerometer data. In this way, if a person's heart rate deviates from a resting heart rate, but the accelerometer indicates that the user is exercising and/or engaging in strenuous activity that provides an equivalent workout, then the WCD may not issue an alert in this circumstance.

Figure 23A:
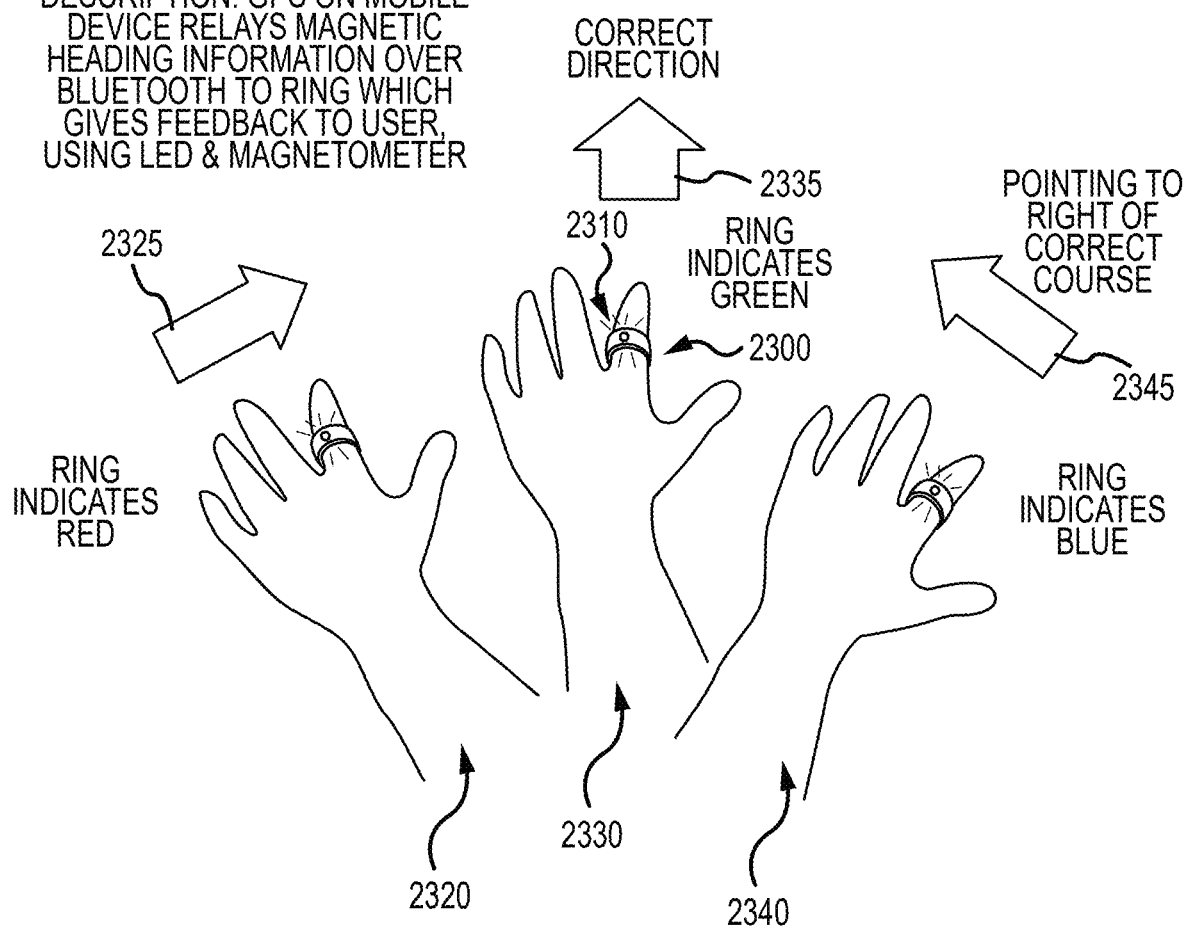
FIG. 23A is a perspective view of the hand of a user in various positions employing the navigational features of the WCD.

FIG. 23A is a perspective view of the hand of a user in various positions employing the navigational features of the WCD. As described above, the WCD can communicate with a mobile device though one or more wireless communication protocols. The mobile device can include a processor and a memory and can execute a map application/process that can provide turn-by-turn walking or driving directions to the user based on the user's GPS location. A portion of those directions can include information regarding heading, distance to travel at that heading, waypoints, and the direction of next turn. By way of the wireless communication, the mobile device can communicate one or more of pieces of information relating to directions, such as the heading. Once the heading is received the WCD, the WCD can give feedback to the user regarding the actual heading measured by the onboard magnetometer and the heading set forth in the direction information. In one example, the feedback can be haptic or physical feedback provided by one or more actuators, such as the actuators 670 described above.

FIG. 23A depicts a user's hand in various positions of navigation, each hand including a WCD worn thereon. In this example, the heading provided by the mobile device is the heading 2335, which represents the direction in front of the hand position 2330. In this regard, if the user gestures, e.g., points a ring finger, in the direction of the correct heading, the WCD 2300 can give feedback to the user indicating the correct heading. The feedback can include, for example, an LED indicator 2310 showing a green visible light. In the example of hand position 2320, the finger is gesturing in a direction to the left of the correct course 2325. In this way, the WCD 2300 can provide feedback to correct the heading of the user. Such feedback can include illumination of an LED indicator showing (e.g.) a red visible light. Similarly, hand 2340 is gesturing in direction 2345, which is to the right of the correct/appropriate direction. The WCD can provide (e.g.) a blue indicator informing the user to change heading.

Figure 23B:
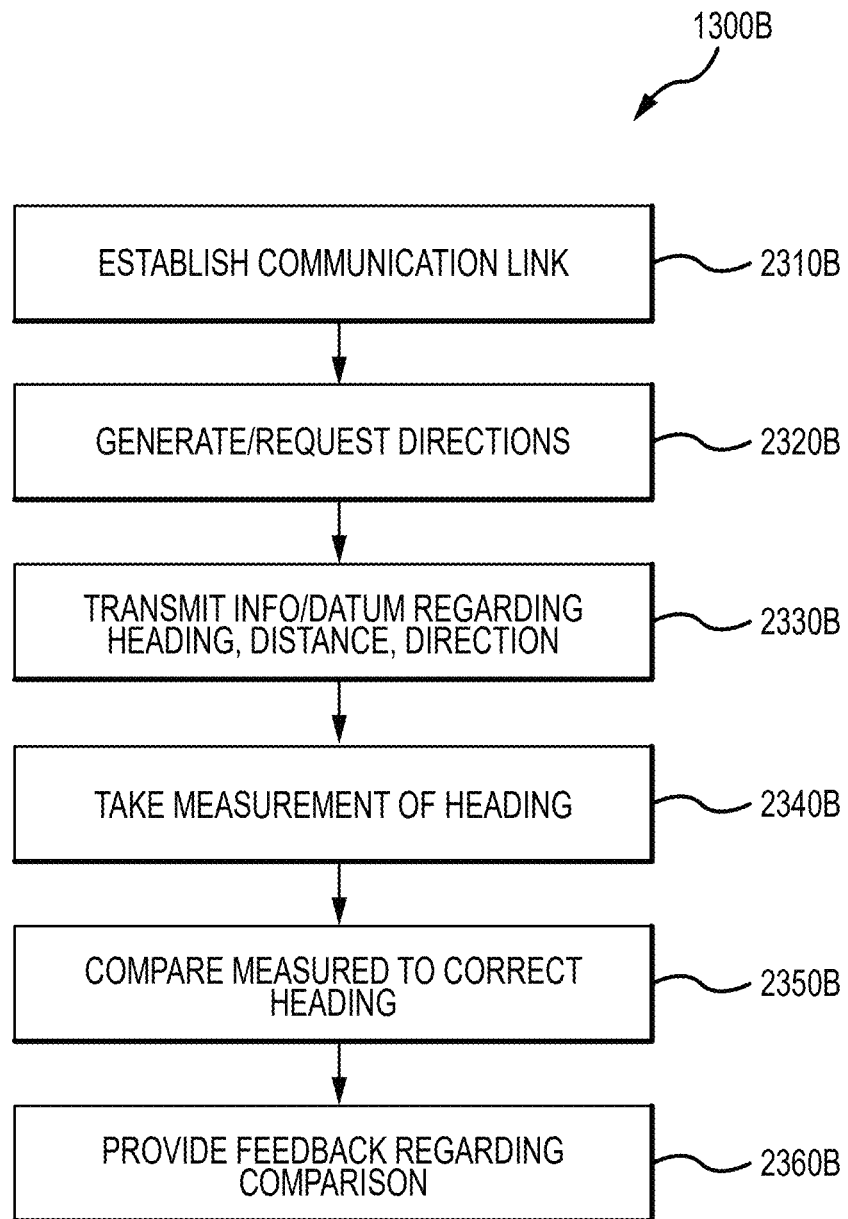
FIG. 23B is a flow chart depicting a method of providing feedback to a user according to one or more aspects of the disclosure.

FIG. 23B is a flow chart 2300B depicting a method of providing feedback to a user according to one or more aspects of the disclosure. At block 2310B, a user can establish a communication link between a WCD and a mobile device. At block 2320B, the user can generate or request a set of directions at the mobile device, including information/data regarding heading, distance to travel at that heading, and the direction of next turn. At block 2330B, the mobile device can transmit at least one of the information items/datum regarding heading, distance to travel at that heading, and the direction of next turn. At 2340B, the WCD can take a measurement of heading by measuring a heading associated with an explicit gesture by the user's finger donning the ring. Such gesture can include pointing in a proposed heading of travel. At block 2350B, the WCD can compare the measured or proposed heading to the correct heading provided by the mobile device. At 2360B, the WCD can provide feedback to the user based on the comparison at 2350B, e.g., if the user is gesturing in the correct direction, a green LED indicator may appear. In other examples, if the gesture is in a direction that does not correspond with the correct direction, a (e.g.) blue or red indicator can appear. In one specific example, indicators representing left and right course alterations can be different so a user can easily discern a correct direction of travel.

Figure 24A:
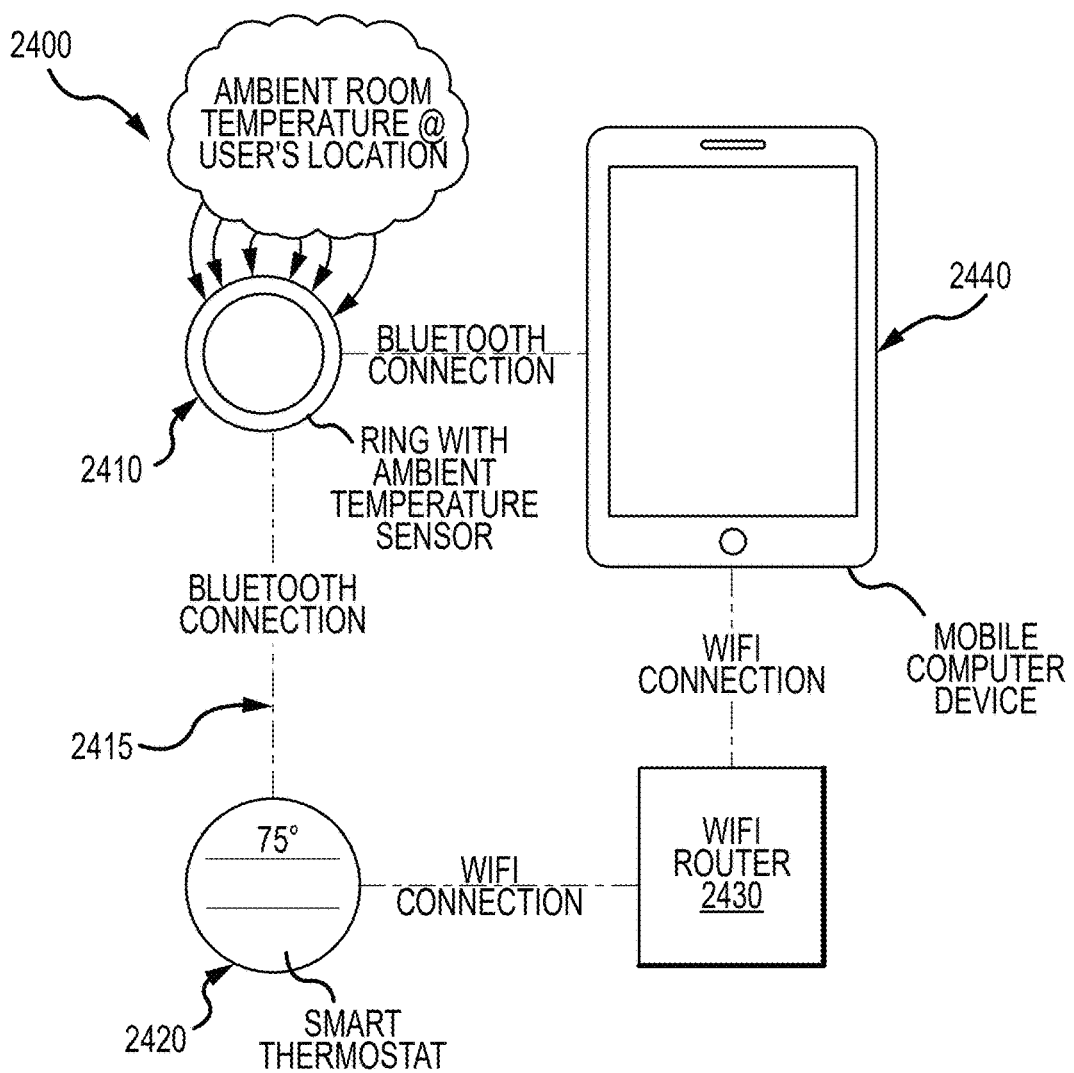
FIG. 24A is a schematic diagram of a system 1400 for controlling an environment of a user according to one or more aspects of the disclosure.

FIG. 24A is a schematic diagram of a system 2400 for controlling an environment of a user according to one or more aspects of the disclosure. As shown, the WCD can be connected, wired or wirelessly, to one or more appliances in the home of a user. The system 2400 can include a WCD 2410, a thermostat 2420, a wireless access point (e.g., WiFi router) 2430, and a mobile device 2440. The WCD can be wirelessly connected (e.g., link 2415) to both the thermostat and the mobile device by any type of wireless communication protocol, such as Bluetooth. The access point can be wirelessly connected to the thermostat and the mobile device by any type of wireless communication protocol, such as WiFi. It is noted that a wide range of commercially available appliances, thermostats, lighting controllers, home controllers, and the like, can interface with the WCD using WiFi or another conventional/proprietary communication protocol, as described further below.

Figure 24B:
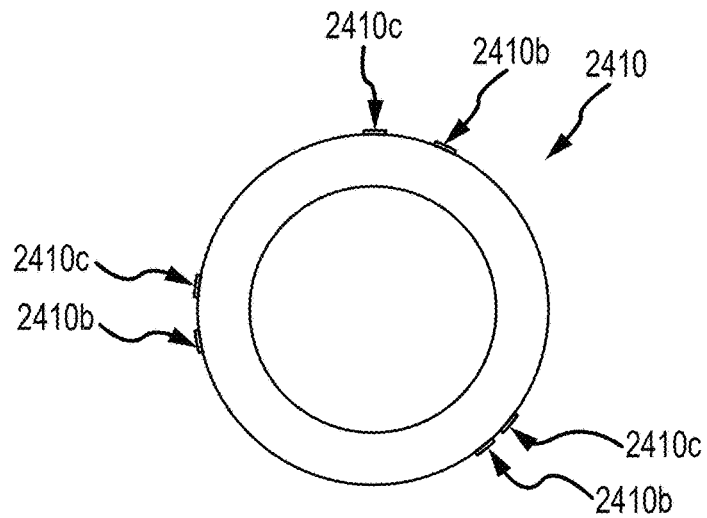
FIG. 24B is a side view of a WCD showing one or more temperatures sensors according to one or more aspects of the disclosure.

The WCD 2410 can include one or more temperature sensors. In one example, the WCD can include at least one internal facing temperature sensor 2410a and an at least one outward facing temperature sensor 2410b, as shown at FIG. 24B. The inward facing temperature sensor 2410a can be near the skin of a user when the user is wearing the ring, and can therefore measure the skin temperature of the user. The outward facing temperature sensors 2410b can be disposed away from the finger of the user, and can therefore be arranged to measure an ambient temperature of the room in which the user currently resides with sufficient thermal isolation from the user's hand and his/her body heat. In particular, in order to ensure accurate ambient temperature measurements, the WCD can employ a combination of multiple light sensors 2410c and outward facing temperature sensors 2410b. In this regard, the temperature sensor 2410b associated with the light sensor 2410c that receives the most light can be the most accurate, as it is most likely that this sensor is furthest from the finger or palm of the user. In another example, the WCD can employ multiple outwardly facing temperature sensors 2410b and compare the temperature values of each to the inward facing sensor 2410a. The WCD can then select the most accurate temperature value from the outward facing sensors.

Based on the measured skin temperature and measured ambient temperature, the WCD can automatically adjust the thermostat 2420 to alter the ambient temperature of the room. In this regard, if a user's skin temperature is too high, the WCD can instruct the thermostat 2420 to lower the ambient temperature. Similarly, if the user's skin temperature is too cold, the WCD can instruct the thermostat 2420 to raise the temperature. The WCD 2410 can instruct the thermostat (and/or an HVAC controller) directly, e.g., via a direct wireless link 2415, or indirectly, e.g., via one or more of the mobile device 2440 and the access point 2430. The WCD can also use historic temperature data to develop trend temperature data.

In another example, the WCD can be part of a system 2400C for controlling home appliances. The system 2400C can include a WCD 2410C, one or more home appliances 2420C, and an access point 2430C. Such home appliances 2420C can include, for example, a television, lights, speakers, microwave, range, stove, oven, etc. Each of the home appliances can include an antenna that allows the respective home appliances to communicate wirelessly with one or more access points 2430C. In one example, the appliances can include a ScenSor DWIO00 chip provided by Deca-Wave. In this way, the locations of the appliances in the room can be determined to an accuracy of approximately 10 cm. The location of the WCD 2410C can also be determined, using the above-referenced chip, or by using signal strengths of one or more base stations.

Having established the position of one or more home appliances and the user in a room, the user can make a gesture to control such home appliances 2420C. For example, the user can point at the TV (while wearing the WCD) in order to turn it on/off. Knowing the position of the user and the position of the TV, the direction of the gesture and the type of gesture can indicate what action to take on which device. The accelerometer and/or magnetometer on the WCD can be used to create a vector to the object to control, and a wireless packet can bet sent to a wireless access point to control the respective appliance.

FIG. 24D is a flow chart depicting a method 2400D of controlling home appliances according to one or more aspects of the disclosure. At block 2410D, the locations of one or more home appliances in a room and/or house can be ascertained/determined. As described above, the appliances can include a processor configured to identify location within a room. At block 2420D, the location of the WCD is determined. At block 2430D, the user can make a gesture toward a home appliance to exert control over the home appliance. Such gesture can include a snap, a point, etc. At block 2440D, the accelerometer and/or magnetometer on the WCD can be used to create a vector to the object to control. At block 2450D, a wireless packet can bet sent to a wireless access point to control the respective appliance. The access point can then issue the command to the respective appliance.

FIG. 25 is a perspective view of the hand of a user employing a two-factor authentication technique according to one or more aspects of the disclosure.

As shown, the user 2500 is wearing a WCD 2510 and is approaching a locked door 2520 with an access node 2530 associated therewith. The access node 2530 can be a wireless access node of a conventional or custom arrangement, and can communicate wirelessly according to any type of wireless protocol, such as WiFi or Bluetooth. As the user approaches the door 2520, the WCD 2510 can initiate a communication link, e.g., Bluetooth or WiFi, with the access node 2530. In this way, the WCD and the access node can engage in one or more handshaking or query procedures to verify the WCD. For example, the access node 2530 can detect a MAC address, IP address, or other alphanumeric identifier associated with the WCD and compare it to a list of authorized users. Such network-based communication processes should also be clear to those of skill.

Once the MAC address or other identifier is verified, the user can engage in a pre-defined gesture 2550 to complete the authentication procedure. The gesture 2550 can be any type of hand and/or finger motion that can be performed by the user. In this regard, the accelerometer or magnetometer can detect the gesture 2550 performed by the user and provide the gesture information to the access node. If the provided gesture information corresponds with an authorized gesture stored at or accessible by the access node, then the user may be granted authorization and the door can be unlocked. The authorized gesture can be a general authorized gesture for all users, or can be a specific gesture authorized only for the particular MAC address.

In addition to a door, the method above can be used to gain access to other features, such as unlocking a mobile phone, unlocking a car door, starting a car. The authentication technique above is advantageous in that it can eliminate extraneous authentication devices, such as key fobs for a car, a door, keypads for entry control, etc., and can provide a secure two-factor authentication technique to avoid unwanted access. More generally any type of keyless entry system (e.g. a keypad, card-reader, keyless lock, etc.) can be equipped with appropriate communication interfaces (RF, IR, etc.) to communicate with the WCD and operate based on a gesture and/or proximity of the user using the techniques described above. The WCD can also be employed generally in this manner to activate or deactivate a residential or commercial alarm system-substituting, for example, for a key fob used for this purpose.

Figure 26A:
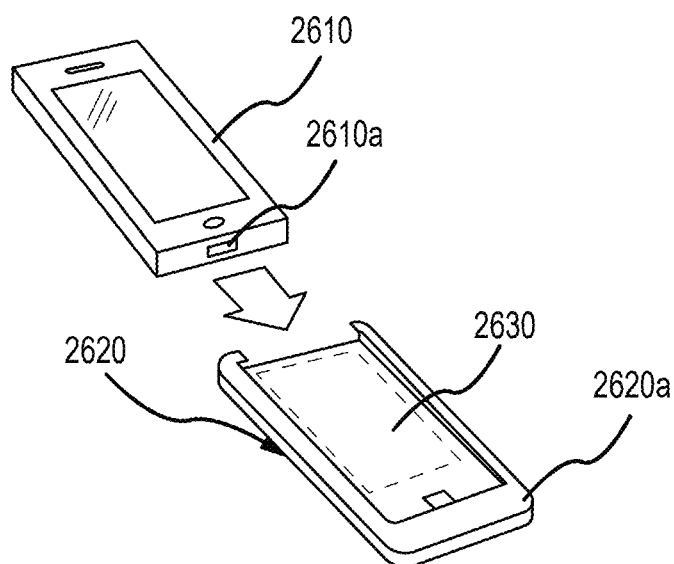
FIG. 26A is a schematic view of a charging apparatus for charging the WCD according to one or more aspects of the disclosure.

FIG. 26A is a schematic view of a charging apparatus for charging the WCD according to one or more aspects of the disclosure. As shown, a mobile device 2610 can be received within a case 2620. The mobile device 2610 can be electrically connected to the case 2620 via a port 2610a on the mobile device 2610 and a connector 2620a on the case 2620. As shown in phantom, the case 2620 can include an integrated battery 2630 within the case that can charge the mobile device via the connector or can charge a WCD, as will be described in greater detail below.

Figure 26B:
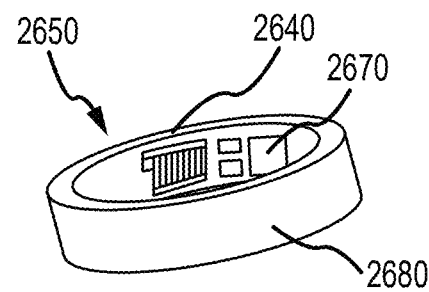
FIG. 26B shows a WCD including an RF antenna and charging circuitry.
Figure 26C:
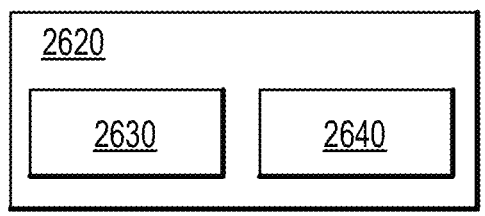
FIG. 26C is a block diagram of the charging apparatus according to one aspect of the disclosure.

The integrated battery can be connected to an antenna 2640 disposed on or within the case 2620 that can emit an RF signal, as shown in the block diagram in FIG. 26C. The RF signal can have a power of less than 500 mW and a frequency of 13.56 MHz. The RF signal can be emitted in all directions around the case such that it can be received by a WCD in proximity to the case.

Figure 26D:
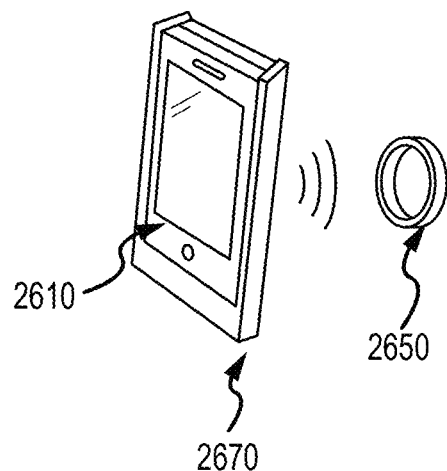
FIG. 26D is a pictorial diagram showing of the WCD according to one or more aspects of the disclosure.

FIG. 26B shows a WCD 2650 including an RF antenna 2660 and charging circuitry 2670. The RF antenna 2640 can be disposed within the housing 2680 and can receive the RF signal emitted by the case 2620 and convert it to a current that can be used to charge the WCD battery (not shown). This can advantageously allow the user to charge the WCD without removing the WCD from the finger. As shown in FIG. 26D, the charging can occur whenever the WCD is in close proximity to the case, such as when a user talking on the phone or merely handling the phone. In another implementation, the case can utilize inductive charging to charge the WCD. In this regard, the case can include an induction coil subjected to a predetermined current to produce a magnetic field. A corresponding induction coil within the housing of the WCD can be subjected to the magnetic field to produce a current that can charge the onboard battery in accordance with known electromagnetic principles.

Figure 27A:
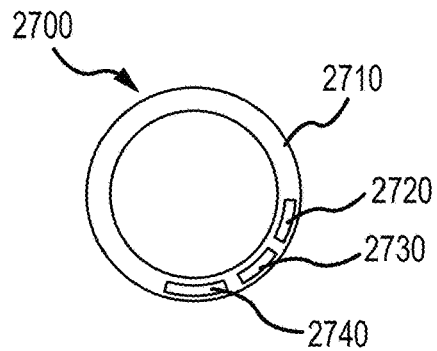
FIG. 27A is a pictorial diagram and FIG. 27B is a block diagram of a WCD employing flash storage according to one or more aspects of the disclosure.
Figure 27B:
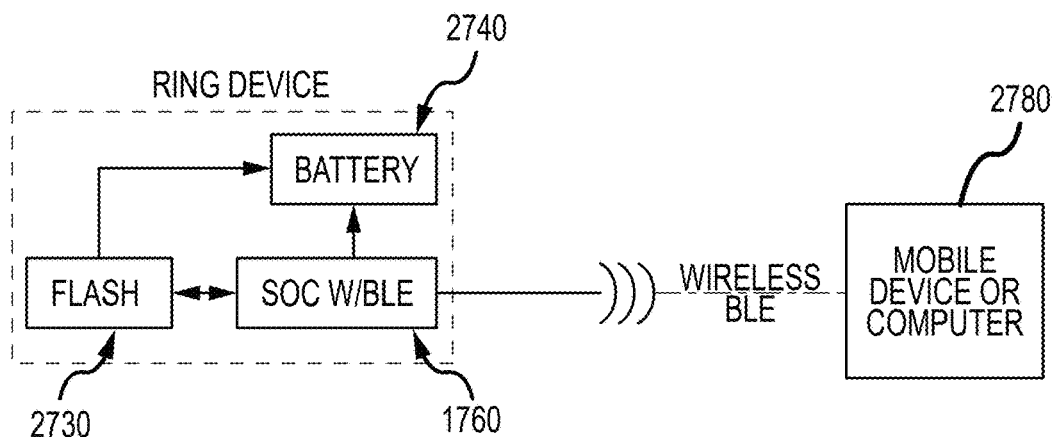

FIG. 27A is a pictorial diagram and FIG. 27B is a block diagram of a WCD employing flash storage according to one or more aspects of the disclosure. As described above, the WCD 2700 can include a housing 2710, an antenna 2720, and an integrated circuit (IC) 2730 including a flash memory 2740. The IC and the flash memory can be disposed within the housing 2710. The flash memory 2740 can be powered by a battery 2750 and connected to the IC 2730, which can be implemented as a system-on-a-chip (SoC) IC 2760. The IC can include Bluetooth Low Energy (BLE) capability to allow for communication with another device. The flash memory can be used to store data, or can be used in any of the authentication techniques described above. The WCD can transmit data stored on the flash memory to another device 2780 via the BLE connection, or can receive data and store the data on the flash memory.

Figure 28A:
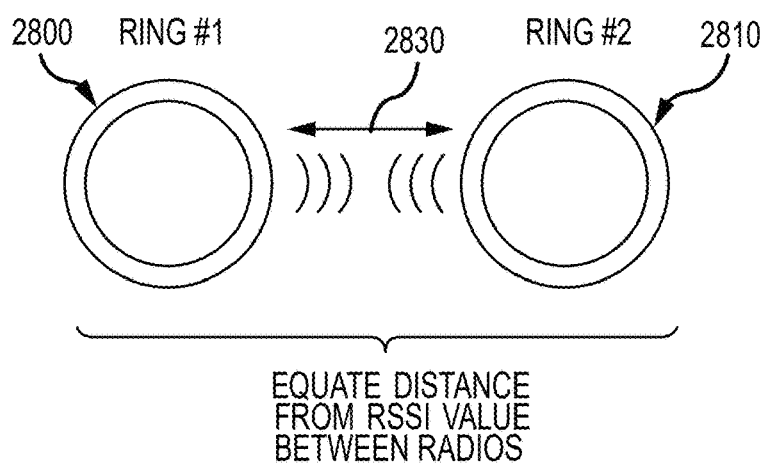
FIG. 28A is a schematic diagram of one or more WCDs performing proximity functions according to one or more aspects of the disclosure.

FIG. 28A is a schematic diagram of one or more WCDs performing proximity functions according to one or more aspects of the disclosure. The WCD can detect a strength of an RF signal received by its antenna, and calculate a distance to the source of the RF signal using a Received Signal Strength Indicator (RSSI). In one example, the RF signal can be from a mobile device, an access point, or another WCD. The use of RSSI can have many applications in proximity detection. For example, the WCD can be placed on a child and can be connected to mobile device held by a parent. If the WCD travels a predetermined distance from the mobile device, the WCD can issue an alert to the mobile device, thereby alerting the parent that the child has wandered too far. In another example, the parent can wear a first WCD and the child can wear a second WCD. The first WCD can alert the parent that a child has wandered too far.

A single user can wear a first WCD 2800 on a first finger on a first hand and a second WCD 2810 on a second finger on a second hand. In this regard, the user can measure the relative distance between the first and second fingers using an RSSI via a wireless link 2830 between the WCDs 2800, 2810, such as a BLE connection. This can be used to measure an approximate dimension of an object held in both hands or to estimate a mid-air measurement.

In some examples, a first user can wear a first WCD 2800 and a second user can wear a second WCD 2810. The RSSI can be collected over a period of time and the processor can analyze the data to develop trends or statistics. For example, the RSSI data can indicate that the first and second users have spent a certain amount of time together and can serve as a relationship monitor.

Figure 28B:
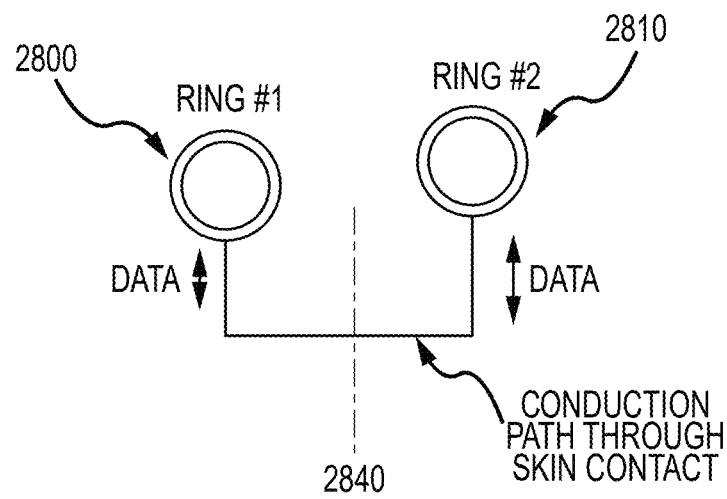
FIG. 28B is a schematic diagram of one or more WCDs performing proximity functions according to one or more aspects of the disclosure.

The WCD can also detect when the first user and second user are holding hands. FIG. 28B is a schematic diagram of one or more WCDs 2800, 2810 performing proximity functions according to one or more aspects of the disclosure. Similar to the ECG monitoring techniques described above, a circuit can be formed when the users hold hands 2840 (with the respective hands wearing the WCDs). The circuit can be used to transmit data and/or electrical impulses between the respective WCDs via the circuit. The WCDs can collect data regarding the length of time that the users are holding hands and, in combination with the amount of time spent together, monitor the relationship of the two users. In addition, the WCD can collect data regarding communication between the users, e.g., e-mail, social media, etc. Based on all of the above factors, the WCD can develop a relationship score between respective WCD users, with a higher relationship score indicating more and more frequent interactions.

Figure 29A:
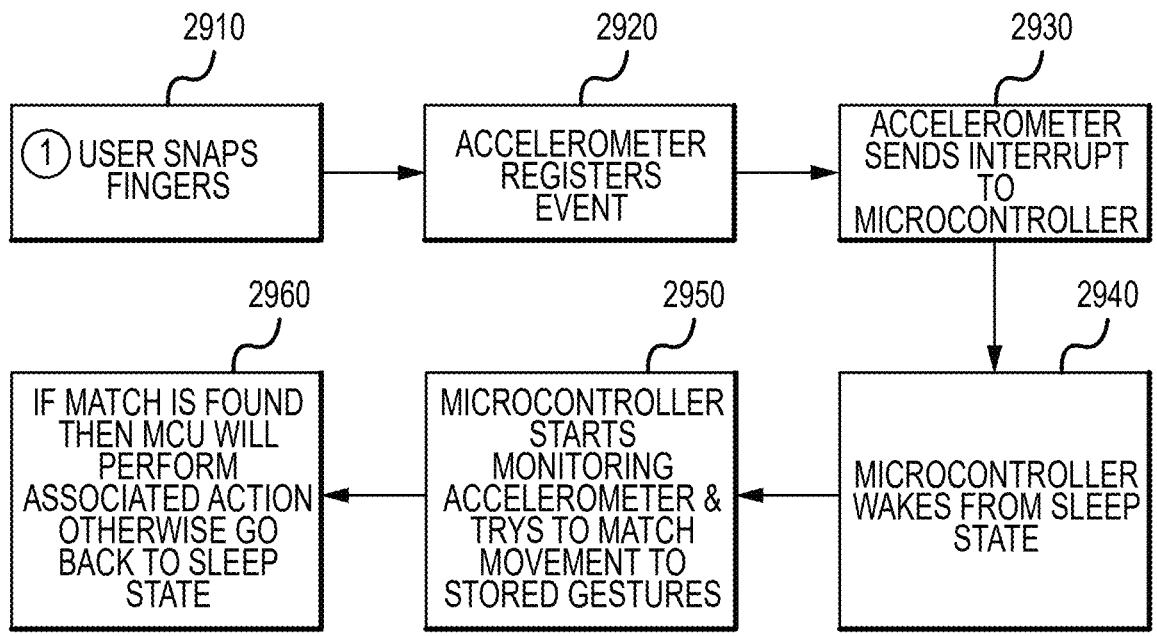
FIG. 29A is a flow chart depicting a method of initiating gesture input according to one or more aspects of the disclosure.

FIG. 29A is a flow chart depicting a method of initiating gesture input according to one or more aspects of the disclosure. The WCD can be used to perform one or more commands, or to instruct another device, such as a mobile device, to perform one or more commands. Such commands can include, initiate sleep state of WCD, initiate sleep mode or default mode of WCD, powering off/on of the WCD, turning on/off an LED light of the WCD, powering on/off of a mobile device, placing a phone call on the mobile device, etc. The user can establish one or more custom gestures to initiate any of the commands above. For example, the user can select a command to be customized from a number of commands. Once selected, the user can perform a custom gesture to be associated with that command. In some examples, the user can perform the custom gesture multiple times to allow the WCD to better identify the gesture and to develop error tolerances for registering the gesture.

At block 2910, the user can perform a first gesture. In this example, the user can perform a finger snap. At block 2920, WCD can register the gesture, via the accelerometer and/or the magnetometer. At block 2930, the accelerometer can send an interrupt signal to the processor. At block 2940, the processor can wake from a sleep or default system state. At block 2950, the processor can monitor the accelerometer for a second gesture, at which point the user can perform a second gesture. If the second gesture matches a gesture in the gesture command database, then the WCD can perform the associated command. If not, the WCD can return to the sleep state.

Figure 29B:
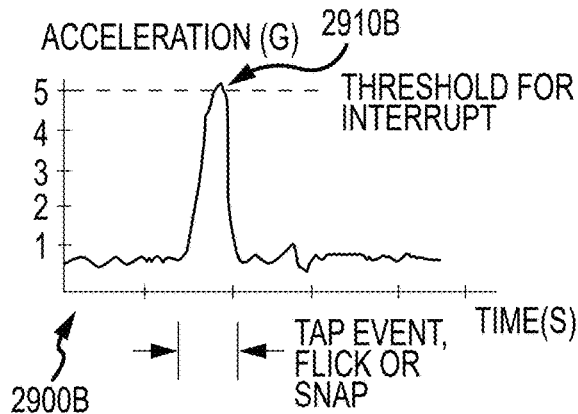
FIG. 29B is a chart showing acceleration vs. time as measured by the accelerometer of the WCD.

FIG. 29B is a chart 2900B showing an exemplary graph of acceleration vs. time as measured by the accelerometer of the WCD. As shown at peak 2910B, the gesture can only be registered if it reaches a predetermined acceleration threshold. If the gesture performed at 2910 meets the threshold, it can proceed to block 2930 where the interrupt procedure is performed.

Figure 30:
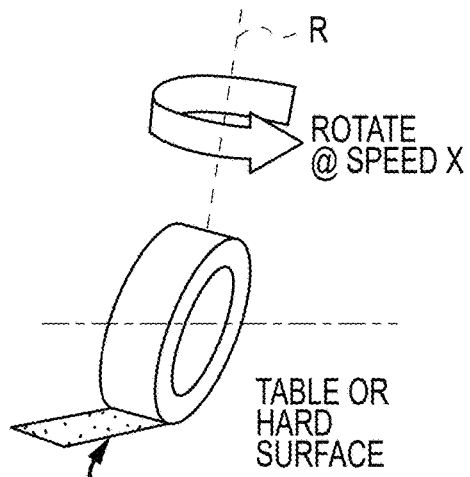
FIG. 30 is a perspective view of a WCD 2000 employing a reset function.

FIG. 30 is a perspective view of a WCD 3000 employing an illustrative reset function and associated procedure/process. As shown, the WCD 3000 can be removed from the finger of the user in order to initiate a system reset of the WCD. In one example, the system reset can be initiated by spinning about a rotation axis R at a predetermined speed. The predetermined speed can be any value, and in one example is a rotational velocity. Upon performing the reset procedure at the predetermined speed, operation of the WCD 3000 can be interrupted and the onboard components of the 3000 can power off, and revert to factory default settings. Additionally, a series of movements can initiate a rest, such as putting the ring on a table and turning it over several times.

Figure 31A:
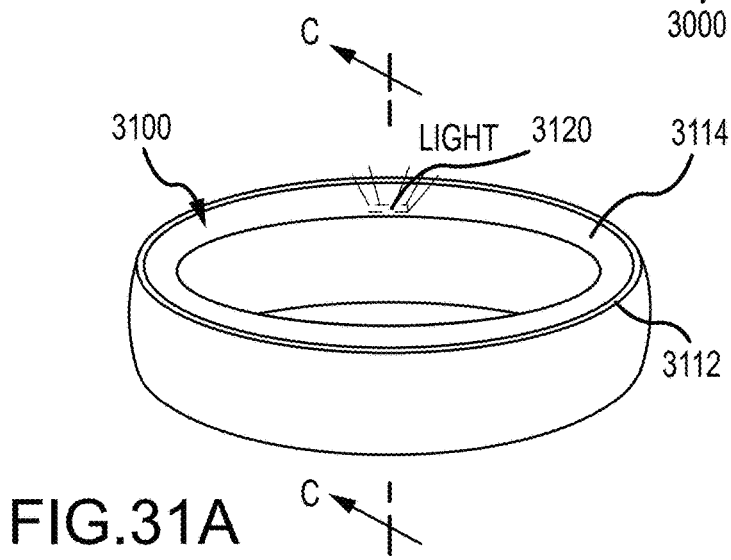
FIG. 31A is a perspective view of a WCD including an LED indicator according to one or more aspects of the disclosure.

FIG. 31A is a perspective view of a WCD including an LED indicator according to one or more aspects of the disclosure. As shown, the WCD 3100 can include an internal/external housing 3112 and an internal/external potting 3114. The WCD can include an LED 3120 that can be visible through the internal/external potting 3114.

Figures 31B, 31C:
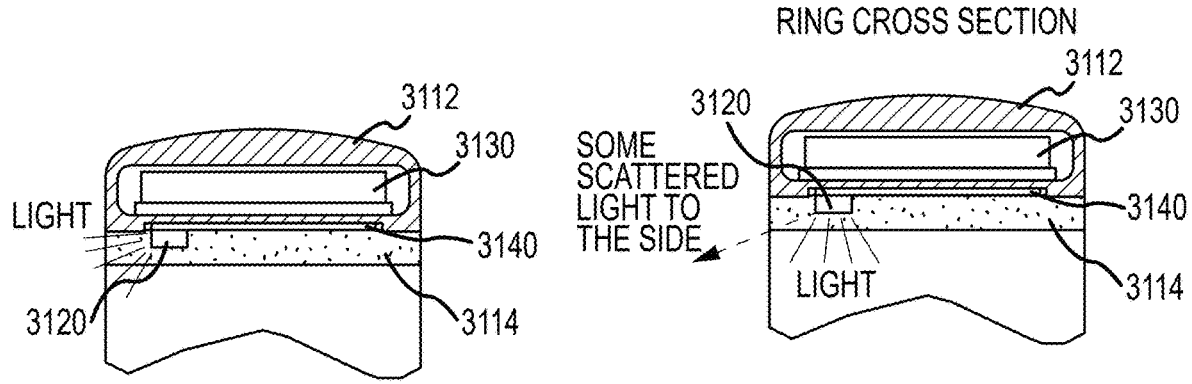
FIGS. 31B and 31C are cross sections along line C-C of a WCD employing an LED indicator according to one or more aspects of the disclosure.

FIGS. 31B and 31C are cross sections along line C-C of a WCD employing an LED indicator according to one or more aspects of the disclosure. As described above, the WCD 3100 can have an internal and/or external potting 3114 that can be transparent. This allows light sources within the housing to pass through the potting without changing, or with minimal change to, the optical properties of the light. In this way, a light source 3120, such as an LED, can be disposed on the PCB 3140 and can be powered at least partially by battery 3130. The LED can be encapsulated by the potting 3112 and can project light through the potting 3112. As shown in FIG. 31B, the LED 3120 can include a vertical LED, while 31C depicts a right angle LED. The vertical LED can project light along direction L1, while the right angle LED can project light along direction L2. When light is projected along L2, the light can travel around a circumference of the finger of the user. Note that, according to aspects of the disclosure, the potting can be generally adapted in whole or in part to condition, filter or modify the wavelengths and/or projection qualities of light by for example, embedding lensmatic components, applying light-diffusive additives, light attenuating filter materials, etc.

Figure 32:
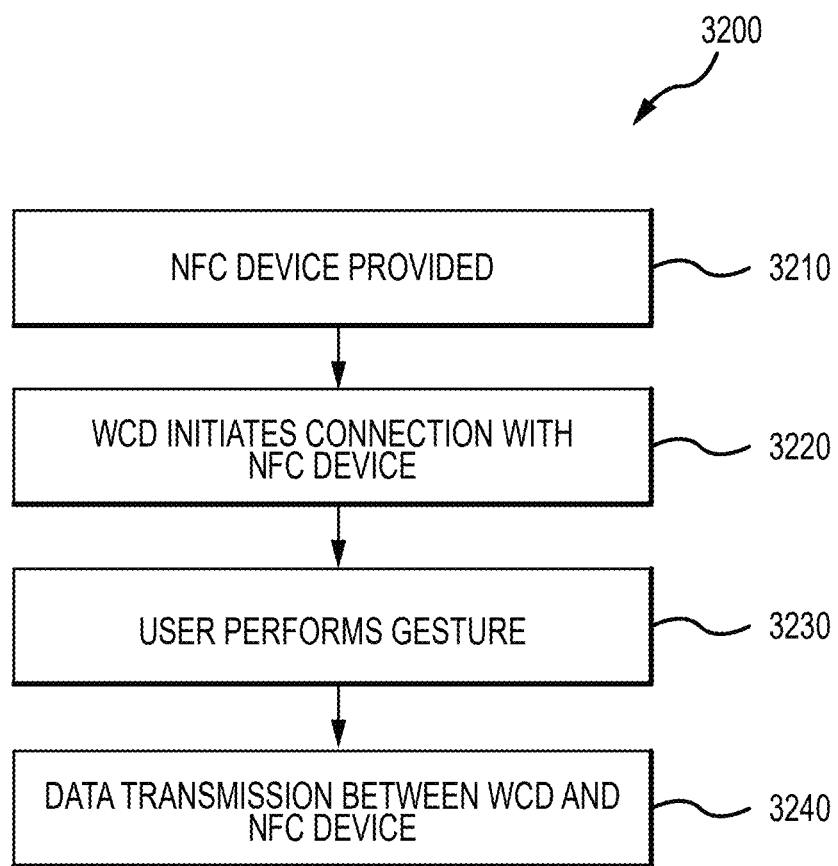
FIG. 32 is flow chart depicting a method of communicating with a near field communication (NFC) device according to one or more aspects of the disclosure.

FIG. 32 is flow chart depicting a method 3200 of communicating with a near field communication (NFC) device according to one or more aspects of the disclosure.

In some examples, the WCD can enable or disable NFC or change the functionality of a NFC device. For example, the WCD can itself engage in NFC with another computing device, or the WCD can be connected via wireless link to a computing device that engages in NFC with a different computing device. In certain existing NFC devices, NFC will connect and begin transmitting data as soon as it is queried. In the present example, NFC is enabled or begin transmitting data exclusively upon performing of a predetermined gesture. However, a variety of other transmission processes can be implemented—for example a periodic chirp or handshake request by the WCD for communication with appropriate devices.

At block 3210, a NFC capable device is provided. The device can be any type of device, such as a laptop, tablet, mobile device, or dedicated NFC device.

At block 3220, the WCD initiates a connection with the NFC device. The connection can be a direct connection via NFC, or an indirection connection via an intermediate device. At this point, no data has yet been transmitted between the WCD and the NFC device.

At block 3230, a user performs a predetermined gesture that is registered by the WCD. The gesture can be any type of gesture, such as a point, a snap, waving the hand, etc.

At block 3240, data transmission begins between the NFC device and the WCD.

In other examples, the user can perform another gesture to cease NFC communication. The gesture can be the same gesture as described above or a different gesture. Additionally, the user can remove the ring to disable the NFC. Upon donning the ring the user will be prompted by the application on the mobile device to re-authenticate by entering a PIN, whereby the proper PIN results in re-enabling the NFC functionality.

In yet another example, the WCD device employing NFC can be configured on the fly to map to different data sets stored thereon. For example, the WCD device employing NFC can employ data thereon to make purchases, e.g., account information, data to access a building, e.g., a key fob, and data thereon to board public transportation, e.g., smart card, metro card, etc. A user can perform a predetermined different gesture for each of the above data sets to access the data. Once accessed, the WCD device employing NFC can initiate a link with another computing device to initiate a transaction, to open a door, or to board public transportation, etc.

VI. OPTICAL ELEMENT AND ATTACHMENT FRAME

Figure 33A:
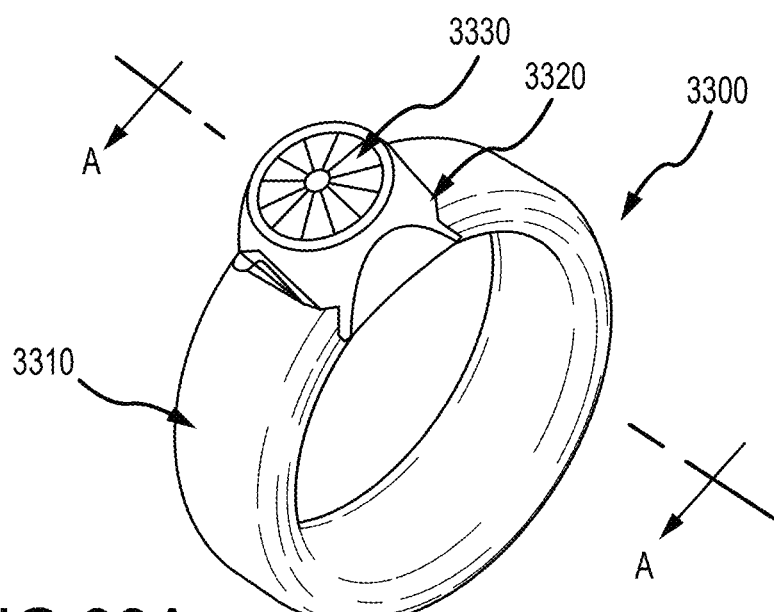
FIG. 33A depicts a perspective view of a WCD assembly according to one or more aspects of the disclosure.
Figure 33B:
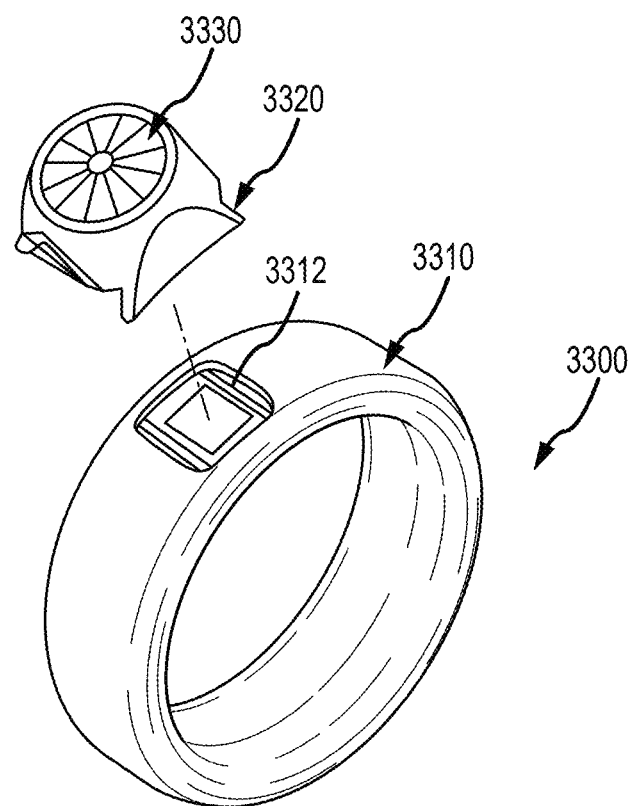
FIGS. 33B-D depict exploded views of the WCD assembly of FIG. 33A.
Figure 33C:
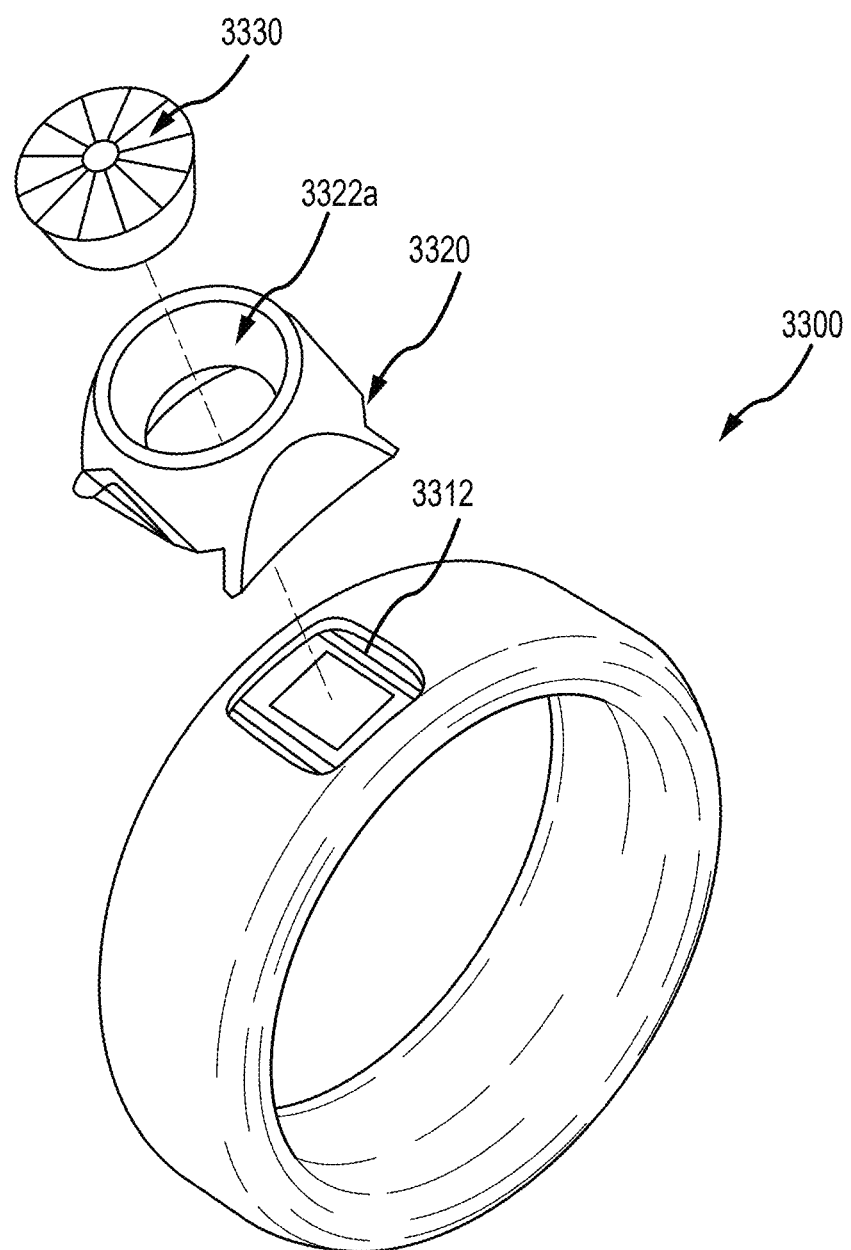
Figure 33D:
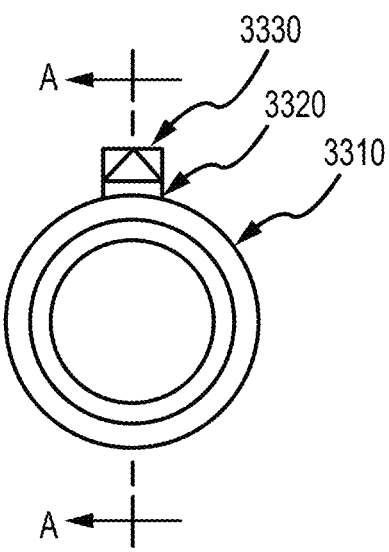

FIG. 33A depicts a perspective view of a WCD assembly 3300 according to one or more aspects of the disclosure, while FIGS. 33B-D depict exploded views of the WCD assembly and 33E depicts a cross sectional view of the WCD assembly along A-A. In this example, the WCD assembly 3300 includes a WCD 3310, an attachment frame 3320, and an optical element 3330. The WCD 3310 can be any of the WCD examples described above or below in the present application.

The attachment frame 3320 is releasably attached to the WCD 3310. The optical element 3330 is itself releasably attachable to the attachment frame 3320. In this regard, the attachment frame 3320 provides an attachment interface between the WCD 3310 and the optical element 3330, thereby allowing the optical element 3330 to be at a fixed position in space with respect to the WCD 3310 or any portion thereof. The attachment frame 3320 can be made of any material, such as a metal, polymer, etc. Any type of polymer can be used, such as thermosetting plastics, thermoplastics, PETE, polycarbonate, polyethylene, LDPE, or any other type of plastic.

The attachment frame can be sized and shaped to fit along the curved surface of the WCD. For example, the attachment frame can have a curved undersurface to allow a flush fit with the curved surface of the WCD. The attachment frame can have any shape, size, or radius of curvature depending on the size and shape of the WCD.

Figure 33E:
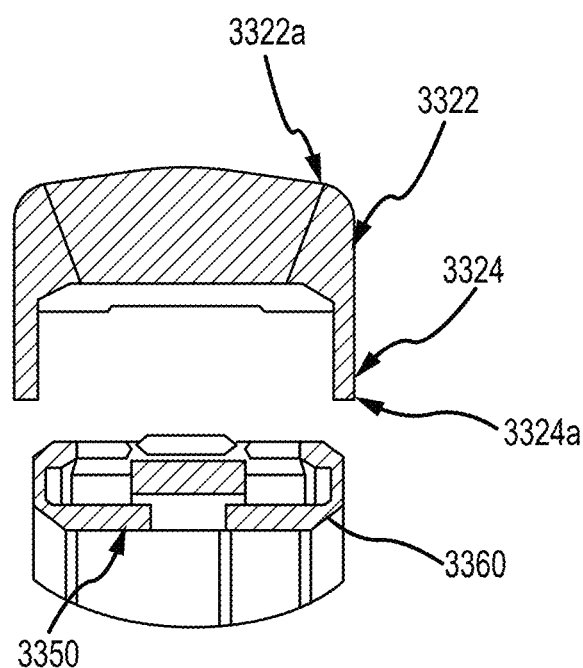
FIG. 33E depicts a cross sectional view of the WCD assembly along A-A.

The attachment frame 3320 includes a first retaining a portion 3322 and a pair of second retaining portions 3324. The first retaining portion 3322 defines a conical recess 3322a configured to receive the optical element 3330, and provides a generally unoccluded pathway for light to pass through the optical element and onto the WCD. Although depicted as defining a conical or frustoconical shape, the recess 3322a can be any other shape depending on the shape of the optical element 3330. Each of the second retaining portions 3324 includes a respective locking feature 3324a. The respective locking features 3324 and a extend from the second it retaining portion 3324 toward one another such that a distance between the respective locking features is greater than a distance between the remaining portions of the second retaining portions. As shown in FIG. 33E, the locking features engage with an inward-facing surface 3350 of the WCD to ensure a secure fit. In one example, the inward-facing surface of the WCD may itself have one or more features 3360 to engage with the locking features of the second retaining portions. Such one or more WCD features can include projected surfaces, recesses, or any other type a feature to allow for engagement with the attachment frame.

The optical element 3330 can be made of any material capable of modifying, e.g., focusing, incident electromagnetic radiation, such as visible light, ultraviolet light, infrared light, or any other type of electromagnetic radiation. In some examples, the optical element 3330 can be constructed from a polymer, such as any of the polymers identified above. In another example, the optical element can be made of glass, quartz, diamond, zirconium, or any other material capable of focusing light. More generally, the optical element 3330 is formed with a general outward appearance simulative of a faceted jewel with an appropriate tint or coloration (including clear/white). The term "jewel" can also be used in the alternative to describe the optical element 3330 herein.

The WCD can include CPV cell 3312 that can be disposed directly underneath the attachment frame 3320 and optical element 3330 when assembled. In other examples, the CPV can be positioned within the housing and can receive electromagnetic radiation via a transparent potting material. In this regard, incident light striking the optical element 3330 can be focused on to the CPV cell to allow for charging of the internal battery of the WCD. The optical element 3330 provides an increased charging efficiency when compared to the CPV exclusively receiving ambient light, since the ambient light is collected/gathered from a wider field, and then focused onto the CPV by the optical element 3330. In one example, a focal length of the optical element 3330 is different than a distance between the optical element and the CPV. For example, the focal length can be greater than or less than the distance between the optical element and the CPV. This can be advantageous in various aspects of the disclosure so as to avoid the light from focusing at a focal point directly on the CPV, which could cause damage to the CPV itself by over-concentrating the light at that single point of the overall CPV surface.

Figure 34A:
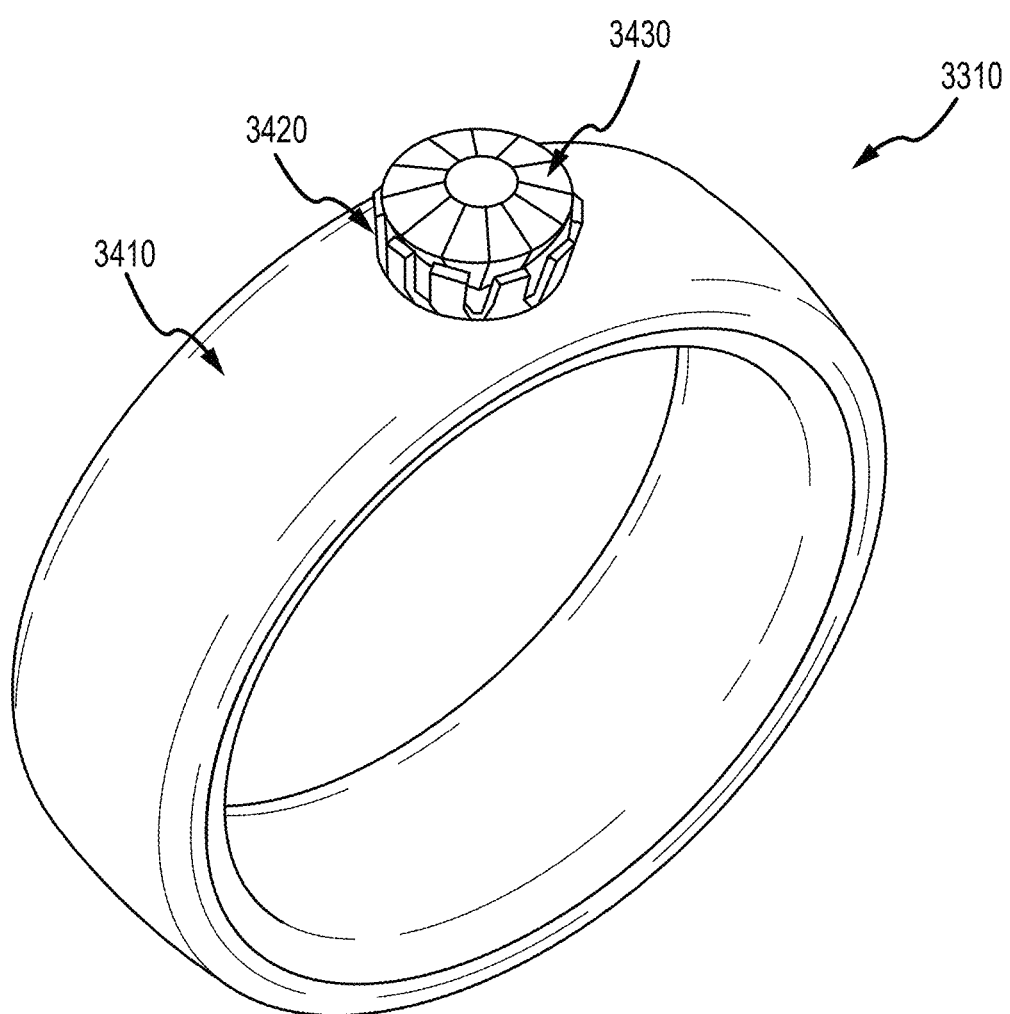
FIGS. 34A-B depict a WCD assembly according to one or more aspects of the disclosure.
Figure 34B:
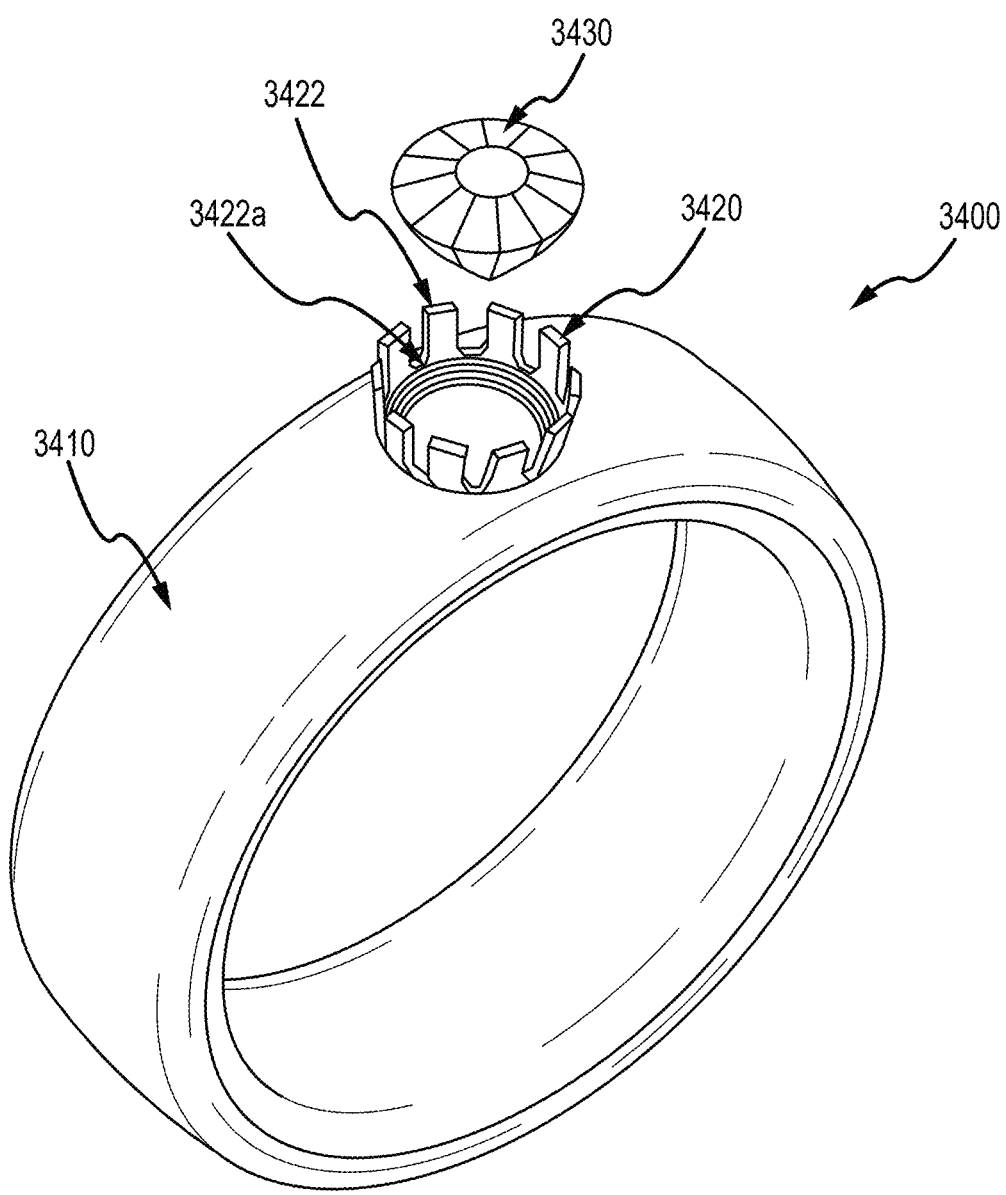

FIGS. 34A-B depict a WCD assembly 3400 according to one or more aspects of the disclosure. In this example, the attachment frame 3420 does not extend to an inward-facing surface of the WCD 3410, but is instead form entirely on the outside-facing surface of the WCD. In some examples, the attachment frame 3420 can be semi-permanently or permanently affixed to the outward-facing surface of the WCD and can have a plurality of retaining portions (mounting prongs) 3422 that at least partially define a recess 3422a for receiving the optical element. As shown in FIG. 34B, the optical element 3430 is releasably attached to the attachment frame 3420. This configuration can be particularly desirable, as it exhibits ornamental similarities to a traditional engagement ring while still having the increased functionality of the WCD. Note that while not shown, the mounting prongs can include small hook ends that springably retain the optical element 3430 when attached, but that can release the optical element based upon a prying motion. A customized grasping tool (not shown) can also be employed to remove (and attach) the optical element in this example.

VII. ENCLOSURE/PACKAGING

Figure 35A:
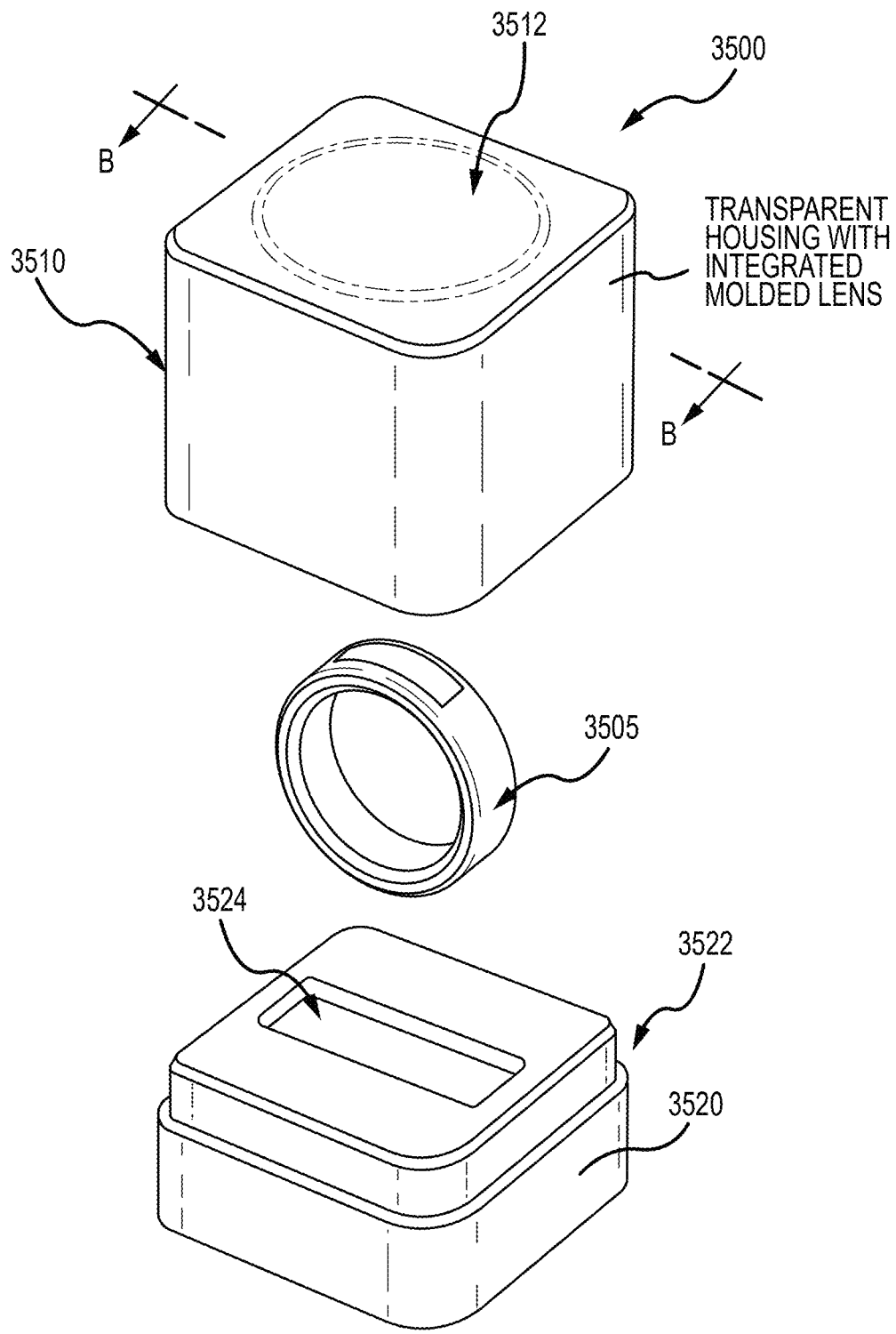
FIG. 35A depicts an enclosure or case for storing a WCD according to one or more aspects of the disclosure.

FIG. 35A depicts an enclosure or case 3500 for storing a WCD according to one or more aspects of the disclosure. As shown, the enclosure 3500 includes a lid 3510 and a base 3520. The lid 3510 and base 3520 can engage via a recessed portion 3522 formed in the base 3520 to provide a substantially sealed interior environment.

The lid 3510 can be cuboidal in external dimensions, or define any other type of geometric shape that allows sufficient internal volume to contain the WCD. For example a custom design shape (polyhedral, etc.) can be employed. In this example, the top portion 3510 is substantially cuboidal as shown, including rounded edges rather than vertices. The lid can be substantially transparent to allow viewing of the WCD while enclosed therein, and can be made of any type of material, such as a polymer, glass, etc. The lid can also be mounted with pins on a hinge.

The base 3520 can be cuboidal, or any other type of geometric shape. In this example, the bottom portion is substantially cuboidal, including rounded edges rather than vertices as shown. The bottom portion can be made of any material and can be transparent or opaque.

The base 3520 can define a receptacle 3524 for receiving the WCD 3505. The receptacle 3524 can be sized and shaped to receive the WCD 3505 and in this example is semicylindrical, e.g., a portion of a cylinder. The radius of the semicylinder can be slightly larger than a radius of the WCD in order to accommodate the WCD securely. The receptacle can lined with a soft material to allow for a soft, safe material to receive the WCD, such as a silicone, thermoplastic, fabric, felt, or other material.

Figure 35B:
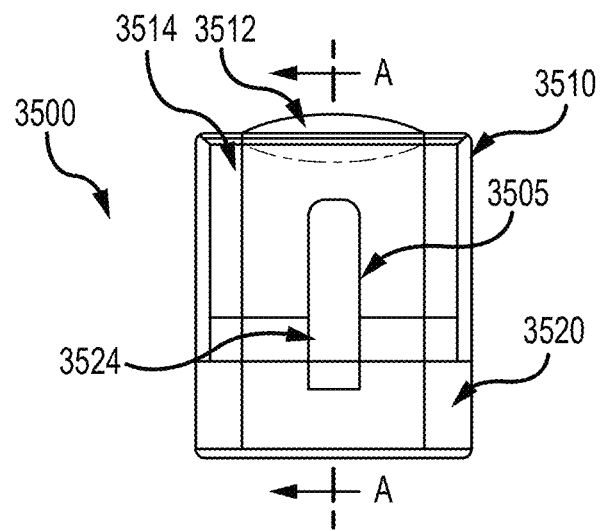
FIG. 35B is a cross sectional view of the assembled enclosure of FIG. 35A along the line B-B.

FIG. 35B is a cross sectional view of the assembled enclosure 3500 shown above along the line B-B. As shown, when assembled, the WCD 3505 fits securely within the receptacle 3524. The interior of the lid 3510 can be sized and shaped to conform to the shape of the WCD such that the WCD is completely surrounded and enclosed by the lid 3510, while in other examples, the lid 3510 can be sized and shaped to allow for airspace 3514 between the lid surface and the WCD.

Figure 35C:
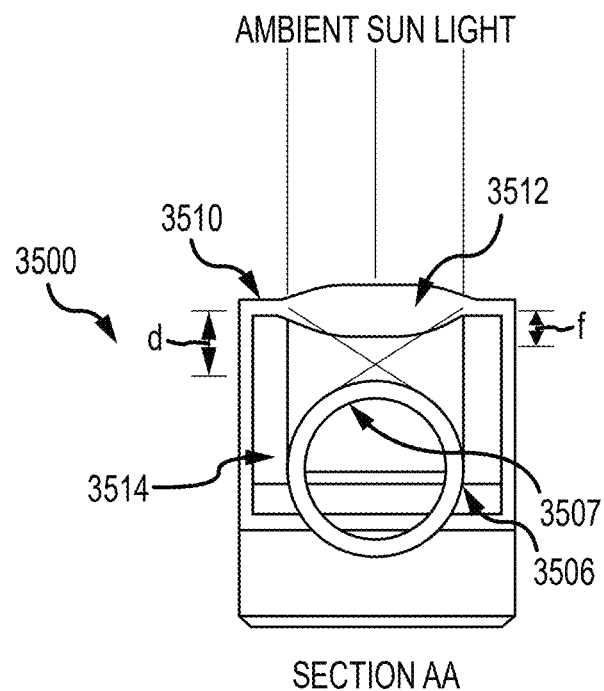
FIG. 35C depicts a cross sectional view of the assembled enclosure of FIG. 35B along line A-A.

FIG. 35C is a cross section of the enclosure along line A-A. As shown, the lid 3510 can include an integral optical element 3512. The optical element 3512 can be a lens or any other device to modify, e.g. focus, light that passes therethrough. In this example, the optical element 3512 can be disposed at a predetermined distance away from one or more CPV cells 3507 disposed on the WCD 3505. This distance d can be measured from the center of the optical element to the CPV cells 3507, and the optical element can itself have a focal length f. In one example, the distance d can be greater than the focal length f, such that the optical element focuses light at a point above the WCD in the enclosure. In this regard, the light will not focus directly on the CPV cells disposed at the surface of the WCD, thereby avoiding overheating or damage to the CPV cells. In other examples, the distance d can be less than the focal length, which can also prevent light from focusing at a surface of the WCD.

Figure 36:
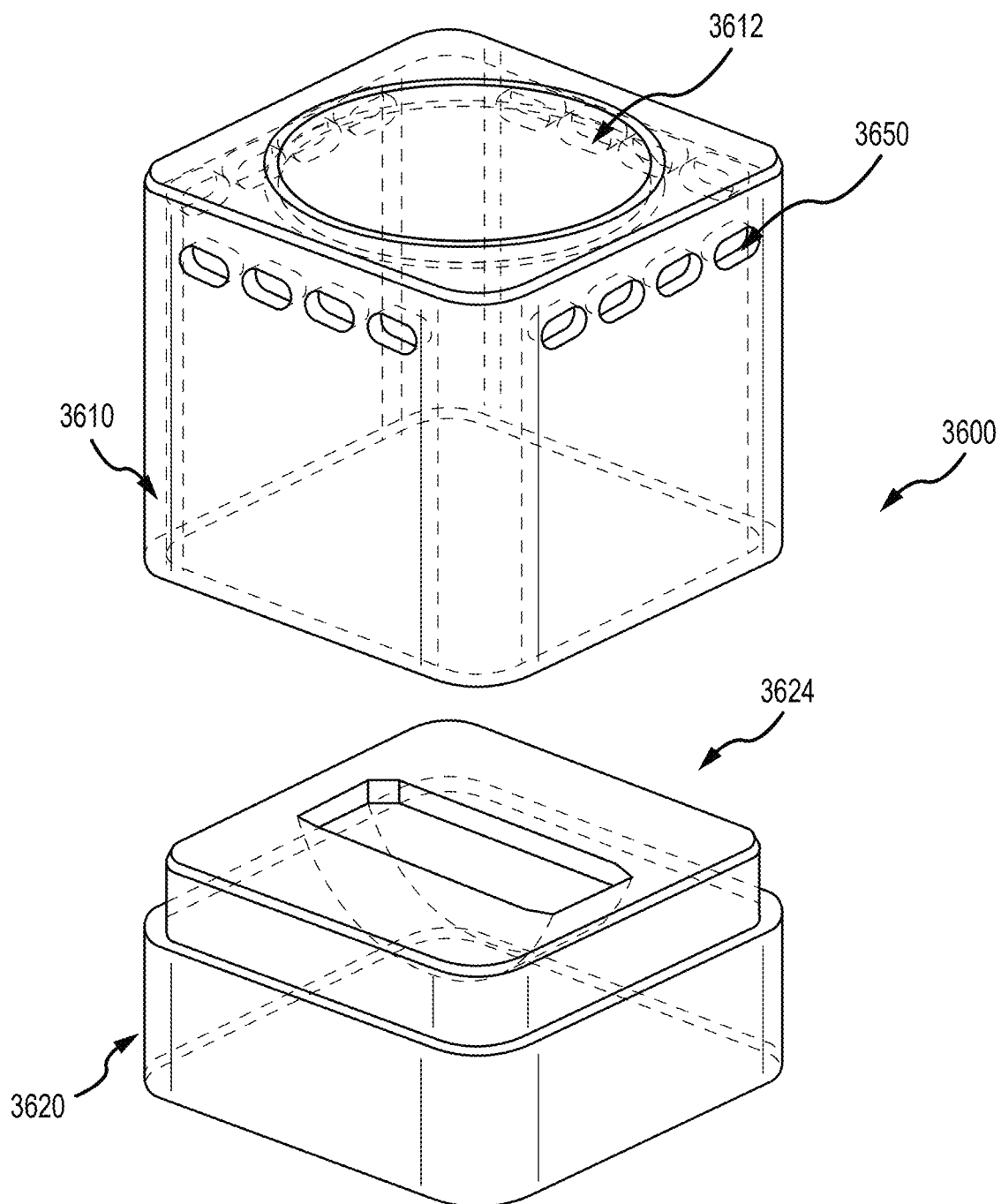
FIG. 36 depicts an enclosure including air vents according to one or more aspects of the disclosure.

FIG. 36 depicts an enclosure 3600 including air vents 3650 according to one or more aspects of the disclosure. In this example, the enclosure 3600 includes a plurality of vent holes 3650. The vent holes can be arranged on one or more faces of the lid. The vent holes 3650 can prevent overheating within the enclosure during charging of the WCD by allowing for circulation of convective air current. During shipping, the vent holes 3650 can be covered by an adhesive and/or adhering (peel-off) polymer sheet of conventional arrangement to prevent debris or moisture from entering the enclosure. The enclosure can include a lid 3610, base 3620, receptacle 3624, and optical element 3612 as in the examples set forth above.

VIII. SIZING

Figure 37:
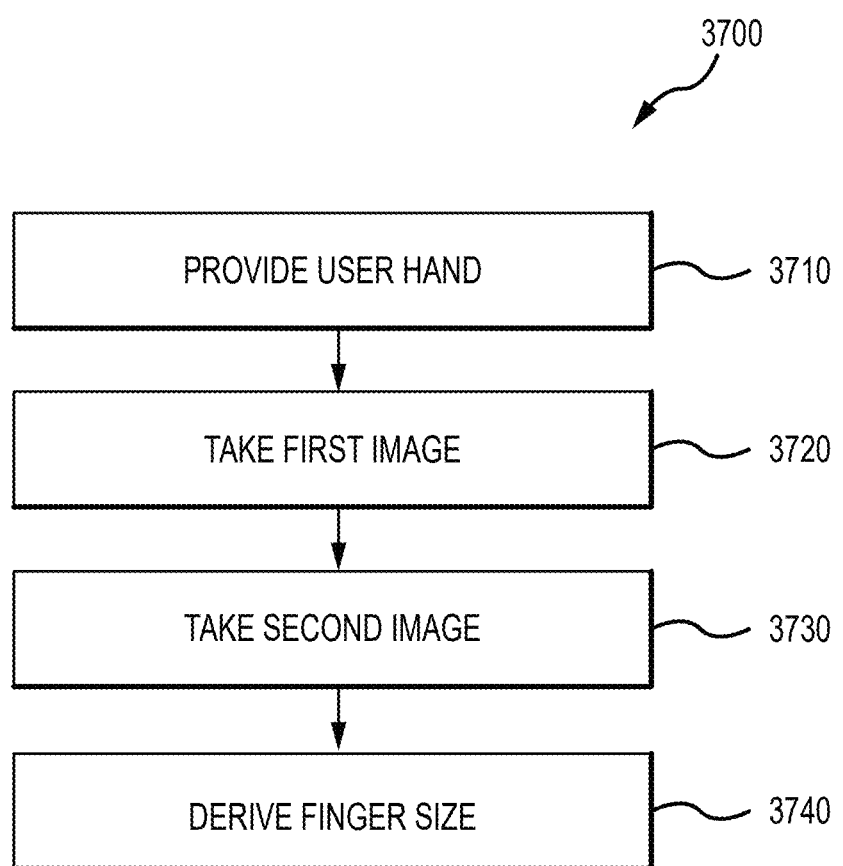
FIG. 37 depicts a method of sizing a finger according to one or more aspects of the disclosure.

FIG. 37 depicts a method 3700 of sizing a finger according to one or more aspects of the disclosure. At block 3710, the hand of a user can be provided. The hand can be held still in mid-air or alternatively can be resting on a surface.

At block 3720, a first image is taken of the user's hand from a first perspective. The image can be taken by any type of imaging apparatus, such as a CCD or CMOS camera, a digital camera, a camera associated with a mobile phone, etc. The first image can be stored in a memory.

At block 3730, a second image is taken of the user's hand at a second perspective. In this regard, the second perspective is different from the first perspective so as to provide a distinct view in the second image of the user's hand. Block 3730 can be repeated any number of times. For example, a third image can be taken of the user's hand at a third perspective. In this regard, the third perspective is different from both the first and second perspectives so as to provide a distinct view in the third image of the user's hand, and so on.

At block 3740, a size of the user's finger can be derived from the plurality of images taken above. In some examples, as few as two images may be required, while in other scenarios, more than three images may be required, depending on a number of circumstances including image quality, selected perspectives, etc. The size can be derived from the plurality of images by any number of techniques, such as stitching the plurality of images together to generate a 3D typography of the fingers, then using photogrammetry algorithms to identify features on the fingers to determine the appropriate ring size. Furthermore, the touch screen of the smart phone can be used to measure the hardness of tissue by measuring the footprint/impression the fingers make while pressing a finger against the touch screen of a mobile phone.

FIG. 38 is a pictorial diagram showing a plurality of image perspectives of a user's hand 3802. As shown, perspectives 3810, 3820, and 3830, as well as the other perspectives, produce corresponding images (in a strip) 3812, 3822, and 3832. The images can be used to derive a size of the user's finger according to the methods described above.

Figure 39:
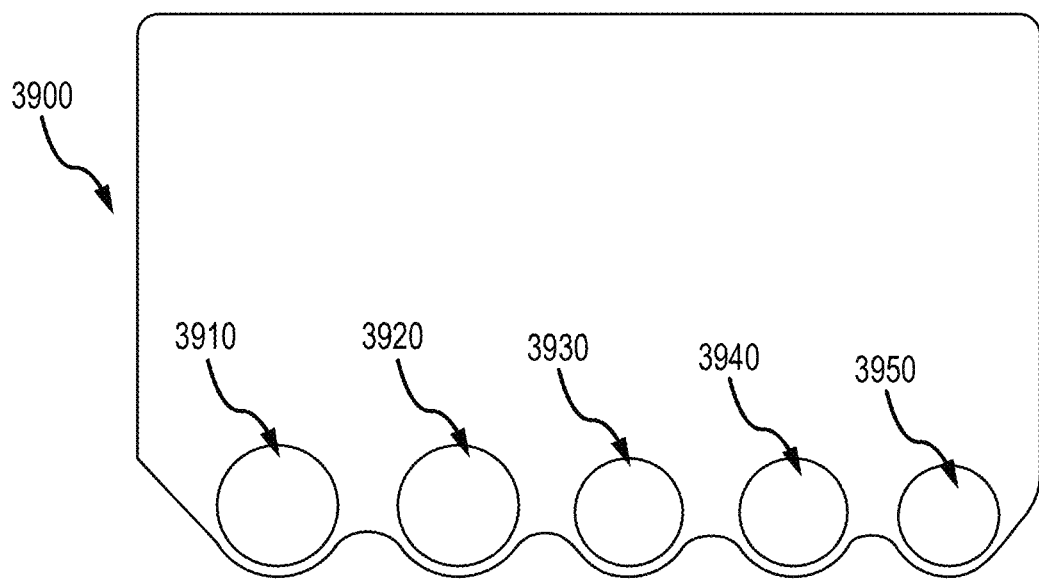
FIG. 39 depicts a sizing tool for sizing the finger of a user.

FIG. 39 depicts a sizing tool for sizing the finger of a user. As shown, the tool 2900 can include a plurality of finger holes 3910-3950. The tool 3900 can be made of any material, such as plastic, metal, or cardboard.

Figure 40:
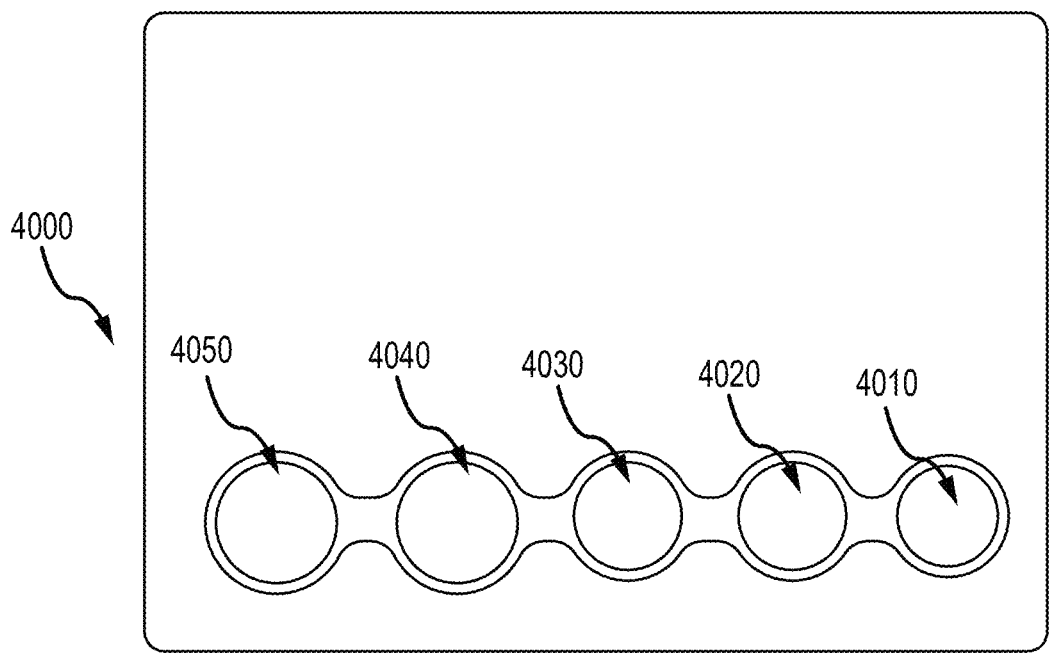
FIG. 40 depicts a sizing tool for sizing the finger of a user according to an alternate example.

FIG. 40 depicts a sizing tool for sizing the finger of a user according to an alternate example. As shown, the tool 4000 can include a plurality of finger holes 4010-4050. The tool 4000 can be made of any material, such as plastic, metal, or cardboard.

Figure 41:
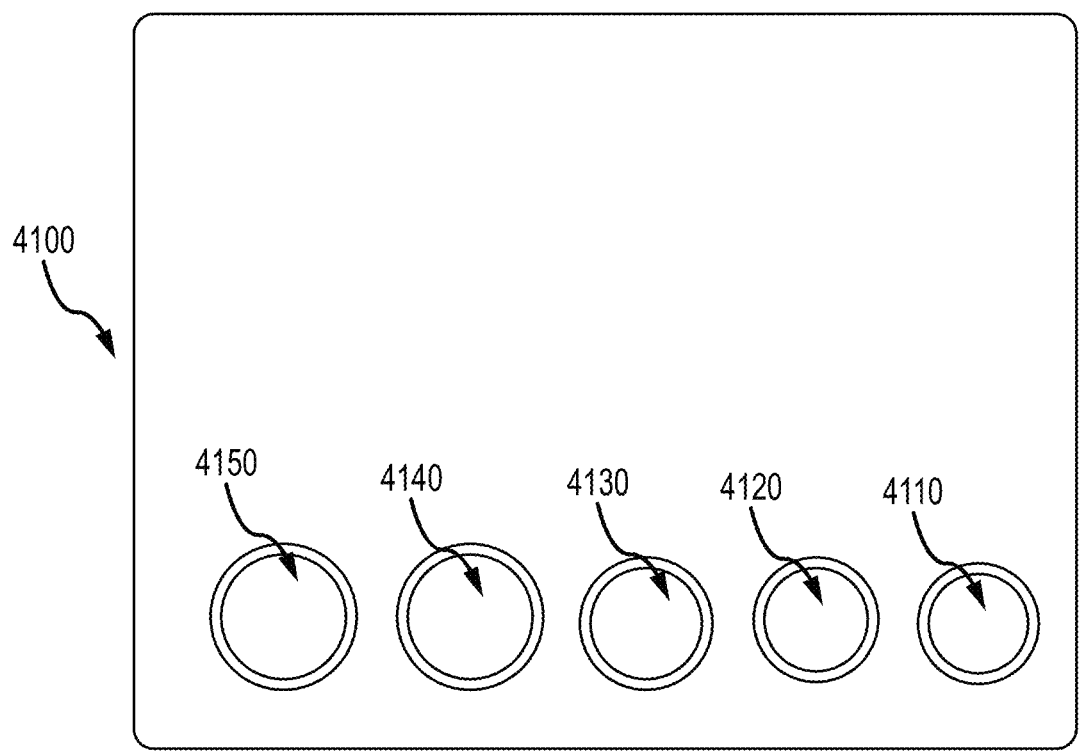
FIG. 41 depicts yet another alternate example of a sizing tool for sizing the finger of a user.

FIG. 41 depicts yet another alternate example of a sizing tool for sizing the finger of a user. As shown, the tool 4100 can include a plurality of finger holes 4110-4150. The tool 4100 can be made of any material, such as plastic, metal, or cardboard. The thickness of the card reflects the thickness of the ring to ensure proper fit. Additionally, the sizing tool is designed such that it can be easily mailed to the user with a standard mail service such as USPS.

Any of the tools 3900, 4000, or 4100 can be provided to a user prior to purchase of the ring in order to obtain accurate sizing information prior to purchase. The tools include holes, as shown above, that can come in a plurality of predetermined finger sizes to allow a user to match his or her finger size with the tool. The best match, e.g., closest size that ensures a comfortable fit, can be identified using the tools. Alternatively, the tools can be provided at retail locations to size the finger of the user on site prior to purchase. More generally, a variety of other sizing techniques, such as those employed by conventional jewelers can be employed according to further aspects of the disclosure.

In another embodiment, a packaging or enclosure of the WCD can include a sizing diagram or interface embodied therein to allow a user to size a finger during the purchase process.

Figure 42:
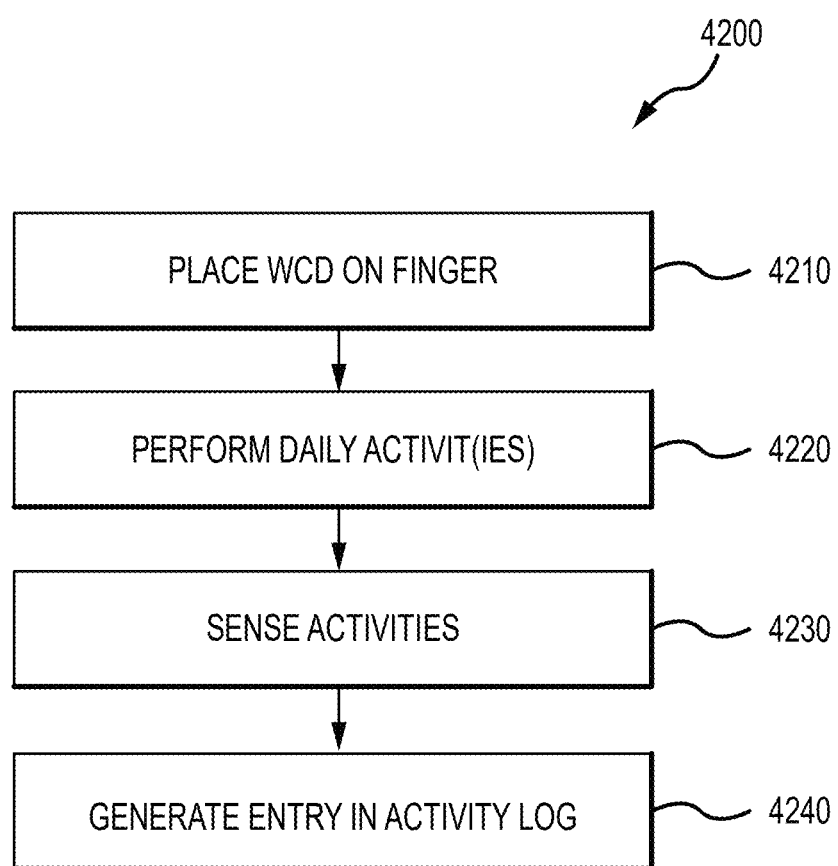
FIG. 42 depicts a method of monitoring activity according to one or more aspects of the disclosure.

FIG. 42 depicts a method 4200 of monitoring activity according to one or more aspects of the disclosure.

At block 4210, a user can don or place the WCD onto the finger to secure it in the wearing position.

At block 4220, a user can perform any number of daily activities, such as running on a treadmill, walking, exercising, typing, etc.

At block 4230, the WCD, contemporaneous with block 3220, can use one or more sensors to sense the activities of the user. For example, the sensors can detect location, speed, acceleration, orientation, heart rate, etc.

At block 4240, the WCD, or another computing device, can generate an entry in an activity log at the conclusion of a detected activity. If the activity detected by the sensors has a profile that has not yet been identified, the WCD can prompt the user to identify the activity. For example, the user can identify profiles such as "Run in Central Park," "Typing," "Run on Treadmill," etc. The WCD can associate the identity provided by the user with the activity profile identified by the sensors and store the identified activity in the WCD memory, or any other memory. Later, if the user performs the same activity and the WCD detects the activity profile as being similar to a saved activity, the WCD can identify the activity while the user is performing the activity and save the activity in the activity log. Each of the activities performed can be saved in the overall activity log and can be stored in a memory on the WCD, or other device, for later viewing.

Figure 43:
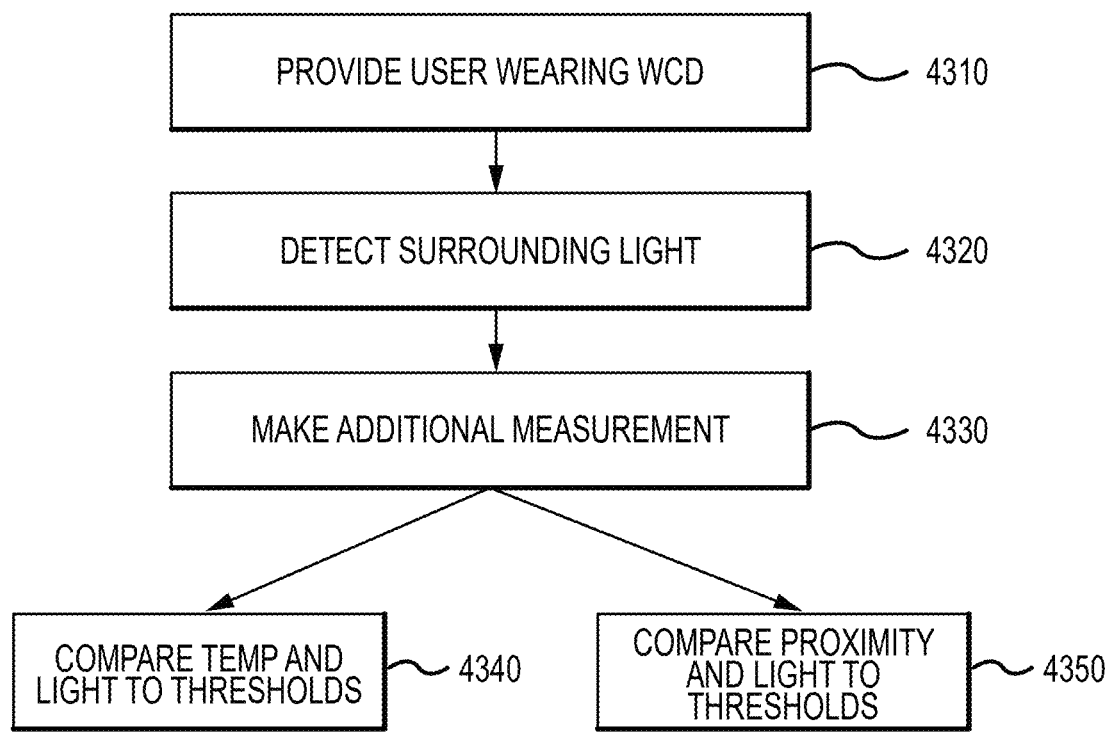
FIG. 43 depicts a method of determining whether a user is wearing gloves according to one or more aspects of the disclosure.

FIG. 43 depicts a method 4300 of determining whether a user is wearing gloves according to one or more aspects of the disclosure. At block 4310, a user is provided while wearing the WCD, where such user may or may not be wearing gloves.

At block 4320, one or more light sensors on board the WCD can detect surrounding ambient light. Such light sensors could include, for example, a CPV or other light sensitive element.

At block 4330, one or more additional measurements maybe made. Such additional measurements can include, for example, an ambient temperature measurement and or a proximity measurement, e.g., detecting proximity of an object to the WCD via reflected electromagnetic radiation in the form of IR light.

At block 4340, a measured ambient temperature and ambient light measurements are compared to predetermined thresholds. If the ambient temperature measurement is above a certain predetermined temperature threshold and the ambient light measurement is below a certain threshold, it can be determined that the user is wearing a glove over the WCD.

At block 4350, a measured proximity and ambient light measurements are compared to respective predetermined thresholds. If the proximity measurement is below a certain distance threshold (e.g., determines an item is in close proximity to the WCD) and the ambient light measurement is below threshold, it can determined that the user is wearing a glove over the WCD. In any of the above examples, an intensity of LED indicators of the WCD can be adjusted according to a detected ambient light using an appropriate algorithm or process that compares the ambient light to a scale and adjusts a desired driving current/voltage for the LEDs according to a predetermined formula (e.g. a proportional adjustment using an adjustment coefficient) or scale (e.g. a lookup table). For example, where there is abundant ambient light (e.g., detected ambient light above a predetermined threshold), the intensity of the LED indicators can be increased. In the same way, where there is little ambient light (detected ambient light below a predetermined threshold), the intensity of the LED indicators can be decreased.

In one example, the WCD can detect whether it is removed and or installed on the finger of the user. In this regard, as mentioned above, the WCD can have inward-facing light sensors, CPV, or temperature sensors. When a user installs a ring on his finger the measure of ambient light may decrease or the temperature may increase. Such changes in ambient light and/or temperature can be detected by one or more sensors onboard the WCD and a determination can be made that the user has removed and or installed the ring on his finger.

Figure 44:
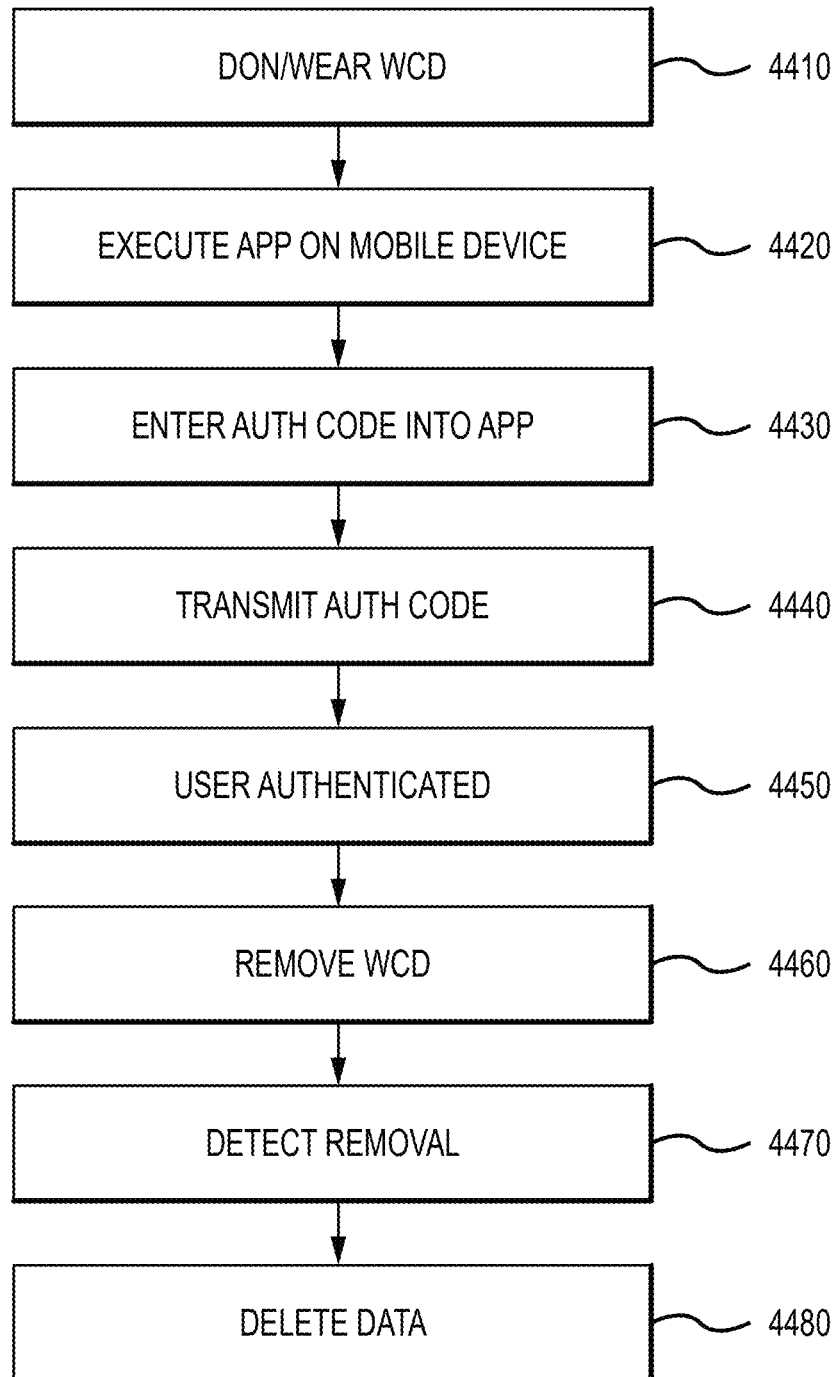
FIG. 44 depicts a method of securing data onboard the WCD according to one or more aspects of the disclosure.

FIG. 44 depicts a method 4400 of securing data onboard the WCD according to one or more aspects of the disclosure. At block 4410, a user may don the WCD on the finger. At block 4420, a user may execute an application on a mobile device, or other computing device, that can be previously associated and authenticated with the WCD. At block 4430, the user can enter an authorization code into the application running on the mobile device, such as a PIN code. At block 4440 the mobile device may transmit the authorization code to the WCD by any means of communication, such as, wired, wireless, Bluetooth, NFC, etc. At block 4450, the user wearing the WCD can now be again authenticated and associated with the WCD and can be granted access to certain functions and/or data storage of the WCD. At block 4460 a user may remove the WCD. At block 4470 the WCD can detect that it is removed such as bio detection (including e.g., biometric identification) techniques described above with respect to inward facing sensor changes, temperature changes, or heart rate decreasing to zero. At block 4480, the authorization code previously stored on the WCD can be automatically deleted upon detection of removal to avoid unauthorized access to such information by a subsequent wearer or other querying party. Further or alternatively, additional information can be automatically deleted upon removal of the WCD, for example any data and or instructions stored on the onboard memory of the WCD such as personal information, banking information, confidential information, or other sensitive data.

IX. TIMEPIECE SYSTEM

Figure 45A:
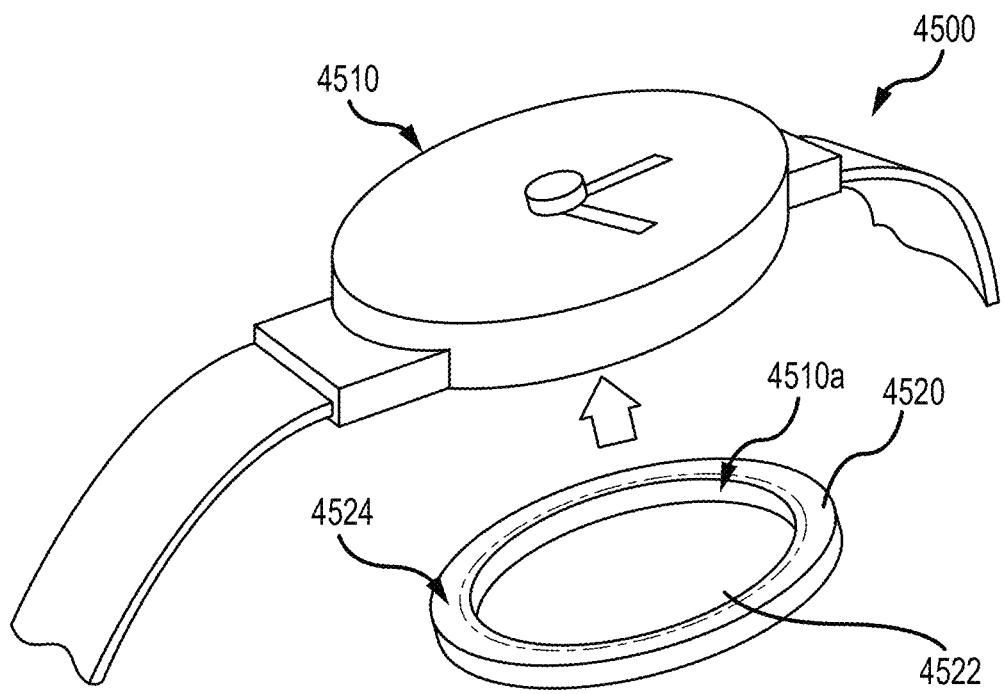
FIG. 45A is a timepiece system according to one or more aspects of the disclosure.

FIG. 45A is a timepiece system 4500 according to one or more aspects of the disclosure. As shown, the timepiece system 4500 can include a conventional timepiece 4510 and a timepiece computing device (TCD) 4520. The TCD can be any shape, and in this example is in the shape of a cylinder. The radius can be significantly greater than a height of the TCD to provide the shape of a puck. The TCD can have one or more structural and/or functional components, and can be similar to the WCD described above with respect to hardware features, components, sensors, etc. Although depicted as cylindrical, the TCD can have any shape depending on the shape of the conventional timepiece. For example, where the timepiece has a rectangular or square face, the TCD can similarly have a rectangular or square profile.

A top surface 4520a of the TCD can include a pressure sensitive adhesive (PSA) layer 4522 to allow for adhesion of the TCD to the under surface of the timepiece 4510. The TCD 4520 can have a radius or circumference that does not exceed radius or circumference of the face of the conventional timepiece so as not to be seen when a user is wearing the timepiece system 4500. The TCD can enhance the conventional timepiece with many of the features described above with respect to the WCD such as, heart rate sensing, temperature sensing pedometer, activity sensing, gesture sensing and control, without having to alter the look of the conventional timepiece.

Figure 45B:
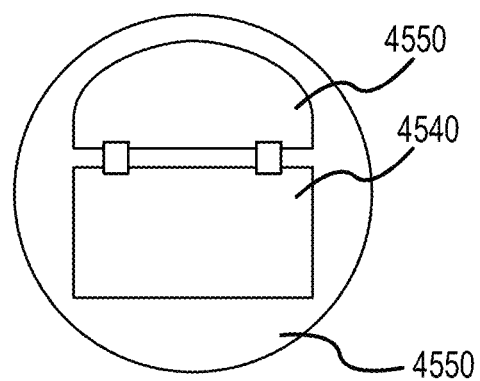
FIG. 45B is a bottom view of the TCD.

FIG. 45B is a bottom view of the TCD. As shown, the TCD can include a battery 4540, any printed circuit board 4550 with one or more components attached thereto (not shown) such as motion sensors, power management circuitry, charging circuitry, etc. As with the WCD, the printed circuit board of the TCD can be overmolded 4560. The overmold can be transparent or substantially transparent to allow electromagnetic radiation to pass through to be incident upon one or more components of the TCD.

As shown, the TCD can include a light pipe 4524 around the perimeter thereof. The light pipe 4524 can be substantially annular in shape and can be formed in part by the overmold of the TCD. The light pipe can be constructed from a conventional transparent or translucent moldable material (e.g. acrylic, polycarbonate, etc.), and can be arranged to focus ambient light onto a CPV disposed onboard the TCD for additional charging capability. The optical arrangement/geometry of the light pipe can be implemented using skill in the art to achieve the desired optical characteristics. In another example, excess heat generated by the TCD or excess body heat emitted from the skin of the user can be converted to electrical energy via a thermoelectric (TEG) module, such as a Peltier module, disposed onboard the TCD.

The TCD can also include any number of CPV cells, either on a top surface or bottom surface, to allow for charging. For example, a CPV cell can be placed on the underside of the TCD to allow for docking with a charging/docking station.

Figure 46:
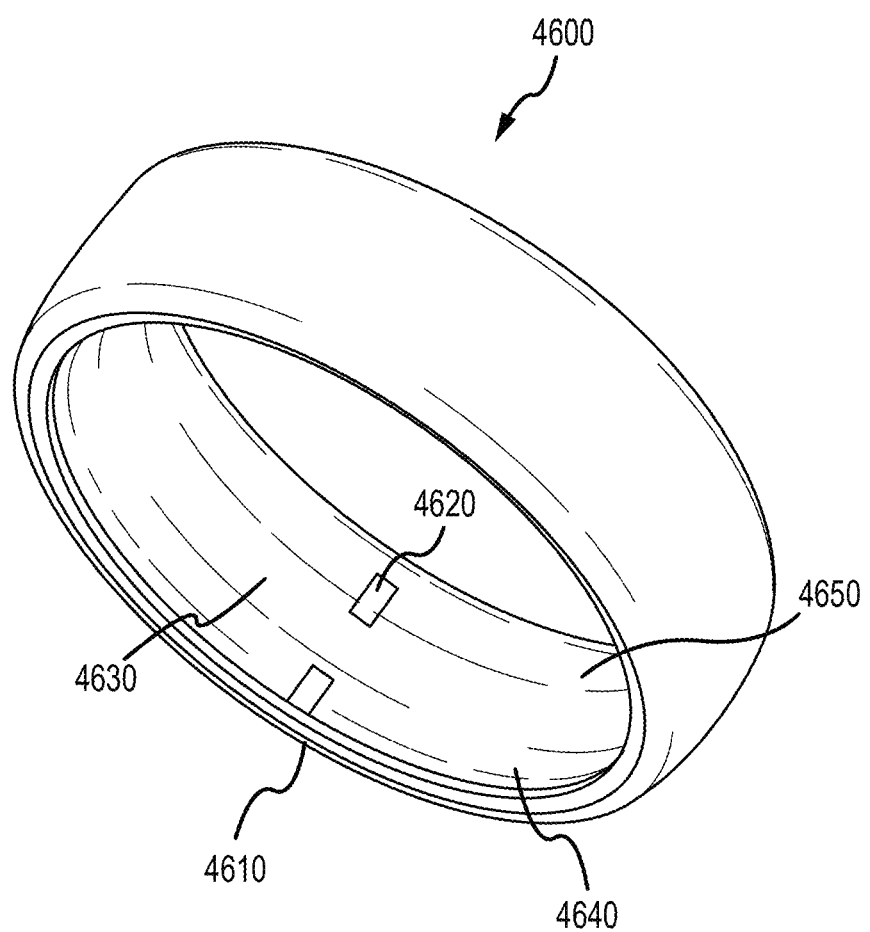
FIG. 46 depicts a WCD with a pair of LED indicators disposed at an inward-facing portion of the WCD.

FIG. 46 depicts a WCD 4600 with a pair of LED indicators 4610-4620 disposed at an inward-facing portion of the WCD. As shown, the WCD 4600 can include a pair of transparent regions 4640-3650 and an opaque region 4630. The LEDs 4610-3620 can be positioned under the transparent regions 4640-3650 to allow light from the LEDs to exit the WCD. In one example, the LEDs 4610-3620 can create a subtle diffuse glow to the skin to provide a desirable visual effect to user. In another example, a user feedback LED can be placed at an inward facing surface and a second can be placed at an outward facing surface of the WCD. Depending on the circumstances, one of the LEDs may be disabled to save battery life. For example, LEDs that are facing away from a user e.g. facing down or away from user's line of sight, may be disabled. As described above, the WCD can determine its orientation based on onboard sensors, such as the magnetometer, accelerometer, GPS, etc.

Figure 47A:
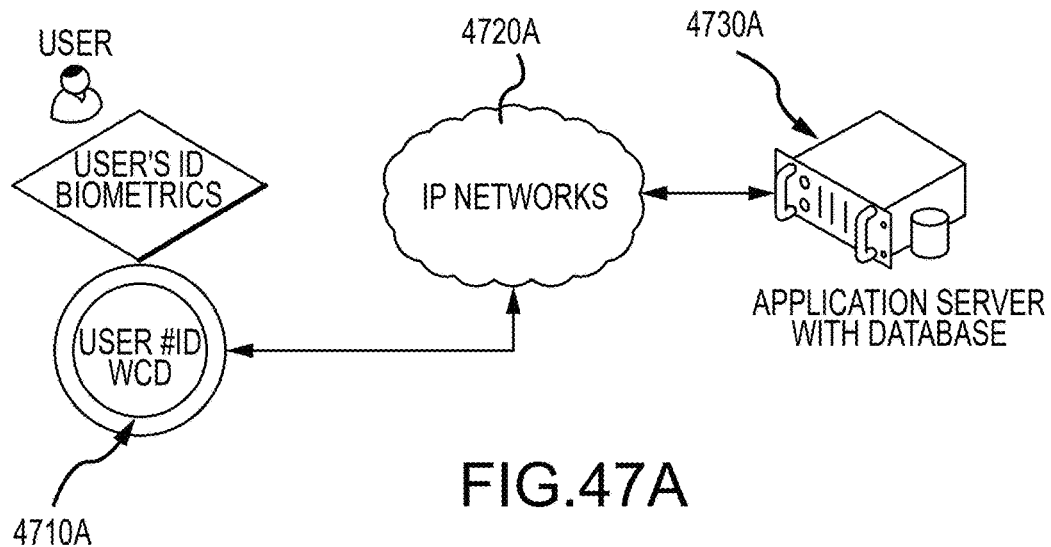
FIG. 47A is a system for generating and managing alerts according to one or more aspects of the disclosure.

FIG. 47A is a system for generating and managing alerts according to one or more aspects of the disclosure. As shown, the system can include a WCD 4710A, one or more networks 4720A, and one or more server computers 4730A according to one or more aspects of the disclosure. The WCD 4710A can communicate directly and/or indirectly with the server 4730A via the network 4720A. In this regard, data generated and/or stored at the WCD 4710A can be transmitted to the server 4730A and vice versa. In one example, such data can include biometric data pertaining to a user wearing the WCD that is detected and stored by the WCD.

Figure 47B:
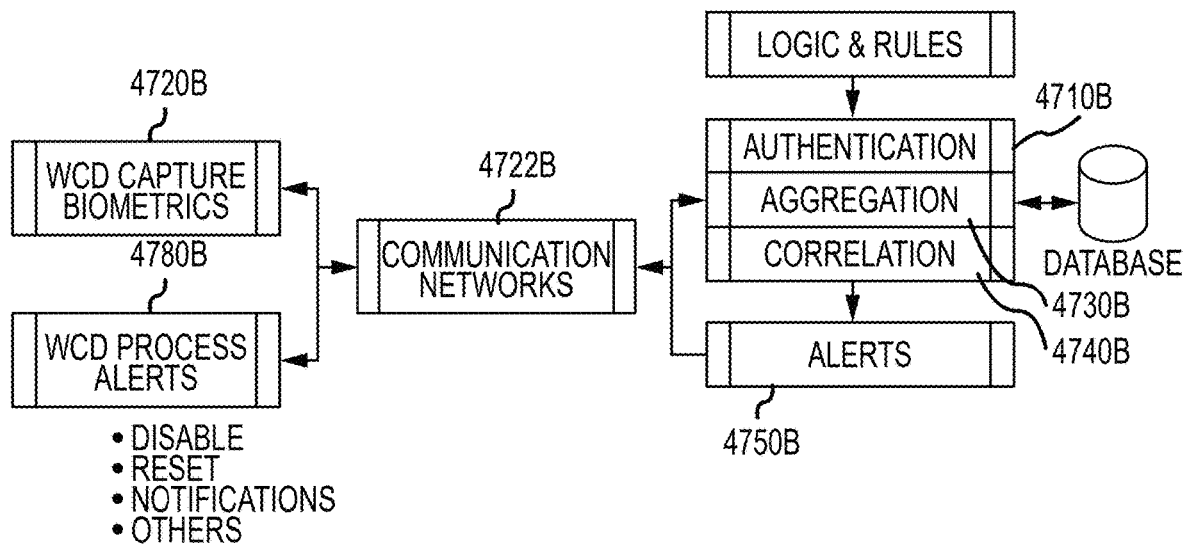
FIG. 47B depicts a block process diagram for generating and managing alerts according to one or more aspects of the disclosure.
Figure 47C:
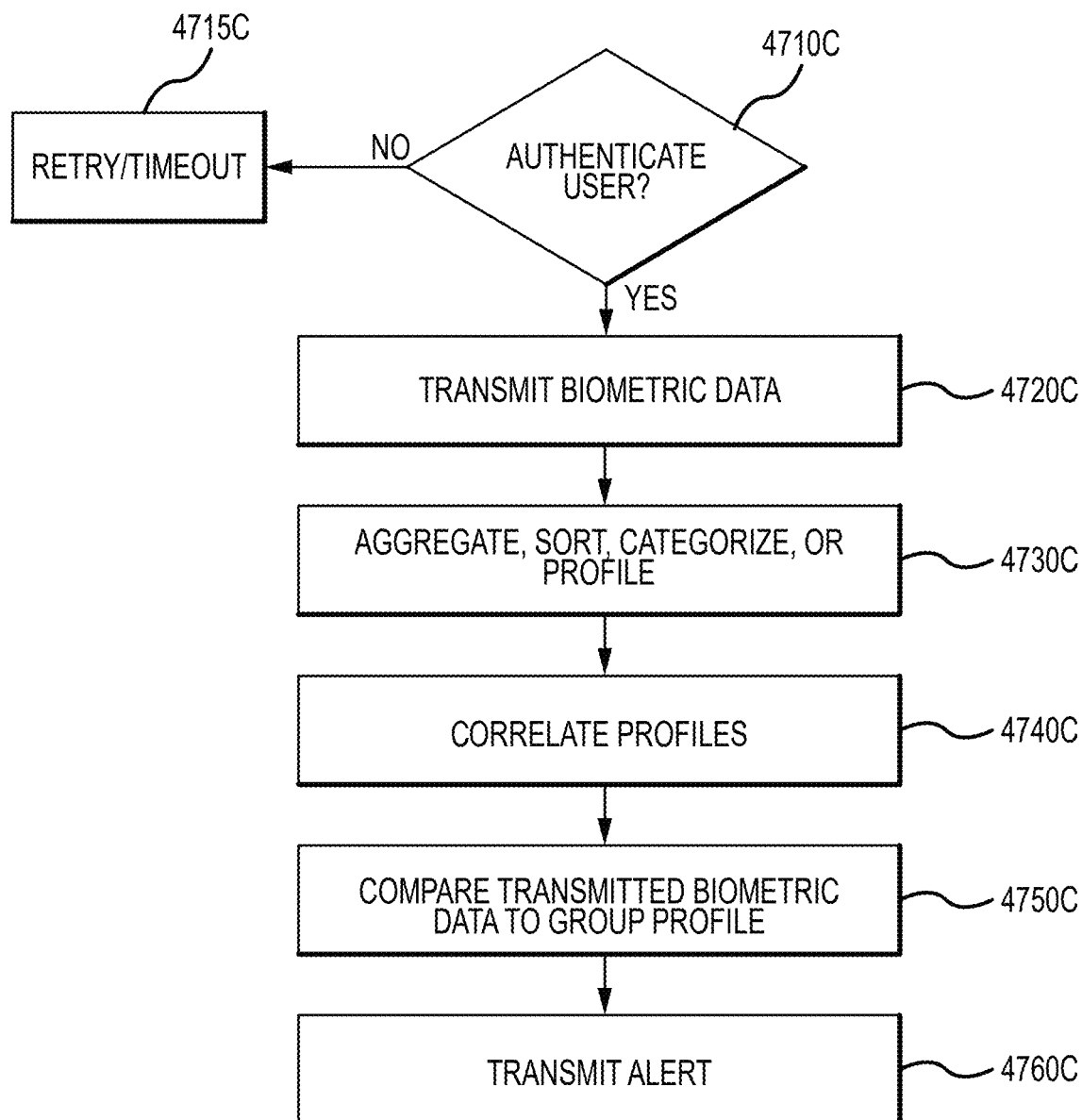
FIG. 47C is a flow chart depicting a method for generating and managing alerts according to one or more aspects of the disclosure.

FIG. 47B depicts a block process diagram for generating and managing alerts according to one or more aspects of the disclosure and FIG. 47C is a flow chart depicting a method for generating and managing alerts according to one or more aspects of the disclosure.

At block 4710C, and as shown at process block 4710B, the user is authenticated with respect to the WCD. In this regard, a single user can be associated with a single WCD and can be associated with a predetermine identifier, such as an alphanumeric number. If the user is not authenticated or the authentication process is not conclusive, the WCD may invite the user to retry authentication at block 4715C until the user is successfully authenticated. In some examples, the WCD may timeout the authentication process, lock the WCD, or place the WCD in safe mode in the event of too many unsuccessful authentication attempts as a security measure.

The user can be authenticated according to any of the authentication methods described in the present application, such as via a unique capillary map, a unique ECG profile, etc.

If the user is authenticated, biometric data can be transmitted to the server at block 4720C. The captured biometric data 4720B can be transmitted to the server via network 4720A, 47222B Once received at the server, the biometric data can be aggregated, sorted, categorized, or profiled at block 4730C and as shown at process block 4730B. In this regard, a profile (corresponding to the alphanumeric identifier) may be created at a database at the server that stores data for a particular user. The profile can store transmitted biometric data, as well as other data, such as user gender, height, weight, age, family history, disease information, location, etc.

In some examples, identifying information may be removed from the data and/or not transmitted to allow for anonymity and/or to comply with regulations regarding transmission of medical data. The transmitted biometric data can be normalized in order to comply with predetermined data requirements in order to be added to the profile. In one example, a minimum amount of data may be required in order to be considered viable for association with the profile. The biometric data of a single profile can be aggregated, or in other examples multiple profiles can be aggregated simultaneously.

Aggregation of the user's biometric data into a single profile allows for the profile to be visualized or analyzed according to any number of methods. For example, a timeline can be created showing biometric data over a period of time. The data can also be synthesized or analyzed to calculate trend data, or other mathematical features.

Although only one WCD is depicted, it is contemplated that a plurality of WCDs can exist, with each WCD corresponding to a distinct user (and distinct alphanumeric identifier) and therefore resulting in a plurality of distinct profiles at the server. Accordingly, each of the distinct users/WCDs may be authenticated separately according to the methods described herein.

At block 4740C, once the transmitted data has been associated with the user profile, the updated profile can be correlated with one or more other profiles stored at the server as shown as process block 4740B. The profiles may be correlated according to any number of correlation standards, such as correlating users with similar traits such as age, gender, location, profession, or by any other data stored at the server. In some examples, one or more of the traits can be used to make such a correlation. The biometric data from the one or more users that are correlated with one another can be combined to form a group profile. The group profile can be the aggregation, average, range, or sum of individual profiles that form the group profile. For example, for a particular group profile, a range of resting heart can be generated by taking the maximum and minimum values of resting heart from the individual profiles. In other examples, an average (and standard deviation or standard deviation of the mean) can be generated for each trait, such as average resting heart rate, average active heart rate, average blood pressure, average blood sugar, average skin temperature, ECG profiles, as well as any other features capable of being detected by the WCD as described above.

At block 4750C, transmitted biometric data can be compared to the established values from the group profile. In this way, if a user's heart rate deviates by a predetermined threshold (such as by predetermined magnitude or standard deviation), an alert can be generated at process block 4750B. The comparison process can occur at the server after transmission of the biometric data. In another example, the group profile data can be transmitted to the WCD for comparison at the WCD. This advantageously allows the comparison to be made where the WCD cannot establish a network link. The group profile can be updated on a continuous basis or a predetermined time interval or at each transmission of biometric data.

At block 4760C, the alert is transmitted to the WCD and displayed to the user at process block 4760B. The alert can indicate that the user's biometric data has deviated from the profile group and may advise the user to seek medical attention. In another example, the server can directly contact a medical health professional. In the example where block 4750C occurs at the WCD, transmission of alert information from the server may not be necessary.

The alert at the WCD can be any type of audio or visual indicator, such as an LED, haptic feedback, audible alarm, etc. The indicator may also invite the user to rest, make an appointment with a medical health professional, recommend a particular medication, or suggest certain physical activities that may health condition that caused the alert.

As shown in FIG. 47B, the authentication 4710B, aggregation 4730B, and correlation 4740B can occur at server 4730A, which can include a process, memory, and any other features of a general purpose computer. The authentication 4710B, aggregation 4730B, and correlation 4740B can access a database stored at the memory, where profiles, group profiles, and biometric data can be stored.

Figure 48A:
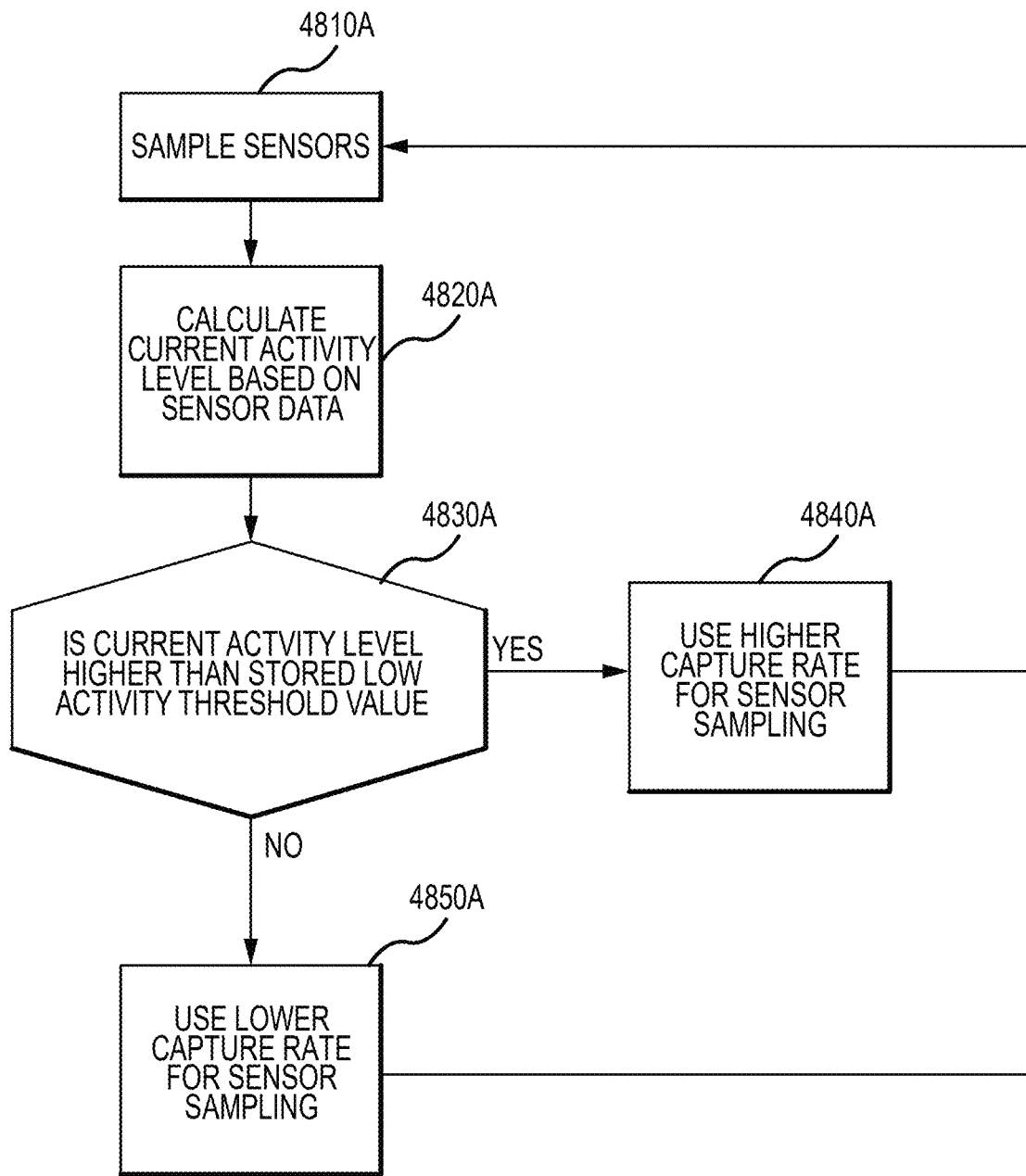
FIG. 48A is a method for variable sampling according to one or more aspects of the disclosure.

FIG. 48A is a method for variable sampling according to one or more aspects of the disclosure. As described above, the processor module of the WCD can determine (e.g., based on identified physical activities, routine pattern, and/or time) a frequency at which one or more sensors in the sensor modules should operate.

At block 4810A, one or more sensors of the WCD may take one or more measurements. For example, the WCD can detect temperature, heart rate, acceleration, as described above.

At block 4820A, the WCD can calculate an activity level of a user. For example, the WCD can compare to a number of stored activity profiles (as described above) stored by the user, or can compare the sensor measurements to sensor threshold values corresponding to different activities, such as sitting, running, sleeping etc. In one example, the WCD detect acceleration values over time to generate an activity level for a particular time period.

At block 4830A, the WCD may compare the identified activity level to a predetermine activity threshold value. In one example, the WCD may categorize the detected activity as either a high level activity or a low level activity. High level activities can include running, swimming, biking etc., while low level activities may include sitting, standing still, or sleeping.

At block 4840A, the WCD can set a first sample rate for high level activities and at block 4850A, the WCD can set a second sample rate for low level activities. The first sample rate can be a shorter time interval than the second sample rate, resulting in more data being detected and generated during a set amount of time while the user is active. This allows for increased power efficiency of the WCD while also providing the advantage of generating more data when a user is more active, thereby providing added biometric data for later analysis.

In another example, the sample rate can be scaled according to activity level. For example, the sample rate can be scaled to be directly proportional to heart rate. This results in a shorter time interval for sampling (more frequent data gather) for running than for walking.

As activity level changes, the method above can be repeated a plurality of times at certain intervals in order to quick or abrupt activity changes.

Figure 48B:
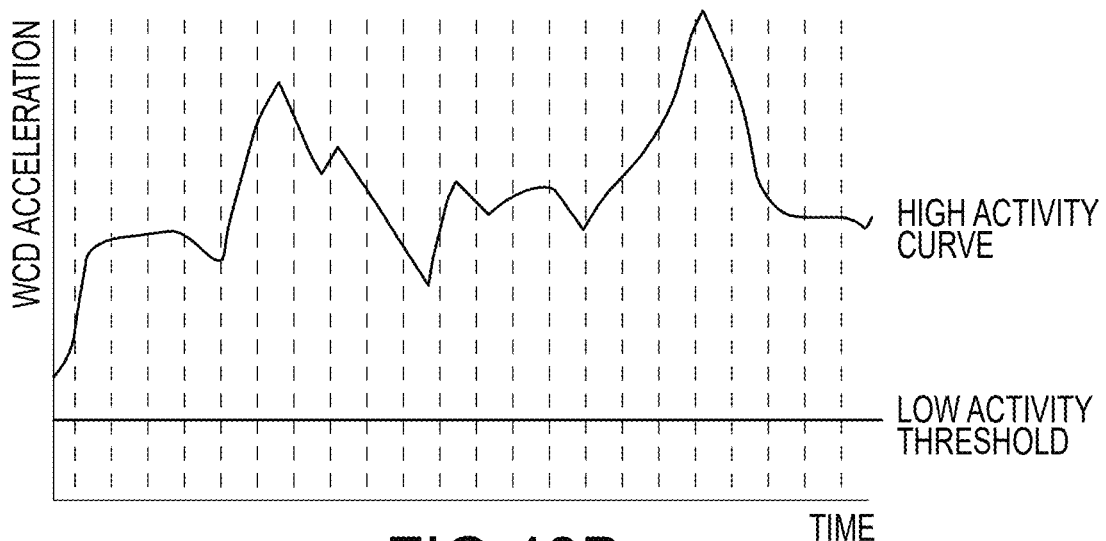
FIGS. 48B and 48C are graphs depicting one or more aspects of the sample method of FIG. 48A.
Figure 48C:
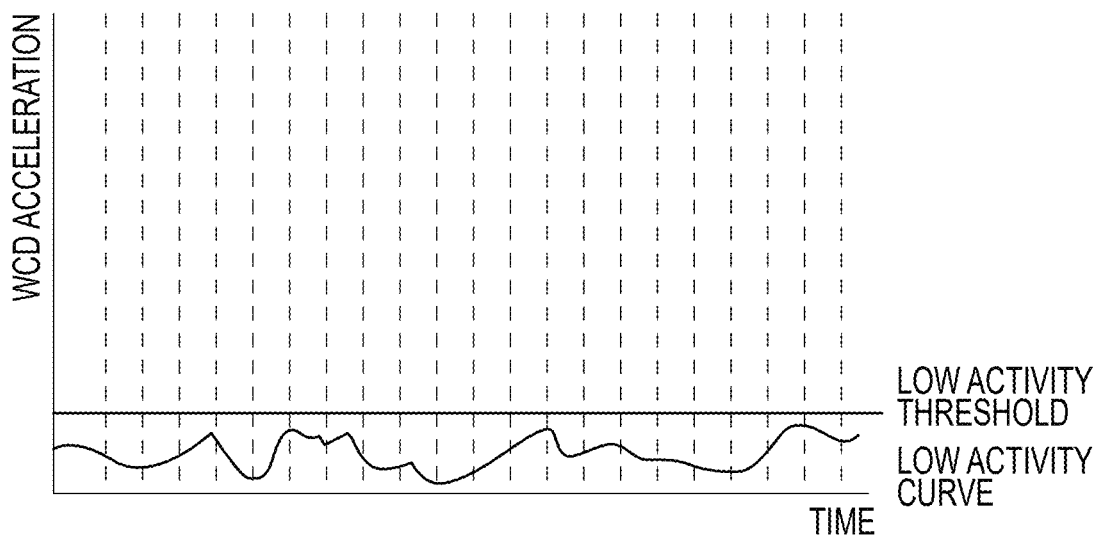

FIGS. 48B and 48c are graphs depicting one or more aspects of the sample method of FIG. 48A. As shown in FIG. 48B, the WCD may determine a user is engaging in a high level activity by detecting acceleration values that are above a predetermined threshold value. In this regard, a shorter time interval (more frequent data gathering) can be set. As shown in FIG. 48C, the user is engaging in a low level activity since the acceleration values are below a predetermined threshold. A longer sample rate (less frequent data gathering) can be set in this instance.

Figure 49:
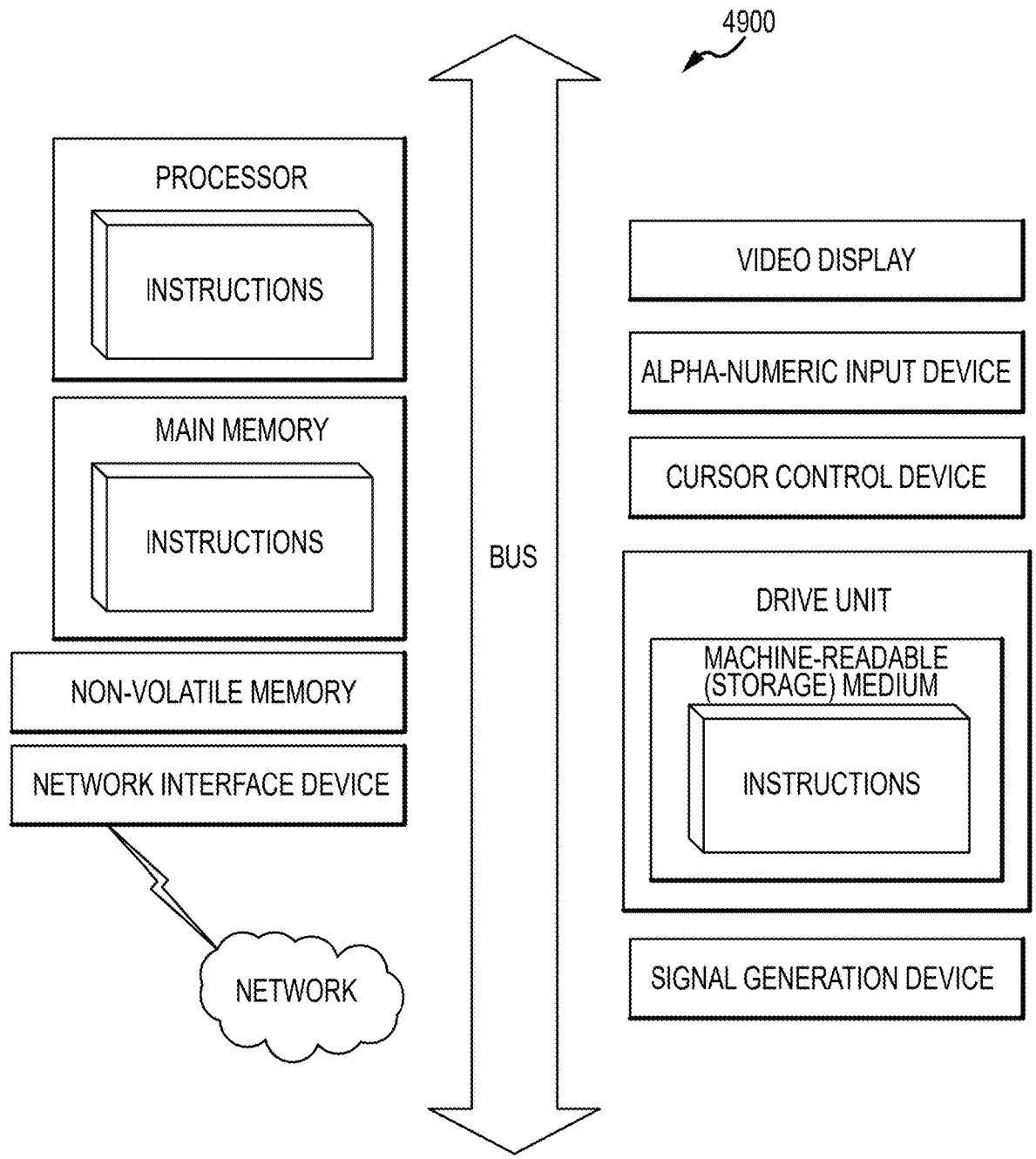
FIG. 49 is a diagrammatic representation of a machine in the example form of a computer system within which a set of instructions, for causing the machine to perform any one or more of the methodologies discussed herein, may be executed.

FIG. 49 a diagrammatic representation of a machine in the example form of a computer system 4900 within which a set of instructions, for causing the machine to perform any one or more of the methodologies discussed herein, may be executed. Specifically, FIG. 49 shows a diagrammatic representation of a machine in the example form of a computer system within which instructions (e.g., software or program code) for causing the machine to perform any one or more of the methodologies discussed herein may be executed. In alternative embodiments, the machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The machine may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute instructions to perform any one or more of the methodologies discussed herein.

The example computer system includes a processor (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory, and a non-volatile memory, which are configured to communicate with each other via a bus. The computer system may further include graphics display unit (e.g., a plasma display panel (PDP), a liquid crystal display (LCD), a projector, or a cathode ray tube (CRT)). The computer system may also include alphanumeric input device (e.g., a keyboard), a cursor control device (e.g., a mouse, a trackball, a joystick, a motion sensor, a touch screen, or other pointing instrument), a storage unit, a signal generation device (e.g., a speaker), and a network interface device, which also are configured to communicate via the bus.

The storage unit includes a non-transitory machine-readable medium on which is stored instructions embodying any one or more of the methodologies or functions described herein. The instructions may also reside, completely or at least partially, within the main memory or within the processor (e.g., within a processor's cache memory) during execution thereof by the computer system, the main memory and the processor also constituting machine-readable media. The instructions may be transmitted or received over a network via the network interface device.

While machine-readable medium is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium that is capable of storing instructions for execution by the machine and that cause the machine to perform any one or more of the methodologies disclosed herein. The term "machine-readable medium" includes, but not be limited to, data repositories in the form of solid-state memories, optical media, magnetic media, or other non-transitory machine readable medium.

X. CONCLUSION

It should be clear that the WCD and TCD arrangements described according to various aspects of the disclosure provide a highly versatile and useful item of wearable electronics that is comfortable and convenient to wear, conveniently charged, and weatherproof for all-purpose and all-condition wearing. Various options for style and appearance can be implemented, as well as a variety of storage options. The functions and structure of the device lend themselves to both a ring version and a wrist-worn version. All versions are designed for long-life with minimal maintenance, and are adaptable to interoperate with a variety of networked devices including computers, smartphones, home controllers, security systems, and virtually any other device capable of communicating over a wireless link-including another WCD or TCD.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, as used herein various directional and orientational terms such as "vertical", "horizontal", "up", "down", "bottom", "top", "side", "front", "rear", "left", "right", and the like, are used only as relative conventions and not as absolute orientations with respect to a fixed coordinate system, such as the acting direction of gravity. Note also, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process, application, and/or processor here herein can be implemented using electronic hardware, software consisting of a non-transitory computer-readable medium of program instructions, or a combination of hardware and software. Also, while a variety of visible and near-visible radiation sources are described as LEDs, it is expressly contemplated that other types of sources can be employed according to aspects of the disclosure—for example plasma discharge sources and bioluminescent sources, as well as sources that are based upon developing technologies. Electronic circuits and RF components can similarly be based on alternate and/or developing technologies. Accordingly, this description is meant to be taken only by way of example, and not to otherwise limit the scope of this invention.

What is claimed is:

1. A method of manufacturing a wearable ring device configured to be worn on a finger of a user, comprising:
constructing an external housing that has an exterior surface, an internal surface, a first sidewall, and a second sidewall, wherein the internal surface, the first sidewall, and the second sidewall define an internal space of the external housing;

inserting a curved battery, a printed circuit board, and one or more components into a curved perimeter of the internal space of the external housing;

applying an internal potting to at least partially fill the internal space of the external housing and cover the curved battery, the printed circuit board, and the one or more components, wherein the internal potting adheres to the external housing; and polymerizing the internal potting, wherein at least a layer of the internal potting forms an interior surface of the wearable ring device that is configured to contact tissue of the user when the wearable ring device is worn by the user, wherein the external housing and the internal potting form a housing for the wearable ring device, wherein the housing has an interior diameter between 12 mm and 24 mm, an exterior diameter between 18 mm and 30 mm, a width between 3 mm and 8 mm, and a thickness between 1.5 mm and 3 mm.

2. The method of claim 1, wherein the internal potting is made of one or more of silicone, epoxy, or polyester resin.

3. The method of claim 1, wherein the internal potting is in liquid or gelatinous form when it is applied to at least partially fill the internal space and solidifies after polymerizing.

4. The method of claim 1, wherein the curved battery is disposed in a first portion of the curved perimeter of the internal space of the external housing, and wherein the printed circuit board is electrically coupled with the curved battery and disposed in a second portion of the curved perimeter of the internal space of the external housing, wherein the first portion and the second portion of the curved perimeter of the internal space are different regions of the wearable ring device.

5. The method of claim 1, wherein the printed circuit board includes a stiffener element to prevent the printed circuit board from being removed or shifting within the internal space while the internal potting is applied.

6. The method of claim 1, wherein the printed circuit board is held in place within the internal space while the internal potting is applied.

7. The method of claim 1, wherein the internal surface, the first sidewall, and the second sidewall form a C-shaped cross section for the external housing.

8. The method of claim 1, wherein the external housing is made of metallic alloy comprising one or more of stainless steel, tungsten, carbide, titanium alloy, silver, platinum, or gold.

9. A method of manufacturing a wearable ring device configured to be worn on a finger of a user, comprising:

constructing an external housing that has an exterior surface, an internal surface, a first sidewall, and a second sidewall, wherein the internal surface, the first sidewall, and the second sidewall define an internal space of the external housing;

inserting a battery, a printed circuit board, and one or more components into a curved perimeter of the internal space of the external housing;

applying at least an epoxy to at least partially fill the internal space of the external housing and cover the battery, the printed circuit board, and the one or more components, wherein the epoxy adheres to the external housing; and solidifying the epoxy, wherein at least a layer of solidified epoxy forms an interior surface of the wearable ring device that is configured to contact tissue of the user when the wearable ring device is worn by the user, wherein the external housing and the solidified epoxy form a housing having a width between 3 mm and 8 mm, and a thickness between 1.5 mm and 3 mm.

10. The method of claim 9, wherein the housing further has an interior diameter between 12 mm and 24 mm and an exterior diameter between 18 mm and 30 mm.

11. The method of claim 9, wherein the epoxy is in liquid or gelatinous form when it is applied to at least partially fill the internal space.

12. The method of claim 9, wherein the battery is disposed in a first portion of the curved perimeter of the internal space of the external housing, and wherein the printed circuit board is electrically coupled with the battery and disposed in a second portion of the curved perimeter of the internal space of the external housing, wherein the first portion and the second portion of the curved perimeter of the internal space are different regions of the wearable ring device.

13. The method of claim 9, wherein the printed circuit board includes a stiffener element to prevent the printed circuit board from being removed or shifting within the internal space while the epoxy is applied.

14. The method of claim 9, wherein the printed circuit board is held in place within the internal space while the epoxy is applied.

15. The method of claim 9, wherein the internal surface, the first sidewall, and the second sidewall form a C-shaped cross section for the external housing.

16. The method of claim 9, wherein the external housing is made of metallic alloy comprising one or more of stainless steel, tungsten, carbide, titanium alloy, silver, platinum, or gold.

* * * * *